US010640793B2

(12) United States Patent
Foody et al.

(10) Patent No.: US 10,640,793 B2
(45) Date of Patent: *May 5, 2020

(54) PROCESS FOR USING BIOGENIC CARBON DIOXIDE DERIVED FROM NON-FOSSIL ORGANIC MATERIAL

(71) Applicant: Iogen Corporation, Ottawa (CA)

(72) Inventors: Patrick J. Foody, Ottawa (CA); Brian Foody, Ottawa (CA)

(73) Assignee: Iogen Corporation, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/327,345

(22) PCT Filed: Jul. 22, 2015

(86) PCT No.: PCT/CA2015/050686
§ 371 (c)(1),
(2) Date: Jan. 18, 2017

(87) PCT Pub. No.: WO2016/011554
PCT Pub. Date: Jan. 28, 2016

(65) Prior Publication Data
US 2017/0158503 A1 Jun. 8, 2017

Related U.S. Application Data

(63) Continuation-in-part of application No. 14/563,116, filed on Dec. 8, 2014, now Pat. No. 9,108,894.
(Continued)

(51) Int. Cl.
| | | |
|---|---|---|
| *C12P 7/14* | (2006.01) | |
| *C01B 3/38* | (2006.01) | |
| *C01B 3/48* | (2006.01) | |
| *C01B 3/50* | (2006.01) | |
| *C01B 32/50* | (2017.01) | |

(Continued)

(52) U.S. Cl.
CPC ............... *C12P 7/14* (2013.01); *C01B 3/38* (2013.01); *C01B 3/48* (2013.01); *C01B 3/50* (2013.01); *C01B 32/50* (2017.08); *C07C 29/1518* (2013.01); *C10G 2/50* (2013.01); *C10L 1/02* (2013.01); *C10L 1/023* (2013.01); *C10L 1/04* (2013.01); *C10L 1/06* (2013.01); *C10L 3/00* (2013.01); *C10L 3/08* (2013.01); *C12F 3/10* (2013.01); *C12P 5/023* (2013.01); *C12P 7/06* (2013.01); *C12P 7/065* (2013.01); *C12P 7/10* (2013.01); *C12P 7/54* (2013.01); *C01B 2203/025* (2013.01); *C01B 2203/0233* (2013.01); *C01B 2203/0244* (2013.01); *C01B 2203/0283* (2013.01); *C01B 2203/043* (2013.01); *C01B 2203/0405* (2013.01); *C01B 2203/0475* (2013.01); *C01B 2203/061* (2013.01); *C01B 2203/062* (2013.01); *C01B 2203/0872* (2013.01); *C01B 2203/1241* (2013.01); *C01B 2203/148* (2013.01); *C10G 2400/02* (2013.01); *C10L 2290/10* (2013.01); *C10L 2290/26* (2013.01); *C10L 2290/42* (2013.01); *C10L 2290/542* (2013.01); *C10L 2290/543* (2013.01); *C10L 2290/545* (2013.01); *Y02E 50/16* (2013.01); *Y02E 50/17* (2013.01); *Y02E 50/343* (2013.01); *Y02P 20/128* (2015.11); *Y02P 20/145* (2015.11); *Y02P 30/10* (2015.11)

(58) Field of Classification Search
CPC .... C07C 1/04; C10G 2/00; C10G 2/32; C10G 2/33; C01B 3/00
See application file for complete search history.

(56) References Cited

U.S. PATENT DOCUMENTS

| | | |
|---|---|---|
| 2,485,044 A | 10/1949 | Gehrke |
| 5,580,457 A | 12/1996 | Erickson |
(Continued)

FOREIGN PATENT DOCUMENTS

| | | |
|---|---|---|
| CA | 2890902 A1 | 5/2014 |
| EP | 450430 B1 | 6/1997 |
(Continued)

OTHER PUBLICATIONS

Abdollahi et al., "CO2/CO Separation by Adsorption in Order to Increase CO2 Conversion to CO via RWGS Reaction", University of Ottawa Presentation, (2012).
Abubackar et al., "Biological Conversion of Carbon Monoxide: Rich Syngas or Waste Gases to Bioethanol", Biofuels Bioproducts and Biorefining, vol. 5 (2011) 93-114.
Black et al., Effects of Firing Coal and Biomass Under Oxy-Fuel Conditions in a Power Plant Boiler Using CFD Modelling, Fuel, vol. 113 (2013) 780-786.
Bonaquist, "Analysis of CO2 Emissions, Reductions, and Capture for Large-Scale Hydrogen Production Plants", Praxair, A White Paper, Oct. 2010.
(Continued)

*Primary Examiner* — Sudhakar Katakam
(74) *Attorney, Agent, or Firm* — Knobbe Martens Olson & Bear LLP

(57) ABSTRACT

The present disclosure provides a process for forming a biogenic carbon-based fuel or a fuel intermediate from biogenic carbon dioxide and hydrogen. The hydrogen is sourced from a process that produces hydrogen and fossil carbon dioxide from a fossil-fuel hydrocarbon and separates the fossil carbon dioxide from the hydrogen. The process may further comprise carrying out or arranging for one or more parties to carry out at least one step that contributes to a reduction in the GHG emissions of the biogenic carbon-based fuel, or a fuel made from the fuel intermediate, of at least 20% relative to a gasoline baseline. In various embodiments this includes (a) introducing the fossil carbon dioxide underground, and/or (b) using a biogenic carbon-based product selected from a chemical and energy product produced from the non-fossil organic material to displace the use or production of a corresponding fossil-based product.

40 Claims, 8 Drawing Sheets

Related U.S. Application Data

(60) Provisional application No. 62/027,370, filed on Jul. 22, 2014, provisional application No. 62/115,273, filed on Feb. 12, 2015.

(51) Int. Cl.

| | |
|---|---|
| *C07C 29/151* | (2006.01) |
| *C10G 2/00* | (2006.01) |
| *C10L 1/02* | (2006.01) |
| *C10L 1/04* | (2006.01) |
| *C10L 1/06* | (2006.01) |
| *C10L 3/00* | (2006.01) |
| *C10L 3/08* | (2006.01) |
| *C12F 3/10* | (2006.01) |
| *C12P 5/02* | (2006.01) |
| *C12P 7/06* | (2006.01) |
| *C12P 7/10* | (2006.01) |
| *C12P 7/54* | (2006.01) |

(56) References Cited

U.S. PATENT DOCUMENTS

| | | | |
|---|---|---|---|
| 5,789,210 A | 8/1998 | Ho et al. | |
| 5,866,382 A | 2/1999 | Hallborn et al. | |
| 6,180,396 B1 | 1/2001 | Ono et al. | |
| 6,475,768 B1 | 11/2002 | Otero et al. | |
| 6,582,944 B1 | 6/2003 | Hallborn et al. | |
| 7,285,402 B2 | 10/2007 | Gaddy et al. | |
| 7,497,191 B2 | 3/2009 | Fulton et al. | |
| 7,527,927 B1 | 5/2009 | Ho et al. | |
| 7,527,951 B2 | 5/2009 | Londesborough et al. | |
| 7,622,284 B2 | 11/2009 | Op Den Camp et al. | |
| 7,964,379 B2 | 6/2011 | Verser et al. | |
| 8,080,693 B2 | 12/2011 | Chornet et al. | |
| 8,212,088 B2 | 7/2012 | Olah et al. | |
| 8,236,534 B2 | 8/2012 | Verser et al. | |
| 8,329,436 B2 | 12/2012 | Verser et al. | |
| 8,354,257 B2 | 1/2013 | Datta et al. | |
| 8,383,376 B2 | 2/2013 | Simpson et al. | |
| 8,404,909 B2 | 3/2013 | Jadhav | |
| 8,507,228 B2 | 8/2013 | Simpson et al. | |
| 8,592,190 B2 | 11/2013 | Gaddy et al. | |
| 8,592,492 B2 | 11/2013 | Chakravarti | |
| 8,647,851 B2 | 2/2014 | Gaddy et al. | |
| 8,658,026 B2 | 2/2014 | Foody et al. | |
| 8,697,405 B2 | 4/2014 | Bell et al. | |
| 8,753,854 B2 | 6/2014 | Foody | |
| 8,759,047 B2 | 6/2014 | Datta et al. | |
| 8,809,015 B2 | 8/2014 | Schultz et al. | |
| 9,034,629 B2 | 5/2015 | Skraly et al. | |
| 9,108,894 B1 * | 8/2015 | Foody | C12P 7/065 |
| 9,476,066 B2 | 10/2016 | Foody | |
| 2003/0111410 A1 | 6/2003 | Branson | |
| 2007/0249029 A1 | 10/2007 | Marshall et al. | |
| 2008/0124775 A1 | 5/2008 | Kovacs et al. | |
| 2009/0151229 A1 | 6/2009 | Rovner | |
| 2010/0076233 A1 | 3/2010 | Cortright et al. | |
| 2010/0105115 A1 | 4/2010 | Simpson et al. | |
| 2010/0298450 A1 | 11/2010 | Datta et al. | |
| 2011/0138684 A1 | 6/2011 | Kranz | |
| 2011/0177564 A1 | 7/2011 | Stephanopoulos | |
| 2012/0231514 A1 | 9/2012 | Geertman et al. | |
| 2012/0285080 A1 | 11/2012 | Despen et al. | |
| 2012/0323714 A1 | 12/2012 | Saxena | |
| 2013/0078687 A1 | 3/2013 | Hickey et al. | |
| 2013/0078689 A1 | 3/2013 | Hickey | |
| 2013/0078690 A1 | 3/2013 | Reed | |
| 2013/0089905 A1 | 4/2013 | Foody | |
| 2013/0131400 A1 | 5/2013 | Duff et al. | |
| 2013/0143972 A1 | 6/2013 | Townsend et al. | |
| 2013/0143973 A1 | 6/2013 | Townsend et al. | |
| 2013/0144087 A1 | 6/2013 | Arora | |
| 2013/0149693 A1 | 6/2013 | Senaratne et al. | |
| 2013/0149767 A1 | 6/2013 | Marion et al. | |
| 2013/0172633 A1 | 7/2013 | Scates et al. | |
| 2013/0255138 A1 | 10/2013 | Mayeur et al. | |
| 2014/0038252 A1 | 2/2014 | Bell et al. | |
| 2014/0080928 A1 | 3/2014 | Kelfkens et al. | |
| 2014/0165569 A1 | 6/2014 | Hsu | |
| 2014/0227752 A1 | 8/2014 | Datta et al. | |
| 2014/0228598 A1 | 8/2014 | Datta et al. | |
| 2014/0256993 A1 | 9/2014 | Melnichuk et al. | |
| 2017/0130582 A1 | 5/2017 | Hsu | |

FOREIGN PATENT DOCUMENTS

| | | |
|---|---|---|
| WO | 2006113293 A1 | 10/2006 |
| WO | 2007117590 A3 | 10/2007 |
| WO | 2008041840 A1 | 4/2008 |
| WO | 2008098254 A2 | 8/2008 |
| WO | 2008157682 A1 | 12/2008 |
| WO | 2011000084 A1 | 1/2011 |
| WO | 2012003849 A1 | 1/2012 |
| WO | 2012062631 A1 | 5/2012 |
| WO | 2010074545 A1 | 6/2012 |
| WO | 2012110257 A1 | 8/2012 |
| WO | 2013036147 A2 | 3/2013 |
| WO | 2013060331 A1 | 5/2013 |
| WO | 2013076293 A2 | 5/2013 |
| WO | 2013090139 A2 | 6/2013 |
| WO | 2013151795 A1 | 10/2013 |
| WO | 2016011555 A1 | 1/2016 |

OTHER PUBLICATIONS

Brooks et al., "Development of a Microchannel In Situ Propellant Production System", Pacific Northwest National Laboratory for US Department of Energy, Contract DE-AC05-76RL01830, PPNL-15456, Sep. 2005.

Brunetti et al., "Membrane Technologies for CO2 Separation", Journal of Membrane Science, vol. 359 (2010) 115-125.

Bustamante et al., "High-Temperature Kinetics of the Homogeneous Reverse Water-Gas Shift Reaction", American Institute of Chemical Engineers, vol. 50, No. 5 (May 2004) 1028-1041.

Butterman et al., "CO2 Enhanced Steam Gasification of Biomass Fuels", Proceedings of 16th Annual North American Waste-to-Energy Conference, Philadelphia PA, May 19-21, 2008.

Centi et al., "Opportunities and Prospects in the Chemical Recycling of Carbon Dioxide to Fuels", Catalysts Today, vol. 148 (2009) 191-205.

Chen et al., "Methanol Synthesis from CO2 Using a Silicone Rubber/Ceramic Composite Membrane Reactor", Separation and Purification Technology, vol. 34 (2004) 227-237.

Datar et al., "Fermentation of Biomass-Generated Producer Gas to Ethanol", Biotechnology and Bioengineering, vol. 86, No. 5 (Jun. 5, 2004) 587-594.

Doty et al., "Toward Efficient Reduction of CO2 to CO for Renewable Fuels", Proceedings of Energy Sustainability 2010, Phoenix, AZ, May 17-22, 2010.

Environmental Protection Agency, "Regulation of Fuels and Fuel Additives: Identification of Additional Dualifying Renewable Fuel Pathways Under the Renewable Fuel Standard Program" Federal Register, vol. 78, No. 43, Mar. 5, 2013, 14190-14217.

Francesconi et al., "Analysis of Design Variables for Water-Gas-Shift Reactors by Model-Based Optimization", Journal of Power Sources, vol. 173 (2007) 467-477.

Genthner et al., "Growth of Eubacterium Limosum with Carbon Monoxide as the Energy Source", Applied and Environmental Microbiology, vol. 43, No. 1 (1982) 70-74.

Global CSS Institute, "Air Products Steam Methane Reformer EOR Project" http://www/globalccsinstitute.com/project/air-products-steam-methane-reformer-eor-project, Access Date May 12, 2014.

Gomez-Barea et al., "Biomass Gasification Integrated Into a Coal Oxy-Boiler", 19th European Biomass Conference, Berlin, Germany, Jun. 6, 2011.

Green Car Congress, "$12M German Project to Develop Technology for Syngas Production from CO2 and H2; New Hydrogen

(56) References Cited

OTHER PUBLICATIONS

Production Method", Jul. 2, 2013, www.greencarcongress.com/2013/07/basf-20130702.html, Accessed May 22, 2014.
Green Car Congress, "Algae Species Shows Promise in Reducing Power Plant Pollution and Making Biofuel", Jul. 2, 2013, www.greencarcongress.com/2013/07/coyne-20130702.html, Accessed May 22, 2014.
Green Car Congress, "Algae.Tec Signs Carbon Capture Biofuels Deal with Australia's Largest Coal-Fired Power Company", Jul. 2, 2013, www.greencarcongress.com/2013/07/algaetec-20130702.html, Accessed May 22, 2014.
Haldor Topsoe, "From Solid Fuels to Substitute Natural Fas (SNG) Using TREMP™", Brochure, Mar. 2009.
Hensley, "Catalysts for Mixed Alcohol Synthesis from Biomass Derived Syngas" NREL, CRADA Report, NREL/TP-7A10-57656, CRD-08-292, Apr. 2013.
Holladay et al., "Microreactor Development for Martian In Situ Propellant Production", Catalysis Today, vol. 120 (2007) 35-44.
Holladay et al., "Compact Reverse Water-Gas-Shift Reactor for Extraterrestrial In Situ Resource Utilization", Journal of Propulsion and Power, vol. 24, No. 3, May-Jun. 2008, 578-582.
Hu et al., "Catalyst Development for Microchannel Reactors for Martian In Situ Propellant Production" Catalysis Today, vol. 125 (2007) 103-110.
IEA-ETSAP et al. "Production of Bio-Methanol" Technology Brief 108, Jan. 2013.
INEOS, "INEOS Bio / Process Technology", Brochure, Apr. 2012.
International Search Report and Written Opinion in PCT Application No. PCT/CA2015/050686, dated Oct. 27, 2015.
Jiang et al., "Turning Carbon Dioxide Into Fuel" Philosophical Transactions of the Royal Society A, vol. 368 (2010) 3343-3364.
Joo et al., "CAMERE Process for Methanol Synthesis from CO2 Hydrogenation", Studies in Surface Science and Catalysis, 153 (2004) 67-72.
Joo et al., "Carbon Dioxide Hydrogenation to Form Methanol via a Reverse-Water-Gas-Shift Reaction (the CAMERE Process)", Industrial and Engineering Chemistry Research, vol. 38 (1999), 1808-1812.
Kohn, "Catalytic Reforming of Biogas for Syngas Production", Submission to Columbia University, 2012.
Li et al., "Utilization of Carbon Dioxide from Coal-Fired Power Plant for the Production of Value-Added Products", Submission for Design Engineering of Energy and Geo-Environmental Systems Course (EGEE 580), College of Earth and Mineral Science, Apr. 2006.
Liew et al., "Gas Fermentation for Commercial Biofuels Production", Liquid, Gaseous and Solid Biofuels—Conversion Techniques, Chapter 5 (2013) InTech 125-173.
Luo et al., "Innovative Methods for Biogas Upgrading by the Addition of Hydrogen to Anaerobic Reactor", DTU Environment, Department of Environmental Engineering, Copenhagen, Denmark, Oct. 24-25, 2015.
Lv et al. "Bio-Syngas Production from Biomass Catalytic Gasification", Energy Conversion and Management, vol. 48 (2007) 1132-1139.
Membrane Technology and Research, Inc. "CO2 Removal from Syngas", Brochure, 2009.
Mohammadi et al., "Kinetic Studies on Fermentative Production of Biofuel from Synthesis Gas Using Clostridium Ljungdahlii", The Scientific World Journal, vol. 2014, Article ID 910590, Jan. 30, 2014.
Morrison, "Production of Ethanol from the Fermentation of Synthesis Gas", Thesis submitted to Mississippi State University, Aug. 2004, 1-143.
Munasinghe et al., "Biomass-Derived Syngas Fermentation into Biofuels: Opportunities and Challenges", Bioresource Technology, vol. 101 (2010) 5013-5022.
Muradov et al., "'Green' Path from Fossil-Based to Hydrogen Economy: An Overview of Carbon-Neutral Technologies", International Journal of Hydrogen Energy, vol. 33 (2008) 6804-6839.

Najafpour et al., "Ethanol and Acetate Synthesis from Waste Gas Using Batch Culture of Clostridium Ljungdahlii", Enzyme and Microbial Technology, vol. 38 (2009) 223-228.
Olah, "Beyond Oili and Gas: The Methanol Economy", Angewandte Chemie International Edition, vol. 44 (2005) 2636-2639.
Olah et al., "Chemical Recycling of Carbon Dioxide to Methanol and Dimethyl Ether: From Greenhouse Gas to Renewable, Environmentally Carbon Neutral Fuels and Synthetic Hydrocarbons", Journal of Organic Chemistry, vol. 74 (2009) 487-498.
Park et al., "Development of ZnO/Al2O3 Catalyst for Reverse-Water-Gas-Shift Reaction of CAMERE (carbon dioxide hydrogenation to form methanol via a reverse-water-gas-shift reaction) Process", Applied Catalysis A: General, vol. 211 (2001) 81-90.
Peer et al., "Separation of Hydrogen from Carbon Monoxide Using a Hollow Fiber Polyimide Membrane: Experimental and Simulation", Chemical Engineering Technology, vol. 30, No. 10 (2007) 1418-1425.
Phillips et al., "Synthesis Gas as Substrate for the Biological Production of Fuels and Chemicals", Applied Biochemistry and Biotechnology, vol. 45/46 (1994) 145-157.
Regalbuto,"An NSF Perspective on Next Generation Hydrocarbon Biorefineries", Computers and Chemical Engineering, vol. 34 (2010) 1393-1396.
Richter et al., "A Two-Stage Continuous Fermentation System for Conversion of Syngas into Ethanol", Energies, vol. 6 (2013) 3987-4000.
Ryden et al., "Using Steam Reforming to Produce Hydrogen with Carbon Dioxide Capture by Chemical-Looping Combustion", International Journal of Hydrogen Energy, vol. 31 (2006) 1271-1283.
Schultz et al., "Synthesis of Hydrocarbon Fuels Using Renewable and Nuclear Energy", American Nuclear Society, vol. 166, No. 1 (2009) 56-63.
Schultz et al., "Hydrogen and Synthetic Hydrocarbon Fuels—A Natural Synergy", National Hydrogen Association Annual Meeting Longbeach, CA, Mar. 13-16, 2006.
Serrano-Ruiz et al., "Catalytic Routes for the Conversion of Biomass into Liquid Hydrocarbon Transportation Fuels", Energy & Environmental Science, vol. 4 (2011) p. 83-89.
Shelley, "Capturing CO2: Membrane Systems Move Forward", Chemical Engineering Progress, vol. 105, No. 4 (Apr. 2009) 42-47.
Shen et al., "Chemical Fixation of Carbon Dioxide Catalyzed by Binaphthyldiamino Zn, Cu, and Co Salen-Type Complexes", Journal of Organic Chemistry, vol. 68 (2003) 1559-1562.
Spath et al., "Life Cycle Assessment of Hydrogen Production via Natural Gas Steam Reforming", National Renewable Energy Laboratory, NREL/TP-570-27637, Feb. 2001.
Spivey et al., "Heterogeneous Catalytic Synthesis of Ethanol from Biomass-Derived Syngas", Chemical Society Reviews, vol. 36 (2007) 1514-1528.
Subramani et al., "A Review of Recent Literature to Search for an Efficient Catalytic Process for the Conversion of Syngas to Ethanol", Energy & Fuels, vol. 22 (2008) 814-839.
Sun et al., "In Situ IR Studies on the Mechanism of Methanol Synthesis over an Ultrafine Cu/ZnO/Al2O3 Catalyst", Applied Catalysis A: General, vol. 171 (1998) 301-308.
Toftegaard, "OxyFuel Combustion of Coal and Biomass", Ph.D. Thesis submitted to Technical University of Denmark and Dong Energy Power, Mar. 31, 2001.
Vanhassel et al. "Advanced Oxy-fuel Boilers for Cost-Effective CO2 Capture", Praxair Presentation, Fourth Annual Conference on Carbon Capture & Sequestration, May 2-5, 2005.
Walton et al., "A Novel Adsorption Cycle for CO2 Recovery: Experimental and Theoretical Investigations of a Temperature Swing Compression Process", Separation Science and Technology, vol. 41 (2006) 485-500.
Wang et al., "Methanation of Carbon Dioxide: an Overview", Frontiers of Chemical Science and Engineering , vol. 5, No. 1 (2011) 2-10.
Wang et al., "Recent Advances in Catalytic Hydrogenation of Carbon Dioxide", Chemical Society Reviews, vol. 40 (2011) 3703-3727.

(56) References Cited

OTHER PUBLICATIONS

Wang et al., "Reverse Water Gas Shift Reaction Over Co-precipitated Ni—CeO2 Catalysts", Journal of Rare Earths, vol. 26 (2008) 66-70.
Wikipedia, "Electrochemical Reduction of Carbon Dioxide" http:/en.wikipedia.org/wiki/Electrochemical_reduction_of_carbon_dioxide, Access date: May 12, 2014.
Wikipedia, "Green Methanol Synthesis", http:/en.wikipedia.org/wiki/Green_Methanol_Synthesis, Access date: May 9, 2014.
Xu et al., "Adding Value to Carbon Dioxide from Ethanol Fermentations", Bioresource Technology, vol. 101 (2010) 3311-3319.
Environmental Protection Agency, "Deferral for CO2 Emissions from Bioenergy and Other Biogenic Sources Under the Prevention of Significant Deterioration (PSD) and Title V Programs", Federal Register, vol. 76, No. 139 (Jul. 20, 2011).
International Search Report and Written Opinion in International Application No. PCT/CA2015/050687, dated Oct. 23, 2015.
Al-Hasan, M., Effect of ethanol-unleaded gasoline blends on engine performance and exhaust emission. Energy Conversion and Management (2003), v44(9), p. 1547-61.
Canilha et al. Bioconversion of Sugarcane Biomass into Ethanol: An Overview about Composition, Pretreatment Methods, Detoxification of Hydrolysates, Enzymatic Saccharification, and Ethanol Fermentation. Journal of Biomedicine and Biotechnology (2012), Article ID 989572, 12 pages (2012).
Costa et al. Growth Inhibition Kinetics for the Acetone-Butanol Fermentation. Foundations of Biochemical Engineering (1983) Ch 24, p. 501-512 (1983).
Kundiyana et al. Syngas fermentation in a 100L pilot scale fermentor: Design and process considerations. Journal of Bioscience and Bioengineering (2010), v105(5) p. 492-98.
Luong et al. Kinetics of Ethanol Inhibition in Alcohol Fermentation. Biotechnology and Bioengineering (1985), v27, p. 280-285 (1985).
Mayank et al. Mathematical Models of ABE fermentation: review and analysis. Critical Reviews in Biotechnology (2013) V33(4), p. 419-447 (2013).
Moulin et al. Inhibition of Alcoholic Fermentation by Substrate and Ethanol. Biotechnology and Bioengineering (1980), v22, p. 2375-2381 (1980).
Osman et al. Mechanism of Ethanol Inhibition of Fermentation in Zymomonas mobilis CP4. Journal of Bacteriology (1985), v164(1), p. 173-180 (1985).
Corn Steep Liquor—Technical Evaluation Report. USDA National Organic Program. 8 pages(2010).

* cited by examiner

PROCESS FOR USING BIOGENIC CARBON DIOXIDE DERIVED FROM NON-FOSSIL ORGANIC MATERIAL

This application is a national stage application of PCT/CA2015/050686 having an international filing date of Jul. 22, 2015, which claims benefit of U.S. provisional application No. 62/027,370 filed Jul. 22, 2014, U.S. provisional application No. 62/115,273 filed Feb. 12, 2015, and U.S. patent application Ser. No. 14/563,116 filed Dec. 8, 2014, now U.S. Pat. No. 9,108,894, each of which is incorporated by reference herein in its entirety.

TECHNICAL FIELD

The present invention relates to a process for using biogenic carbon dioxide derived from non-fossil organic material for producing a fuel or fuel intermediate.

BACKGROUND

The majority of the energy used today is derived from fossil fuels, despite the ongoing controversy surrounding their environmental impact. Fossil fuels, as with any carbon-containing materials, release carbon dioxide upon their combustion. The extraction of fossil fuels for energy production results in the release of carbon into the atmosphere that was previously stored in the earth, and thereby has a net effect of increasing the levels of atmospheric carbon dioxide. A major source of atmospheric fossil carbon dioxide comes from "tailpipe emissions" from cars and carbon dioxide-containing flue gases from fossil fuel burning power plants.

On the other hand, carbon dioxide released from combusting fuel derived from non-fossil organic material is relatively benign, given that it simply returns to the atmosphere carbon that was recently fixed by photosynthesis. More generally, this relatively benign nature is also true of carbon dioxide released as a byproduct from the processing of non-fossil organic material during fermentation or other processes that break down organic material into simpler molecules. Carbon dioxide sourced from non-fossil organic material is referred to herein as biogenic carbon dioxide, as described below. Fuels or fuel intermediates containing biogenic carbon are known as "biofuels" or "biofuel intermediates" and the tailpipe emissions from biofuels are generally considered benign to the atmosphere.

Displacing fossil-based fuel with fuel made from non-fossil organic material creates atmospheric greenhouse gas (GHG) benefits by displacing carbon dioxide emissions that would have been from the fossil fuel and would have led to an increase in atmospheric levels of carbon dioxide. Carbon dioxide is a greenhouse gas and has been identified as a contributor to global climate change. Various governments have promoted the increased use of renewable fuel through legislative and regulatory regimes, including the Energy Independence and Security Act (EISA) in the U.S. Some of the purposes of the EISA are to increase the production of clean renewable fuels, to promote research on and deploy GHG capture and to reduce fossil fuels present in transportation fuels. In addition to EISA, numerous jurisdictions, such as the state of California, the province of British Columbia, Canada and the European Union, have set annual targets for reduction in average life cycle GHG emissions of transportation fuel. Such an approach is often referred to as a Low Carbon Fuel Standard ("LCFS"), where credits may be generated for the use of fuels that have lower life cycle GHG emissions than a specific baseline fuel.

Despite these government incentives, biofuels still do not enjoy widespread use due to technical and cost limitations. One challenge with commercializing biofuels is that the yield of fuel from the starting material is often low. A variety of factors contribute to these low yields. For example, in the fermentative production of ethanol from non-fossil organic material, such as corn, a significant amount of the carbon from the sugar is not converted into fuel product. During fermentation, the yeast produces carbon dioxide in addition to the desired ethanol product. From one mole of glucose, two moles of each ethanol and carbon dioxide are produced. This carbon is usually not captured as the carbon dioxide is typically vented to atmosphere due to its low energy value and, given that the carbon dioxide is biogenic, it has no net effect on the life cycle GHG emissions of the ethanol.

Moreover, only the carbohydrate-rich portion of organic material, such as grain or the stalks of sugar cane, is readily converted to ethanol. While the production of fuel from these parts of the plant can be carried out with relative ease, the structural parts of the plant also contain sugar in the form of cellulose and hemicellulose, which is generally more difficult to convert to biofuel. Since these parts of the plant are not converted to product in such fuel fermentation processes, this represents a significant yield loss.

Research efforts have been directed toward the development of processes that can convert the non-edible cellulose and hemicellulose portion of plant material to fuels. A first chemical processing step for converting non-edible parts of plants to ethanol, or other fermentation products, involves breaking down the fibrous material to liberate sugar monomers from the plant material. This can be achieved by hydrolyzing the hemicellulose first to its constituent sugars, using a chemical such as sulfuric acid, followed by hydrolysis of the cellulose to glucose by enzymes referred to as cellulase enzymes. These sugars are then fermented to ethanol with yeast or bacteria. A non-sugar containing component that remains after the conversion, known as lignin, can be burned to generate heat and power for internal plant operations. Thus, the process benefits from maximizing the whole plant for fuel or energy production. Nonetheless, there are challenges in obtaining a high yield of sugar for subsequent fermentation due to the recalcitrance of the cellulose to enzymatic hydrolysis. Although there is on-going research aimed at improving the efficiency of this step, progress is slow and the process is still costly.

Another approach for utilizing the whole plant involves subjecting the organic material to gasification to make syngas, which is composed of carbon monoxide, hydrogen and typically carbon dioxide. Syngas can then be used as a precursor to make additional chemicals or used as a fuel itself. While the whole plant, including both the carbohydrate and lignin components, can be converted to syngas, some of the energy stored in the sugar polymers is lost in the process. Moreover, many side products are produced, including tars and carbon dioxide which are not converted to fuel and thus contribute to yield loss.

SUMMARY

In accordance with one embodiment, a process for making fuels or fuel intermediates from non-fossil organic material is provided that improves product yield from non-fossil organic material and/or maintains a beneficial GHG emission impact.

In accordance with one embodiment, biogenic carbon dioxide produced during the production of a fuel, fuel intermediate, chemical product or energy product from non-fossil organic material is collected and used as a carbon source to increase product yield and produce more fuel or fuel intermediate at lower cost. In conventional processes for making fuels or other products from non-fossil organic material, carbon dioxide is frequently vented as its recovery is often perceived as impractical due to its low energy value and because the carbon dioxide is GHG neutral, meaning that it simply returns to the atmosphere carbon that was recently fixed by plants. In accordance with one embodiment, biogenic carbon dioxide derived from non-fossil organic material is collected and/or used as a carbon source to produce a biogenic carbon-based fuel or fuel intermediate. Accordingly, a greater amount of the carbon from the non-fossil organic material is converted to a biogenic carbon-based fuel or fuel intermediate. This results in significant improvements in product yield from the original non-fossil organic material.

According to various embodiments, the biogenic carbon-based fuel or fuel intermediate is formed from the biogenic carbon dioxide and hydrogen in one or more chemical and/or biological conversion steps, representative examples of which are described herein. In one embodiment, the hydrogen is sourced from a process that produces fossil carbon dioxide and hydrogen from a fossil fuel hydrocarbon, and separates fossil carbon dioxide from the hydrogen. The separated hydrogen, also referred to herein as "fossil derived hydrogen" is then used to make the biogenic carbon-based fuel or fuel intermediate.

Despite being produced partially from fossil fuel hydrocarbon, the biogenic carbon-based fuel or fuel intermediate still can have favorable life cycle GHG emissions. While fossil derived hydrogen is used in the biofuel production, since the hydrogen does not itself contain fossil carbon, the carbon dioxide tailpipe emissions that result from combustion of the biofuel, such as in transportation vehicles, contain only or mostly biogenic carbon, and thus are considered to have a neutral effect on atmospheric carbon dioxide levels. Although the carbon dioxide emissions associated with the hydrogen production from fossil fuels are included in the GHG emissions analysis, by practicing embodiments of the invention, the life cycle GHG emissions of the fuel or fuels produced can be reduced relative to a gasoline baseline, while at the same time using a low cost fossil derived hydrogen source.

According to various embodiments, the fossil carbon dioxide that is separated from the hydrogen is introduced underground. This results in the removal of the fossil carbon dioxide that might otherwise be vented to the atmosphere, thereby reducing the life cycle GHG emission reductions associated with the biofuel or biofuel intermediate.

An additional advantage of using the fossil derived hydrogen in fuel production is that it possesses a high energy content, whereas the separated fossil carbon dioxide possesses low energy content. Thus, the higher energy hydrogen produced from fossil fuel hydrocarbon becomes incorporated into the biofuel, avoiding the detrimental tailpipe emissions of conventional fossil based fuels noted above, while the low energy fossil carbon dioxide is introduced underground, and does not contribute to atmospheric carbon dioxide levels.

In certain embodiments, the yield of the biogenic carbon-based fuel or products that can be achieved from the non-fossil organic material can be increased by at least 10%, 25%, or 30% relative to a conventional biofuel production process. By "yield", it means the British Thermal Units (BTU) of biogenic carbon-based fuel that can be produced from a given weight of raw material, as measured using the "Low Heating Value" using ASTM methodology known in the art. For instance, if ethanol is the biogenic carbon-based fuel produced by the process, the total amount of ethanol produced can be increased by 10% or more relative to a conventional corn ethanol production process in which biogenic carbon dioxide is not collected.

Further, by using fossil derived hydrogen and biogenic carbon dioxide to form a fuel or fuel intermediate as described herein, the process provides for even greater increases in product yield from the original non-fossil organic material than conventional processes for producing a biofuel from such material. In certain embodiments as set forth further herein, by virtue of adding fossil derived hydrogen energy to make biofuel, for example ethanol, the yield conventionally referred to as "theoretical yield", which is the yield based on the amount of product that would be formed if the fermentation reaction went to completion, can be exceeded.

Thus, according to a first aspect of the invention, there is provided a process for producing a fuel or fuel intermediate containing carbon derived from non-fossil organic material for fuel production comprising: (i) providing biogenic carbon dioxide that is sourced from a production process comprising a step of fermentation, said production process producing a first product derived from the non-fossil organic material, the first product selected from: (a) an energy product; (b) a biogenic carbon-based product selected from a chemical product, a fuel and a fuel intermediate; and (c) a combination thereof, wherein biogenic carbon dioxide is generated during the production process and collected; (ii) providing a stream enriched in hydrogen that is sourced from a hydrogen production process comprising the steps of: (a) converting fossil methane to carbon monoxide and hydrogen by reforming, (b) converting at least a portion of the carbon monoxide by a water-gas shift reaction to carbon dioxide, thereby producing a stream comprising fossil carbon dioxide and hydrogen, and (c) separating at least a portion of the hydrogen from the stream of step (b) from non-hydrogen components to produce the stream enriched in hydrogen and a stream comprising fossil carbon dioxide; (iii) converting the biogenic carbon dioxide from step (i) and hydrogen produced in step (ii)(c) to a second product by a process comprising at least one chemical or biological conversion, wherein the second product so produced is a biogenic carbon-based fuel or fuel intermediate; and (iv) carrying out or arranging for one or more parties to carry out at least one step that contributes to a reduction in the life cycle GHG emissions of a fuel or a fuel made from a fuel intermediate produced by the process, wherein the life cycle GHG emissions are reduced by at least 20% relative to a gasoline baseline, the at least one step selected from: (a) introducing at least a portion of fossil carbon dioxide recovered from one or more streams comprising fossil carbon dioxide generated during the hydrogen production process into an apparatus for transporting carbon dioxide, withdrawing carbon dioxide from the apparatus and introducing the withdrawn carbon dioxide underground, and (b) using at least a portion of the first product selected from a chemical and energy product to displace the use or production of a corresponding fossil-based product, wherein the life cycle GHG emissions of the fuel are measured by EPA methodology as described herein.

According to a second aspect, the present invention provides a process for using biogenic carbon dioxide derived from non-fossil organic material for fuel production comprising: (i) providing biogenic carbon dioxide that is sourced from a production process comprising a step of fermentation, the production process producing a first product derived from the non-fossil organic material, the first product selected from: (a) an energy product; (b) a biogenic carbon-based product selected from a chemical product, a fuel and a fuel intermediate; and (c) a combination thereof, wherein biogenic carbon dioxide is generated during the production of the first product and collected; (ii) providing a stream enriched in hydrogen that is sourced from a hydrogen production process comprising the steps of: (a) converting fossil methane to carbon monoxide and hydrogen by reforming; (b) converting at least a portion of the carbon monoxide by a water-gas shift reaction to carbon dioxide, thereby producing a stream comprising carbon dioxide and hydrogen, and (c) separating at least a portion of the hydrogen from the stream of step (b) from non-hydrogen components to produce the stream enriched in hydrogen and a stream comprising fossil carbon dioxide; (iii) converting the biogenic carbon dioxide from step (i) and hydrogen produced in step (ii)(c) to a second product by a process comprising at least one chemical or biological conversion, wherein the second product so produced is a biogenic carbon-based fuel or fuel intermediate; and (iv) generating or causing the generation of a biofuel credit as a result of producing the second product.

According to a third aspect of the invention, there is provided a process for using biogenic carbon dioxide derived from non-fossil organic material for fuel production comprising: (i) providing biogenic carbon dioxide that is sourced from a production process comprising a step of fermentation; (ii) providing a stream enriched in hydrogen that is sourced from a hydrogen production process comprising the steps of: (a) converting fossil methane to carbon monoxide and hydrogen by reforming, (b) converting at least a portion of the carbon monoxide by a water-gas shift reaction to carbon dioxide, thereby producing a stream comprising carbon dioxide and hydrogen, and (c) separating at least a portion of the hydrogen from the stream of step (b) from non-hydrogen components to produce the stream enriched in hydrogen; and (iii) converting the biogenic carbon dioxide from step (i) and hydrogen produced in step (ii)(c) to a biogenic carbon-based fuel, fuel intermediate or chemical product. In one embodiment of the invention, in step (iii), a biogenic carbon-based fuel or fuel intermediate is produced, which fuel or fuel intermediate is ethanol. In a further embodiment of the invention, in step (iii) a chemical product is produced, which chemical product is an organic acid such as acetic acid, acetate or a combination thereof.

In some embodiments of any of the foregoing aspects of the invention, the production process of step (i) may produce an alcohol or an organic acid. The alcohol may be ethanol. In some embodiments, at least a portion of the biogenic carbon dioxide provided in step (i) is sourced from (a) a fermentation to produce the ethanol, (b) an anaerobic digestion of a process stream resulting after a step of recovering the ethanol, or (c) a combination thereof. In addition to producing ethanol, the production process of step (i) may further comprise the production of lignin.

In some embodiments, the production process of step (i) produces at least one energy product that is steam, electricity, methane and/or lignin.

According to one embodiment, a fuel or fuel intermediate is produced in the production process of step (i) that is the same type as the biogenic carbon-based fuel or fuel intermediate produced in step (iii).

In one embodiment, the biogenic carbon-based fuel or fuel intermediate of step (iii) is an alcohol, including ethanol or methanol.

In one embodiment, the biogenic carbon-based fuel or fuel intermediate of step (iii) is a liquid or gaseous hydrocarbon at 20° C. The hydrocarbon may be selected from methane and gasoline. Alternatively, the hydrocarbon may be a liquid hydrocarbon produced by a Fischer Tropsch reaction.

In one embodiment, step (iii) comprises a biological conversion that is a fermentation. The fermentation may produce an alcohol such as ethanol.

In another embodiment, the production process of step (i) is an ethanol production process comprising a step of producing biogenic ethanol from a fermentation and wherein the biogenic carbon dioxide is generated during the ethanol production process and collected, and wherein step (iii) comprises introducing biogenic carbon dioxide from step (i) and hydrogen from step (ii) together or separately to a fermentation reactor and forming additional biogenic ethanol by converting the biogenic carbon dioxide and hydrogen in the reactor to biogenic ethanol by fermentation with a microorganism. The biogenic carbon dioxide and hydrogen may be introduced together or separately with a fermentation broth.

Embodiments of the first and third aspect of the invention may further comprise carrying out or arranging for one or more parties to carry out at least one step that contributes to a reduction in the life cycle GHG emissions of a fuel or a fuel made from a fuel intermediate produced by the process, wherein the life cycle GHG emissions of the fuel are at least 20% lower than a gasoline baseline, the at least one step selected from: (a) introducing at least a portion of fossil carbon dioxide recovered from one or more streams comprising fossil carbon dioxide generated during said hydrogen production process into an apparatus for transporting carbon dioxide, withdrawing carbon dioxide from the apparatus and introducing the withdrawn carbon dioxide underground, and (b) using at least a portion of a product produced in the production process of step (i) selected from a chemical and energy product to displace the use or production of a corresponding fossil-based product. In one embodiment, the life cycle GHG emissions are measured by EPA methodology. In an alternative embodiment, the life cycle GHG emissions are measured by LCFS methodology.

In further embodiments of the first and third aspect of the invention, a biofuel credit is generated or caused to be generated. The biofuel credit may be a Renewable Identification Number (RIN) or an LCFS credit.

In certain embodiments of any of the foregoing aspects of the invention, the amount of biogenic carbon in the second biogenic carbon-based fuel or fuel intermediate may be between 72 mole % and 100 mole %, between 75 mole % and 100 mole %, between 80 mole % and 100 mole %, between 85 mole % and 100 mole %, between 90 mole % and 100 mole % or between 95 mole % and 100 mole % (mol:mol of biogenic:non-biogenic carbon).

According to a fourth aspect of the invention, there is provided a process for increasing biogenic ethanol production from non-fossil organic material comprising: (i) providing biogenic carbon dioxide that is sourced from an ethanol production process comprising producing biogenic ethanol from a fermentation of the non-fossil organic material, wherein biogenic carbon dioxide is generated during the ethanol production process and collected; (ii) providing a stream comprising hydrogen that is sourced from a process that produces fossil carbon dioxide and hydrogen from a fossil-fuel hydrocarbon, the stream comprising a molar ratio of hydrogen to fossil carbon monoxide and carbon dioxide of greater than 4:1; (iii) introducing biogenic carbon dioxide from step (i) and hydrogen from step (ii) together or separately to a fermentation reactor; and (iv) forming additional biogenic ethanol by converting the biogenic carbon dioxide and hydrogen in the reactor to biogenic ethanol by fermentation with a microorganism.

According to a fifth aspect of the invention, there is provided a process for increasing biogenic ethanol production from non-fossil organic material comprising: (i) providing biogenic carbon dioxide that is sourced from an ethanol production process comprising producing biogenic ethanol from a fermentation of the non-fossil organic material, wherein biogenic carbon dioxide is generated during the ethanol production process and collected; (ii) providing a stream enriched in hydrogen that is sourced from a hydrogen production process comprising the steps of: (a) converting fossil methane to carbon monoxide and hydrogen by reforming; (b) converting at least a portion of the carbon monoxide by a water-gas shift reaction to produce a stream comprising fossil carbon dioxide and hydrogen; and (c) separating at least a portion of the hydrogen from the stream to produce the stream enriched in hydrogen; (iii) introducing biogenic carbon dioxide from step (i) and hydrogen produced in step (ii)(c) together or separately to a fermentation reactor; and (iv) forming additional biogenic ethanol by converting the biogenic carbon dioxide and hydrogen in the reactor to ethanol by fermentation with a microorganism.

In certain embodiments of any of the foregoing aspects of the invention, the stream enriched in hydrogen or comprising hydrogen has a molar ratio of hydrogen to the combined amount of fossil carbon monoxide and carbon dioxide of greater than 5:1, greater than 6:1, greater than 7:1, greater than 8:1, greater than 10:1 or greater than 15:1.

In further embodiments of any of the foregoing aspects of the invention, the stream enriched in hydrogen or a stream comprising hydrogen contains less than 5 mole % fossil carbon, less than 3 mole % fossil carbon, less than 2 mole % fossil carbon, less than 1 mole % fossil carbon or less than 0.5 mole % fossil carbon.

In yet further embodiments of any of the foregoing aspects of the invention, the stream enriched in hydrogen or a stream comprising hydrogen contains greater than 90 mol %, 93 mol %, 95 mol %, 96 mol %, 97 mol %, 98 mol % or 99 mol % hydrogen (mol:mol).

In those embodiments of the invention in which ethanol is produced, the amount of biogenic carbon in the additional biogenic ethanol produced in step (iv) above may be between 70 and 100 mole %, between 75 mole % and 100 mole %, between 80 mole % and 100 mole %, between 85 mole % and 100 mole %, between 90 mole % and 100 mole % or between 95 mole % and 100 mole % (mol:mol of biogenic and non-biogenic carbon).

According to another aspect of the present invention there is provided a conversion process comprising: (a) producing or causing one or more parties to produce a first fuel, fuel intermediate, chemical product or energy product and biogenic carbon dioxide from non-fossil organic material; (b) providing biogenic carbon dioxide that has been recovered from step (a); (c) converting or causing one or more parties to convert the biogenic carbon dioxide derived from the non-fossil organic material into a second fuel in one or more biologic and/or chemical conversion steps, wherein such fuel has a heat of combustion of at least 22 MJ/kg, measured as a Low Heating Value by standard ASTM methodology, and wherein the conversion process incorporates hydrogen from fossil fuel that has had fossil carbon dioxide removed; and (d) optionally generating or causing the generation of a fuel credit as a result of the favorable GHG emissions profile of a fuel produced by the process.

According to a further aspect of the invention, there is provided a process for producing a biogenic carbon-based fuel, fuel intermediate or chemical product comprising: (i) providing biogenic carbon dioxide that is sourced from a production process using non-fossil organic material as a feedstock; (ii) providing a stream comprising hydrogen by converting fossil methane to carbon monoxide and hydrogen by reforming; (iii) converting the biogenic carbon dioxide from step (i) and hydrogen produced in step (ii) to the biogenic carbon-based fuel, fuel intermediate or chemical product; (iv) obtaining a process stream comprising organic components from (a) the production process of step (i); (b) one or more stages of a process comprising step (iii); or (c) a combination thereof, and carrying out anaerobic digestion of the process stream to produce a crude biogas; and (v) generating or causing the generation of a fuel credit with respect to the use of methane sourced from biogas produced in step (i), (iv), or both steps as a transportation or heating fuel.

According to an embodiment of the invention, carbon dioxide removed from the crude biogas is introduced to step (iii).

The process stream comprising organic components may comprise organic acids, such as acetic acid, acetate, or a combination thereof, and/or soluble lignin.

In a further embodiment, a fuel or fuel intermediate is produced in step (iii), and the process further comprises generating or causing the generation of a fuel credit with respect to the fuel or a fuel produced from the intermediate.

In a further embodiment, a fuel is produced in step (iii), and the fuel is ethanol. The process may further comprise generating or causing generation of a fuel credit with respect to the ethanol.

In a further embodiment, the biogenic carbon dioxide provided in step (i) is processed to remove oxygen. The oxygen content in the stream comprising the biogenic carbon dioxide may be less than 20 ppm, less than 15 ppm or less than 10 ppm. Removal of oxygen has been found to improve gaseous fermentation of hydrogen and carbon dioxide to the fuel, fuel intermediate or chemical product. The oxygen may be removed by distillation or other known processing techniques.

In a further aspect of the invention, there is provided a process for producing a biogenic carbon-based fuel, fuel intermediate or chemical product comprising: (i) providing biogenic carbon dioxide that is sourced from a production process using non-fossil organic material as a feedstock; (ii) providing a stream comprising hydrogen by converting fossil methane to carbon monoxide and hydrogen by reforming; (iii) converting the biogenic carbon dioxide from step (i) and hydrogen produced in step (ii) to the biogenic carbon-based fuel, fuel intermediate or chemical product; and (iv) using heat from the reforming as process energy (a) in the production process of step (i); (b) in one or more stages of a process comprising step (iii) to produce the biogenic carbon-based fuel, fuel intermediate or chemical product; or (c) a combination thereof.

In one embodiment, a chemical product is produced in step (iii), which chemical product is acetic acid, acetate, or a combination thereof.

The heat from the reforming can be used in any stage of the production process of step (i). In an embodiment, the production process of step (i) comprises fermentation. The heat from the reforming may be used in a step of drying a stream remaining after recovery of a fermentation product from the fermentation or for producing steam and/or electricity in the production process. In further embodiments of the invention, a chemical product is produced, which chemical product may be an organic acid such as acetic acid, acetate or a combination thereof.

In a further aspect of the invention, there is provided a process for producing a biogenic carbon-based fuel, fuel intermediate or chemical product comprising: (i) providing biogenic carbon dioxide that is sourced from non-fossil organic material; (ii) providing a stream comprising hydrogen by converting fossil methane to carbon monoxide and hydrogen by reforming; (iii) converting the biogenic carbon dioxide from step (i) and hydrogen produced in step (ii) to the biogenic carbon-based fuel, fuel intermediate or chemical product; (iv) carrying out anaerobic digestion of a process stream comprising organic components to produce a crude biogas comprising biogenic carbon dioxide; (v) removing at least a portion of the biogenic carbon dioxide from the biogas to produce a stream comprising additional biogenic carbon dioxide; and (vi) introducing the additional biogenic carbon dioxide removed from the crude biogas to step (iii), step (i) or both steps.

The process stream comprising organic components may comprise organic acids, such as acetic acid, acetate, or a combination thereof, and/or soluble lignin.

According to one embodiment, a fuel or fuel intermediate is produced in step (iii), and the process further comprises generating or causing the generation of a fuel credit with respect to the fuel or a fuel produced from the intermediate.

In a further embodiment of the invention, a fuel is produced in step (iii), which fuel is ethanol. The process may further comprise generating or causing generation of a fuel credit with respect to the ethanol.

In a further embodiment of the invention, the biogenic carbon dioxide provided in step (i) is processed to remove oxygen.

In yet a further aspect of the invention, there is provided a process for producing a biogenic carbon-based fuel, fuel intermediate or chemical product comprising: (i) providing biogenic carbon dioxide that is sourced from non-fossil organic material; (ii) providing a stream comprising hydrogen by converting fossil methane to carbon monoxide and hydrogen by reforming; (iii) fermenting the biogenic carbon dioxide from step (i) and hydrogen produced in step (ii) to a biogenic carbon-based fuel, fuel intermediate or chemical product; (iv) carrying out anaerobic digestion on a stream produced in the process comprising organic components to produce biogas; (v) obtaining a byproduct from step (iii) of fermenting; and (vi) introducing the byproduct to the anaerobic digestion of step (iv).

Various byproducts from the fermentation of step (iii) may be introduced to the step (iv) anaerobic digestion. The byproduct may be an organic acid such as acetate, acetic acid, or a combination thereof. In a further embodiment of the invention, the byproduct is an exhaust gas stream comprising at least one of hydrogen, carbon monoxide and carbon dioxide. Introducing such byproducts to the anaerobic digestion of step (iv) can potentially increase biogas yields. The biogas can then be used directly as a transportation or heating fuel or introduced to a pipeline from which methane is withdrawn for transportation use.

In those aspects of the invention comprising the step of providing a stream comprising hydrogen by converting fossil methane to carbon monoxide and hydrogen by reforming, at least a portion of the carbon monoxide may be converted by a water-gas shift reaction to carbon dioxide, thereby producing a stream comprising carbon dioxide and hydrogen. Subsequently, at least a portion of the hydrogen from the stream comprising carbon dioxide and hydrogen may be separated from non-hydrogen components to produce the stream comprising hydrogen.

According to one embodiment, there is provided a process for using biogenic carbon dioxide derived from non-fossil organic material for fuel production comprising: (i) providing biogenic carbon dioxide that is sourced from a production process comprising a step of fermentation, said production process producing a first product derived from the non-fossil organic material, said first product selected from: (a) an energy product; (b) a biogenic carbon-based product selected from a chemical product, a fuel and a fuel intermediate; and (c) a combination thereof, wherein biogenic carbon dioxide is generated during the production process and collected; (ii) providing a stream enriched in hydrogen that is sourced from a hydrogen production process comprising the steps of: (a) converting fossil methane to carbon monoxide and hydrogen by reforming; (b) converting at least a portion of the carbon monoxide by a water-gas shift reaction to carbon dioxide, thereby producing a stream comprising carbon dioxide and hydrogen, and (c) separating at least a portion of the hydrogen from the stream of step (b) from non-hydrogen components to produce the stream enriched in hydrogen and a stream comprising fossil carbon dioxide; (iii) converting the biogenic carbon dioxide from step (i) and hydrogen produced in step (ii)(c) to a second product by a process comprising at least one chemical or biological conversion, wherein said second product so produced is a biogenic carbon-based fuel or fuel intermediate; and (iv) generating or causing the generation of a biofuel credit as a result of producing the second product.

In one embodiment, there is provided a process for increasing biogenic ethanol production from non-fossil organic material comprising: (i) providing biogenic carbon dioxide that is sourced from an ethanol production process comprising producing biogenic ethanol from a fermentation of the non-fossil organic material, wherein biogenic carbon dioxide is generated during the ethanol production process and collected; (ii) providing a stream comprising hydrogen that is sourced from a process that produces fossil carbon dioxide and hydrogen from a fossil-fuel hydrocarbon, said stream comprising a molar ratio of hydrogen to fossil carbon monoxide and carbon dioxide of greater than 4:1; (iii) introducing biogenic carbon dioxide from step (i) and hydrogen from step (ii) together or separately to a fermentation reactor; and (iv) forming additional biogenic ethanol by converting the biogenic carbon dioxide and hydrogen in the reactor to biogenic ethanol by fermentation with a microorganism.

In one embodiment, there is provided a process for increasing biogenic ethanol production from non-fossil organic material comprising: (i) providing biogenic carbon dioxide that is sourced from an ethanol production process comprising producing biogenic ethanol from a fermentation of the non-fossil organic material, wherein biogenic carbon dioxide is generated during the ethanol production process and collected; (ii) providing a stream enriched in hydrogen that is sourced from a hydrogen production process comprising the steps of: (a) converting fossil methane to carbon monoxide and hydrogen by reforming; (b) converting at least a portion of the carbon monoxide by a water-gas shift reaction to produce a stream comprising fossil carbon dioxide and hydrogen; and (e) separating at least a portion of the hydrogen from said stream to produce the stream enriched in hydrogen; (iii) introducing biogenic carbon dioxide from step (i) and hydrogen produced in step (ii)(c) together or separately to a fermentation reactor; and (iv) forming additional biogenic ethanol by converting the biogenic carbon dioxide and hydrogen in the reactor to ethanol by fermentation with a microorganism.

According to one embodiment, there is provided a process for producing a biogenic carbon-based fuel, fuel intermediate or chemical product comprising: (i) providing biogenic carbon dioxide that is sourced from a production process using non-fossil organic material as a feedstock; (ii) providing a stream comprising hydrogen by converting fossil methane to carbon monoxide and hydrogen by reforming; (iii) converting the biogenic carbon dioxide from step (i) and hydrogen produced in step (ii) to the biogenic carbon-based fuel, fuel intermediate or chemical product; (iv) obtaining a process stream comprising organic components from (a) the production process of step (i); (b) one or more stages of a process comprising step (iii); or (c) a combination thereof, and carrying out anaerobic digestion of the process stream to produce a crude biogas; and (v) generating or causing the generation of a fuel credit with respect to the use of methane sourced from biogas produced in step (i), (iv), or both steps as a transportation or heating fuel.

According to one embodiment, there is provided a process for producing a biogenic carbon-based fuel, fuel intermediate or chemical product comprising: (i) providing biogenic carbon dioxide that is sourced from a production process using non-fossil organic material as a feedstock; (ii) providing a stream comprising hydrogen by converting fossil methane to carbon monoxide and hydrogen by reforming; (iii) converting the biogenic carbon dioxide from step (i) and hydrogen produced in step (ii) to the biogenic carbon-based fuel, fuel intermediate or chemical product; and (iv) using heat from the reforming as process energy (a) in the production process of step (i); (b) in one or more stages of a process comprising step (iii) to produce the biogenic carbon-based fuel, fuel intermediate or chemical product; or (c) a combination thereof.

According to one embodiment, there is provided a process for producing a biogenic carbon-based fuel, fuel intermediate or chemical product comprising: (i) providing biogenic carbon dioxide that is sourced from non-fossil organic material; (ii) providing a stream comprising hydrogen by converting fossil methane to carbon monoxide and hydrogen by reforming; (iii) converting the biogenic carbon dioxide from step (i) and hydrogen produced in step (ii) to the biogenic carbon-based fuel, fuel intermediate or chemical product; (iv) carrying out anaerobic digestion of a process stream comprising organic components to produce a crude biogas comprising biogenic carbon dioxide; (v) removing at least a portion of the biogenic carbon dioxide from the crude biogas to produce a stream comprising additional biogenic carbon dioxide; and (vi) introducing said additional biogenic carbon dioxide removed from the crude biogas to step (iii), step (i) or both steps.

According to one embodiment, there is provided a process for producing a biogenic carbon-based fuel, fuel intermediate or chemical product comprising: (i) providing biogenic carbon dioxide that is sourced from non-fossil organic material; (ii) providing a stream comprising hydrogen by converting fossil methane to carbon monoxide and hydrogen by reforming; (iii) fermenting the biogenic carbon dioxide from step (i) and hydrogen produced in step (ii) to a biogenic carbon-based fuel, fuel intermediate or chemical product; (iv) carrying out anaerobic digestion on a stream produced from the process comprising organic components to produce biogas; (v) obtaining a byproduct from step (iii) of fermenting; and (vi) introducing the byproduct to the anaerobic digestion of step (iv).

According to one embodiment, there is provided a process for producing a fuel or fuel intermediate comprising: pretreating a feedstock; fermenting at least a portion of the pretreated feedstock to provide a fermentation product; distilling the fermentation product to provide an alcohol; converting a second portion of the feedstock to crude biogas; converting the crude biogas to acetic acid; and converting the acetic acid to ethanol.

BRIEF DESCRIPTION OF THE FIGURES

Exemplary embodiments will now be described in conjunction with the drawings in which.

DETAILED DESCRIPTION

Non-fossil Organic Material

Figure 1:
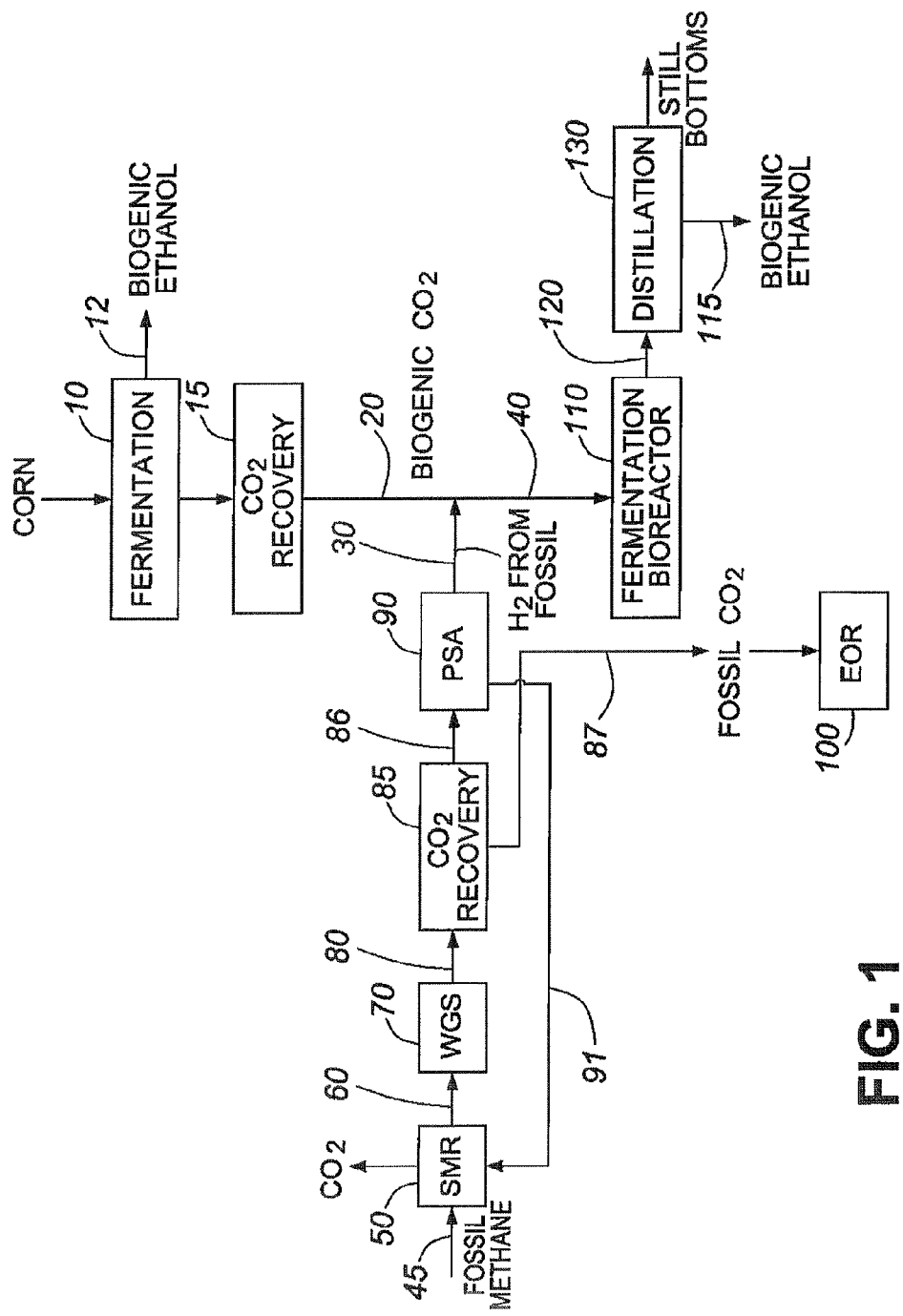
FIG. 1 is a process flow diagram showing the production of biogenic ethanol using fossil derived hydrogen and biogenic carbon dioxide in a process in which fossil carbon dioxide from hydrogen production is introduced underground.

In various embodiments the processes described herein produce a first energy product or a biogenic carbon-based product selected from a chemical product, a fuel and/or a fuel intermediate and carbon dioxide from non-fossil organic material.

The term "biogenic carbon-based" in reference to a product, such as a fuel, fuel intermediate or a chemical product, means that the product comprises carbon that is sourced directly or indirectly from non-fossil organic material. This can include carbon derived from fossil carbon dioxide, or from both fossil and non-fossil carbon dioxide, but that is considered biogenic by those skilled in the art, as described further herein.

As used herein, the term "non-fossil organic material" or simply "organic material" refers to a material comprising carbon from one or more biologic sources that is not obtained from underground geologic formations. Any suitable non-fossil, biologic source material obtained or derived directly or indirectly from plants or animals can be used as the organic material in various embodiments of the process to provide a carbon and/or energy source. This includes plant derived organic material comprising polysaccharides, including starch, cellulose and hemicellulose, oligosaccharides, disaccharides, monosaccharides, or a combination thereof. Other biologic, non-fossil source material that can be utilized as a carbon and/or energy source includes compounds or molecules derived from non-sugar containing material, such as lignin and fats. The organic material may be in liquid form containing soluble components, solid form, gaseous form, or any combination thereof.

According to one embodiment, the organic material includes material comprising starches, sugars or other carbohydrates derived from sugar or starch crops. The sugar or starch crops may include, but are not limited to, corn, wheat, barley, rye, sorghum, rice, potato, cassava, sugar beet, sugar cane, or a combination thereof.

The non-fossil organic material may also be biomass or biomass derived material. Examples of biomass and biomass derived material include (i) energy crops; (ii) residues, byproducts or waste from the processing of plant material in a facility, or feedstock derived therefrom; (iii) agricultural residues; (iv) forestry material; (v) material derived from pulp and paper processing; (vi) pulp and paper residues; and (vii) municipal waste or components removed or derived from municipal waste. The biomass or biomass derived material can be in any form, including solid, liquid, gaseous form or a combination thereof.

Energy crops include biomass crops such as grasses, including C4 grasses, such as switch grass, energy cane, sorghum, cord grass, rye grass, miscanthus, reed canary grass, C3 grasses such as *Arondo donax* or a combination thereof.

Residues, byproducts or waste from the processing of plant material in a facility or feedstock derived therefrom include residues remaining after obtaining sugar from plant biomass such as sugar cane bagasse, sugar cane tops and/or leaves, beet pulp, or residues remaining after removing sugar from Jerusalem artichoke or residues remaining after grain processing, such as corn fiber, corn stover or bran from grains. Agricultural residues include, but are not limited to, soybean stover, corn stover, rice straw, sugar cane tops and/or leaves, rice hulls, barley straw, corn cobs, wheat straw, canola straw, oat straw, oat hulls, or corn cobs.

Forestry material includes any species of hardwood or softwood. The term includes residues, byproducts, waste or non-waste material from processing any hardwood or softwood species. Examples of waste include residues from sawmills, trimmings or slash from logging operations. Pulp and paper residue, includes non-pulp and non-paper products from chemical pulping or paper making such as black liquor, spent sulfite liquor, sludge, broke, fines or precipitated lignin.

Municipal waste includes post-consumer material or waste from a variety of sources, such as domestic, commercial, institutional and industrial sources. For example, the term includes refuse from waste collection, raw sewage and sewage sludge.

Biomass or biomass derived material can be a mixture of fibers that originate from different kinds of plant material, including mixtures of cellulosic and non-cellulosic biomass. In addition, the biomass may comprise fresh biomass, partially dried biomass, fully dried biomass, or a combination thereof. Moreover, new biomass varieties may be produced from any of those listed above by plant breeding or by genetic engineering.

First Energy Product or Biogenic Carbon-based Product

Certain embodiments of the invention comprise producing or causing one or more parties to produce a first product that is derived or sourced from non-fossil organic material. The first product is selected from (a) an energy product; and (b) a biogenic carbon-based product selected from a fuel, fuel intermediate and a chemical product. The fuel or fuel intermediate is also referred to herein as a biofuel or biofuel intermediate, respectively.

As used herein, an "energy product" is (i) any product that is used to generate electrical energy or heat, such as lignin or methane; or (ii) products that store heat energy or electrical energy including steam and electricity produced by combusting non-fossil organic material.

A "fuel" includes liquid or gaseous material, which may contain carbon, that can be combusted to produce power or heat and includes both transportation and heating fuel. The fuel may be a liquid at 20° C., such as an alcohol, or a gaseous fuel, such as methane or hydrogen, which are gases at this temperature. The fuel may exist in any form, including gaseous, liquid or compressed form.

A "fuel intermediate" is a precursor used to produce a fuel by a further conversion process, such as by a biologic conversion, a chemical conversion, or a combination thereof.

A "chemical product" is a chemical compound used in a production process or a product such as a commodity. Some examples of chemical products produced from non-fossil organic material are sugar acids, sugar alcohols, organic acids, bioplastic or bioplastic intermediates, fermentation-derived chemicals, fertilizer and lignin-based products. A "lignin-based product" is a product that comprises lignin, a lignin derivative, or a product that is produced from lignin.

Some examples of fuels, fuel intermediates, chemical and energy products, and processes for their production from non-fossil organic material are described below. Such processes include fermentation to produce liquid or gaseous fermentation products, or thermal processes, including combustion, gasification, pyrolysis or a combination thereof.

Fermentation

The fuel, fuel intermediate and/or chemical product may be produced by fermentation using any of a number of known processes that use bacteria, yeast or other microorganisms. As used herein, "fermentation" includes the biologic conversion of non-fossil organic material by any process using microbes in one or more stages. Such term includes the fermentation of non-fossil organic material in any form, including solid, liquid or gaseous forms, or any combination thereof. In addition to producing a fuel, fuel intermediate or chemical product, processes comprising fermentation can generate one or more energy products such as lignin, methane, steam or electricity for external use.

Carbon dioxide is often generated during the fermentation and may be collected using known processes as discussed further herein. For example, in the production of ethanol, the fermentation of glucose produces two molecules of carbon dioxide by the following reaction:

$$C_6H_{12}O_6 \rightarrow 2C_2H_6O \rightarrow 2CO_2.$$

Prior to fermentation, the non-fossil organic material may be processed by mechanical, chemical, thermal and/or biologic processes to improve its ability to be fermented. In some embodiments of the invention, the non-fossil organic material is a sugar or starch crop. For a sugar crop, the non-fossil organic material is typically processed to extract sugar therefrom. The sugar is subsequently fermented to produce the fuel, fuel intermediate or chemical product. Sugar crops, including, but not limited to, sugar cane, sugar beets or sweet sorghum, may be subjected to a mechanical treatment, such as crushing and/or pressing, to extract the sugar from the plants. For example, sucrose from sugar cane can be extracted using roller mills. Sugar from sweet sorghum stalks can be extracted in a similar manner, although certain varieties of sorghum contain grain that can be processed using technology employed for processing starch crops as described below.

Starch crops, which include cereal crops, may be subjected to size reduction, such as by milling or grinding. The starch may be subsequently hydrolyzed with enzymes, by chemical treatment, or a combination of these treatments. By way of example, grain may be milled with a roller or hammer mill, followed by the addition of water and hydrolysis of the starch with amylases to produce fermentable sugar. This method is commonly referred to as "dry milling". An alternative method is "wet milling" in which the grain is steeped, such as in an acidic solution and/or a solution containing enzymes, and then subjected to size reduction, such as milling, to facilitate separation of the starch from the other components of the grain. The starch is subsequently hydrolyzed to sugar using methods described above.

Sugar for fermentation can also be obtained from processes that convert the cellulose and hemicellulose portion of plant material to the fuel, fuel intermediate or chemical product. Processing may include pretreating a biomass or biomass derived material to disrupt fiber structure. Pretreatment can be with heat, mechanical processing, addition of one or more chemicals, biocatalysts, or combinations thereof to release sugars. After pretreatment, between 30 wt % and 100 wt % of the xylan from the hemicellulose may be hydrolyzed, although, during some pretreatments, there may be limited xylan hydrolysis. After pretreatment, between 10 wt % and 100 wt % of the lignin may remain insoluble. The lignin may be used to generate an energy product or chemical product, as set forth below.

Non-limiting examples of pretreatment include acid pretreatment, alkali pretreatment and hydrothermal pretreatment. Such pretreatment processes are set forth in U.S. Application No. 61/948,726 filed Mar. 6, 2014, which is incorporated herein by reference.

The pretreatment may improve the accessibility of cellulose to a subsequent enzymatic or chemical hydrolysis to convert cellulose to glucose. The enzymatic hydrolysis may involve the addition of enzymes including cellulases and hemicellulases. Other enzymes that may be used include amylases, glucanases, proteases, lipases, pectinases, laccases, phytases or combinations thereof. The glucose may then be converted to the fuel, fuel intermediate or chemical product.

In some embodiments, the fermentation process produces liquid fuels, fuel intermediates or chemical products. Such liquid products include fuels or fuel intermediates including alcohols, such as ethanol, propanol, butanol and isobutanol. For ethanol production, the fermentation can be carried out with a yeast or a bacterial strain, such as a *Saccharomyces* spp. or *Zymomonas mobilis* strain. Butanol may be produced from glucose by a microorganism such as *Clostridium acetobutylicum* and then concentrated by distillation. The alcohol may then be distilled to obtain a concentrated ethanol solution.

Xylose, arabinose and other sugars that are derived from the hemicelluloses may also be fermented to fuels, fuel intermediates or chemical products. An example of a fuel is ethanol, which can be produced by a yeast strain that naturally contains, or has been engineered to contain, the ability to ferment these sugars to ethanol. Non-limiting examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (see for example U.S. Pat. Nos. 5,789,210, 5,866, 382, 6,582,944 and 7,527,927 and European Patent No. 450530) or (b) fungal or bacterial xylose isomerase (XI) gene (see for example U.S. Pat. Nos. 6,475,768 and 7,622, 284). Examples of yeasts that have been genetically modified to ferment L-arabinose include, but are not limited to, recombinant *Saccharomyces* strains into which genes from either fungal (see for example U.S. Pat. No. 7,527,951) or bacterial (see for example WO 2008/041840) arabinose metabolic pathways have been inserted.

Although examples of fuels and fuel intermediates are provided, embodiments of the present invention also encompass the production of chemical products from the fermentation of organic material. Examples of chemical products that can be produced by fermentation include sugar acids including xylonic acid and arabonic acid; sugar alcohols including xylitol, arabitol, erythritol, galactitol and mannitol; and organic acids including adipic acid, citric acid, malic acid, succinic acid, pyruvic acid, acetic acid, itaconoic acid and lactic acid; biooils including sesquiturpenes such as farnesene; diols, including butanediol and 1,3 propanediol; alcohols, such as propanol; and ketones, including acetone. Examples of processes for producing such chemical products by fermentation from organic material are set forth in U.S. Publication No. 2012/0231514 (published Sep. 13, 2012).

During the production of a fuel, fuel intermediate and/or chemical product from biomass or biomass derived material, a non-sugar containing component that remains after the conversion, known as lignin, can be combusted to generate an energy product including heat or power. Such combustion processes are discussed further below. The energy product produced from the lignin can be used to displace fossil energy by use within the production process itself, or by exporting the energy product, such as to supply energy in the form of electricity to the grid. Recovered lignin may also be utilized for making a chemical product, such as lignin-based product. The lignin-based product may be an additive in a commercial application, a dispersant, a binder or an adhesive. An example of a conversion process is heating lignin at elevated temperature in a gasification or pyrolysis to produce aromatic compounds such as phenols.

Although the fermentation of organic material in the form of sugar is described, the fermentation may also involve the conversion of organic material in the form of a gaseous stream to a fuel, fuel intermediate and/or chemical product. A non-limiting example of such a fermentation is the production of ethanol from syngas, examples of which are described in more detail herein. These processes may produce carbon dioxide that can be collected and/or used to produce a fuel or fuel intermediate.

The fermentation may also be an anaerobic digestion, which is the biologic breakdown of non-fossil organic material by microorganisms generally under low oxygen conditions, or in the absence of oxygen, to produce gases. Prior to anaerobic digestion, the non-fossil organic material is optionally processed by mechanical, chemical, thermal and/or biologic processes to improve its ability to be fermented. Biologic processes include treatment with enzymes including cellulases, hemicellulases, amylases, glucanases, proteases, lipases, pectinases, laccases, phytases or combinations thereof.

The gases produced by anaerobic digestion of non-fossil organic material include methane, biogenic carbon dioxide and hydrogen sulfide. As would be appreciated by those skilled in the art, anaerobic digestion may involve the decomposition of non-fossil organic material, including carbohydrates, fats and proteins therein, into simple sugars and glycerol. These compounds are then converted to acids, which are subsequently converted into methane by methanogenic bacteria or other microorganisms, typically by the following reaction:

$$C_6H_2O_6 \rightarrow 3CH_4 + 3CO_2.$$

The gases from anaerobic digestion, also referred to herein as "crude biogas" or simply as "biogas", include methane, carbon dioxide and typically one or more impurities. Generally, after collection of carbon dioxide, and removal of one or more impurities, the methane can be used as compressed natural gas or liquid natural gas to power vehicles or used for heating. Alternatively, the methane from biogas can be used to produce another fuel, fuel intermediate and/or chemical product.

The methane from biogas may be introduced to an apparatus for transporting methane, such as a pipeline. In one embodiment, the pipeline is part of a pipeline system/network (e.g., the pipeline may be connected to one or more other connected pipelines). Methane may then be withdrawn from the apparatus for use as a transportation or heating fuel or for use in the production of another fuel or fuel intermediate. Government authorities have recognized that it does not make any difference, in terms of the beneficial environmental attributes associated with the use of biogas, whether the displacement of fossil fuel occurs in a fungible natural gas pipeline, or through the use of the biogas itself as a transportation or heating fuel. Thus, when a fuel such as methane is obtained from biogas, and transported (such as via a natural gas pipeline), a corresponding amount of withdrawn fuel (such as methane) is considered renewably derived or to have the GHG emission attributes of the biogas introduced to the pipeline, even if the molecules therein are fossil derived. Thus, for example, methane obtained directly from biogas or fossil methane qualifying as renewable is referred to herein as "methane sourced from biogas".

In one embodiment, a fuel credit is generated, or caused to be generated, with respect to the use of the methane sourced from biogas as a transportation fuel and/or for heat/energy. In another embodiment, a fuel credit is generated, or caused to be generated, with respect to the use of the methane in generating a fuel for use as a transportation or heating fuel. For example, a renewable fuel credit may be generated for biogenic methane and/or ethanol, and/or fuels derived therefrom.

Fuels or fuel intermediates produced directly or indirectly from methane sourced from biogas include syngas, hydrogen, and/or liquid hydrocarbons. Syngas, which comprises hydrogen, carbon monoxide and optionally other gaseous components, including carbon dioxide, can be used as a fuel itself or more typically as an intermediate to produce another fuel or fuel intermediate. Syngas can be produced from methane sourced from biogas by steam methane reforming by the following reaction:

$$CH_4 + H_2O \rightarrow CO + 3H_2.$$

Syngas can also be produced by thermal processing as described below. The use of syngas to produce other fuels or fuel intermediates is described below.

In certain embodiments, hydrogen is produced from methane sourced from biogas. Renewable hydrogen may be produced from the methane by steam methane reforming, typically followed by a water gas shift (WGS) reaction. Those skilled in the art understand that a WGS reaction involves the chemical reaction of carbon monoxide and water vapor to form carbon dioxide and hydrogen. After production, such hydrogen may be used in a process to produce a liquid transportation or heating fuel. For example, the renewable hydrogen may be combined with a crude oil derived liquid hydrocarbon in a hydrogen addition step in a fuel production facility, such as an oil refinery, so that it becomes incorporated into the hydrocarbon and ultimately becomes part of a fuel that is the product of the facility. Examples of such processes are set forth in U.S. Pat. Nos. 8,658,026 and 8,753,854 which are incorporated herein by reference in their entireties and particularly for the purpose of describing such processes. In one embodiment, the renewable hydrogen used in the foregoing process may include hydrogen from methane sourced from biomass considered renewable by regulators.

Thermal Process

The non-fossil organic material may be subjected to a thermal process to produce a fuel, fuel intermediate, chemical product and/or an energy product. The thermal process may include combustion, gasification, pyrolysis or a combination thereof. An energy product may be produced by combustion of the non-fossil organic material, while a fuel, fuel intermediate or chemical product may be produced by gasification or pyrolysis. Some examples of fuels, fuel intermediates or chemical products produced from the gasification or pyrolysis of non-fossil organic material include syngas, hydrogen, methane, liquid hydrocarbons, pyrolysis oil and ammonia. Some examples of combustion, gasification and pyrolysis, and products generated from these processes, are described in more detail below.

Combustion includes one or more exothermic reactions between the non-fossil organic material and an oxidant, which is typically air or oxygen. Combustion of the non-fossil organic material can be conducted in a power plant. In such embodiments, carbon dioxide is recovered from a gas stream, known in the art as "flue gas".

The combustion may be carried out with a gas having an oxygen content exceeding that of air, known in the art as an "oxyfuel combustion process". In certain embodiments, the flue gas may be re-circulated to the combustion and mixed with an oxygen stream as part of the oxyfuel combustion process. An advantage of oxyfuel combustion processes is that combusting in the presence of oxygen removes contaminants. The result is a flue gas having a high concentration of carbon dioxide, which may be collected with relative ease.

In one embodiment, the non-fossil organic material is combusted to produce an energy product. Typically, the non-fossil organic material that is combusted is biomass or biomass derived material. An example of a biomass derived material suitable for combustion is lignin or a stream that comprises lignin as a constituent. For example, in one embodiment lignin is provided as a pellet for fuel. Lignin differs from cellulose and hemicellulose in that it is not composed of sugar units, but rather phenolic-propane units. Although lignin does not yield any fermentable sugars, it may be combusted to generate heat or electricity.

The non-fossil organic material may be fed to a combustion apparatus, such as a steam boiler and the heat generated utilized to produce electricity, steam, process heat, building heat, or any combination of thereof. The boiler generally includes a section in which water or other fluid is heated. The heat produced from the burning of organic material may be transferred to boiler feed water to produce steam. The boiler may be a fluidized bed boiler, although other types of boilers may be used as required. The feed to the boiler may also include biogas produced during anaerobic digestion. Moreover, during the start-up stage of the process, a small amount of natural gas may be added to the boiler to heat the fuel to the ignition point. Depending on the emissions regulations, exhaust from the boiler may be passed to a scrubber or other series of operations to reduce pollutant levels before being discharged to the environment. As well, particulate matter may need to be removed from the exhaust. Ash from the boiler may be landfilled or sold as a co-product depending on its composition.

The steam may be used to drive turbines to create electricity for sale to the power grid and/or to meet plant needs. Alternatively, or in addition to electricity generation, the steam can be used to supply process heat needs within a plant. If the steam is used within a plant, the pressure may be reduced prior to its re-use in the process. Furthermore, the steam can be utilized to provide building heating.

While combustion produces an energy product, gasification is typically carried out to produce syngas. Gasification includes heating at elevated temperature, generally in the presence of oxygen. Gasification of biomass or biomass derived products can be carried out by the following reaction:

$$8CH_2O+O_2 \rightarrow 6CO+2CO_2+8H_2.$$

The carbon dioxide produced by the above reaction can be collected as set out below. The syngas can, in turn, be used as an intermediate to produce another fuel or fuel intermediate, as set forth previously, or used as a fuel itself. Examples of products made directly or indirectly from syngas include liquid hydrocarbons, methane, hydrogen, methanol and ethanol. Processes for their production from syngas are described above.

Biogenic carbon dioxide can be collected from one or more stages of a gasification process or downstream stages, such as product synthesis processes and converted to the second biogenic carbon-based fuel or fuel intermediate as described below. Without being limiting, the biogenic carbon dioxide may be collected from a waste gas stream that remains after combustion of a gas stream containing both combustible gases and carbon dioxide. Burning of the combustible gases in the mixture forms carbon dioxide and the resulting stream enriched in carbon dioxide can subsequently be used to make the biogenic carbon-based fuel or fuel intermediate. Biogenic carbon dioxide may also be separated and recovered from syngas. Further, during a syngas fermentation, which is described further below, carbon dioxide generated during the fermentation can be collected and used for production of the fuel or fuel intermediate. Carbon dioxide can also be collected from a stream resulting from subjecting syngas to a water gas shift reaction, as follows:

$$CO+H_2O \rightarrow CO_2+H_2.$$

One or more of the above-mentioned streams produced from the gasification or product synthesis to fuel can be combined and then used for additional fuel or fuel intermediate production.

Pyrolysis includes heating non-fossil organic material at elevated temperature to produce syngas, char and/or pyrolysis oil and may be carried out in the absence of oxygen or at low levels thereof. Carbon dioxide can be collected from a stream resulting from a water gas shift reaction carried out on the syngas or other streams generated during the process that contain carbon dioxide. Pyrolysis oil, also referred to as bio-oil, is produced by subjecting the non-fossil organic material to pyrolysis at elevated temperature, typically lower than gasification. Pyrolysis oil can be treated further to produce a transportation fuel such as diesel or used directly as a fuel.

Producing Fuels from Fuel Intermediates

In one embodiment, fuels are produced from fuel intermediates, such as syngas. As described above, syngas can originate from a variety of different processes, including gasification, pyrolysis or produced from methane sourced from biogas. Examples of products made directly or indirectly from syngas include liquid hydrocarbons, methane, hydrogen, methanol, ethanol and/or ammonia.

The production of liquid hydrocarbons from syngas may be advantageous in that they can replace petroleum products such as diesel or gasoline. Hydrocarbons can be produced by a Fischer Tropsch process which uses a catalyst to convert carbon monoxide in syngas to hydrocarbons, such as alkanes, although other reaction products may result as well.

In one embodiment, methane is produced from syngas. The production of methane from syngas includes a methanation reaction, which is conducted over metal catalysts at elevated temperature and pressure. The chemical reaction for producing methane from syngas is as follows:

$$CO+3H_2 \rightarrow CH_4+H_2O.$$

In another embodiment, methane is produced from carbon dioxide and hydrogen present in syngas by the following reaction:

$$CO_2+4H_2 \rightarrow CH_4+2H_2O.$$

Renewable hydrogen can also be produced by syngas by subjecting the syngas to a water gas shift reaction, as follows:

$$CO+H_2O \rightarrow CO_2+H_2.$$

The renewable hydrogen can be used directly as a transportation fuel or used in a fuel production process to produce a hydrocarbon fuel, for example as described in U.S. Pat. Nos. 8,658,026 and 8,753,854.

Another product that can be produced from syngas is methanol. The reaction is as follows:

$$CO+2H_2 \rightarrow CH_3OH.$$

As would be appreciated by those of skill in the art, generally carbon dioxide is added to the syngas or a certain amount of carbon dioxide is left in the syngas to maintain a suitable reaction stoichiometry for optimal methanol production. The methanol produced from this reaction can be converted to ethanol or other fuels through a variety of different chemical or biological conversion routes, representative examples of which are described further below.

Collecting Biogenic Carbon Dioxide

As mentioned, biogenic carbon dioxide may be generated during the production of the first energy product or biogenic carbon-based product. Those skilled in the art will appreciate that the biogenic carbon dioxide can be sourced directly from a production process using non-fossil organic material as a feedstock or it can be fossil carbon dioxide, or a mixture of fossil and non-fossil carbon dioxide that is sourced more indirectly from such organic material. Thus, "biogenic carbon dioxide" as used herein includes carbon dioxide that is (a) obtained from a production process using non-fossil organic material as a feedstock; (b) withdrawn from an apparatus for transporting carbon dioxide, which withdrawn carbon dioxide is from fossil sources or contains a mixture of carbon dioxide from fossil and non-fossil sources and that is considered renewable due to the introduction of an amount of carbon dioxide produced by such production process to the apparatus that corresponds to the amount of carbon dioxide withdrawn; or both (a) and (b).

In one embodiment, the biogenic carbon dioxide generated during the production of the first energy product of biogenic carbon-based product is "collected", by which it is meant any suitable process for obtaining carbon dioxide during or after its generation, and may include single or multi-stage processes. The biogenic carbon dioxide may be collected along with other non-$CO_2$ components. That is, collection of carbon dioxide may comprise obtaining a stream comprising biogenic carbon dioxide and optionally one or more non-$CO_2$ components. To illustrate, collecting a crude biogas stream, from a landfill or a digester, comprising carbon dioxide along with other components such as methane and hydrogen resulting from anaerobic digestion constitutes collection of biogenic carbon dioxide. To further illustrate, collecting carbon dioxide may comprise obtaining a stream comprising carbon dioxide enriched by recycle.

The biogenic carbon dioxide may be enriched by purification, recycle or the like. The purification may, for instance, include a process in which carbon dioxide is separated from other constituents in a stream or other processes that produce a stream enriched in carbon dioxide. Such other processes include combusting a carbon dioxide-containing stream comprising combustible carbon to produce a stream comprising additional carbon dioxide resulting from the combustion. Recycling of a stream comprising carbon dioxide may result in enrichment of carbon dioxide as well due to the increase in concentration of carbon dioxide during re-circulation. A stream enriched in biogenic carbon dioxide may also be a waste stream generated during the process.

The $CO_2$-enriched stream may comprise at least 60%, at least 70%, at least 80%, or at least 90% carbon dioxide by weight.

In certain non-limiting embodiments, the level of carbon dioxide recovery from a gaseous or liquified mixture may be at least 40% by weight, at least 50% by weight, at least 60% by weight, at least 70% by weight, at least 80% by weight, at least 90% by weight or at least 95% by weight.

Non-limiting examples of known collection methods include separating biogenic carbon dioxide from a gaseous mixture with a liquid absorbent or solid sorbent, membrane separation or separation of carbon dioxide from other constituents in liquid form. Carbon dioxide can be separated from impurities in a gas stream using a liquid absorbent, such as a solvent or solid sorbent that is capable of capturing carbon dioxide. After capturing carbon dioxide, the liquid absorbent or solid sorbent is regenerated to release the carbon dioxide. The liquid absorbent or solid sorbent can subsequently be used to capture more carbon dioxide. A solid sorbent includes minerals, zeolites and activated carbon. Membranes are materials that allow the selective permeation of a gas through them. Membrane materials may be polymeric, metallic or ceramic and the selectivity of the membrane for the gaseous constituents depends on nature of the material of which it is made.

Separation of carbon dioxide from other constituents in liquid form may involve liquifying a gas comprising carbon dioxide by compression, cooling and expansion steps. When in liquid form, the carbon dioxide can be separated by distillation. Refrigerated systems may also be used for carbon dioxide separation.

A number of specific techniques for obtaining carbon dioxide from various gaseous streams resulting from fermentation, gasification, pyrolysis or combustion are described below. However, it will be understood by those having ordinary skill in the art that other methods of recovering biogenic carbon dioxide, as would be known to those skilled in the art, are also within the scope of the invention.

Known techniques for collecting carbon dioxide from fermentations include the use of liquid absorbents. For example carbon dioxide can be recovered using a scrubbing unit in which water is flowed counter-current to the carbon dioxide-containing stream to remove water and water soluble components, including the fermentation product. Water that remains in the carbon dioxide is subsequently removed in a compressor to increase the pressure of the carbon dioxide up to the water condensation level. The carbon dioxide may be fed to a drying unit to remove additional water. A purifying unit, which typically contains activated carbon, may be included in the process configuration before or after the drying unit to remove impurities. Inert gases, such as nitrogen (also referred to in the art as non-condensable or permanent gases), may subsequently be removed in a condenser.

Carbon dioxide can be recovered from crude syngas produced from gasification or from a stream resulting from reacting the carbon monoxide with steam in a water gas shift reaction to produce a stream comprising carbon dioxide and hydrogen. Further, the biogenic carbon dioxide may be collected from excess carbon dioxide generated during the gasification or collected from a recycle stream, such as, without limitation, a carbon dioxide stream recycled during syngas fermentation.

Without being limiting, the carbon dioxide can be separated by physical or chemical absorption to produce a carbon dioxide-containing stream. The physical absorption may involve the use of membranes that allow the selective permeation of a gas through them. For example, the carbon dioxide can be recovered by membranes that are more permeable to carbon dioxide than other components in the carbon dioxide-containing stream. The carbon dioxide passes through the membrane while other components do not, thereby resulting in a stream that is carbon dioxide enriched. The carbon dioxide-enriched stream can be used in gas or liquid form. Chemical absorption involves the use of chemical solvents. Examples of chemical solvents include methanol, N-methyl-2-pyrolidone, dimethyl ethers of polyethylene glycol, potassium carbonate, monoethanolamine, methyldiethylamine and tetrahydrothiophene 1,1-dioxide. A known method for recovering carbon dioxide from a stream comprising carbon dioxide and hydrogen resulting from a water gas shift reaction is a Rectisol® wash process that uses methanol as a solvent. Amine gas scrubbing is another example of a technique involving chemical absorption. A prevalent amine for such applications in monethanolamine.

Carbon dioxide can be obtained from a gaseous stream, such as a flue gas stream produced from a combustion process that uses the non-fossil organic material as a feed. This includes combustion of organic material in a power plant, such as a plant that otherwise burns fossil fuel such as natural gas or coal. Such a combustion includes an oxyfuel combustion process.

Gaseous streams from combustion contain carbon dioxide and other impurities depending on the source. Carbon dioxide can be separated from impurities in the gas stream using a liquid absorbent or solid sorbent that is capable of capturing carbon dioxide. The liquid absorbent may be a chemical solvent, such as an amine, or a Selexol™ solvent which uses polyethylene glycol as a solvent. The liquid absorbent can be added as part of a scrubbing operation, such as amine scrubbing. Regeneration of the chemical solvent may then be conducted by stripping or other separation techniques, with the regenerated chemical solvent being used to capture more carbon dioxide. A solid sorbent may include a zeolite or activated carbon. For solid sorbents, regeneration may be achieved by a change in pressure or temperature, thereby releasing the carbon dioxide and regenerating the sorbent for further use.

Biogenic carbon dioxide from oxyfuel combustion can be separated from other gaseous components by distillation. A carbon dioxide-containing stream can be liquefied by compression, cooling and expansion steps. The carbon dioxide can subsequently be separated in liquid form in a distillation column. A further example of a technique for carbon dioxide separation from other components is refrigerated separation. Distillation or refrigerated separation can also be used to separate carbon dioxide from synthesis gas that has undergone a water-gas shift conversion of carbon monoxide to carbon dioxide.

The biogenic carbon dioxide may be collected from two or more separate steps of a process to convert the organic material to a fuel, fuel intermediate or energy product. To illustrate, carbon dioxide may be collected from a fermentation of organic material to produce a liquid fuel, such as an alcohol. In addition, carbon dioxide may be recovered from an anaerobic digestion or gasification of a waste stream generated from such liquid fuel fermentation. By collecting carbon dioxide from two or more steps of the same or different processes, the yield of the fuel, fuel intermediate, chemical product or energy product from the organic material can be further increased.

Figure 4:
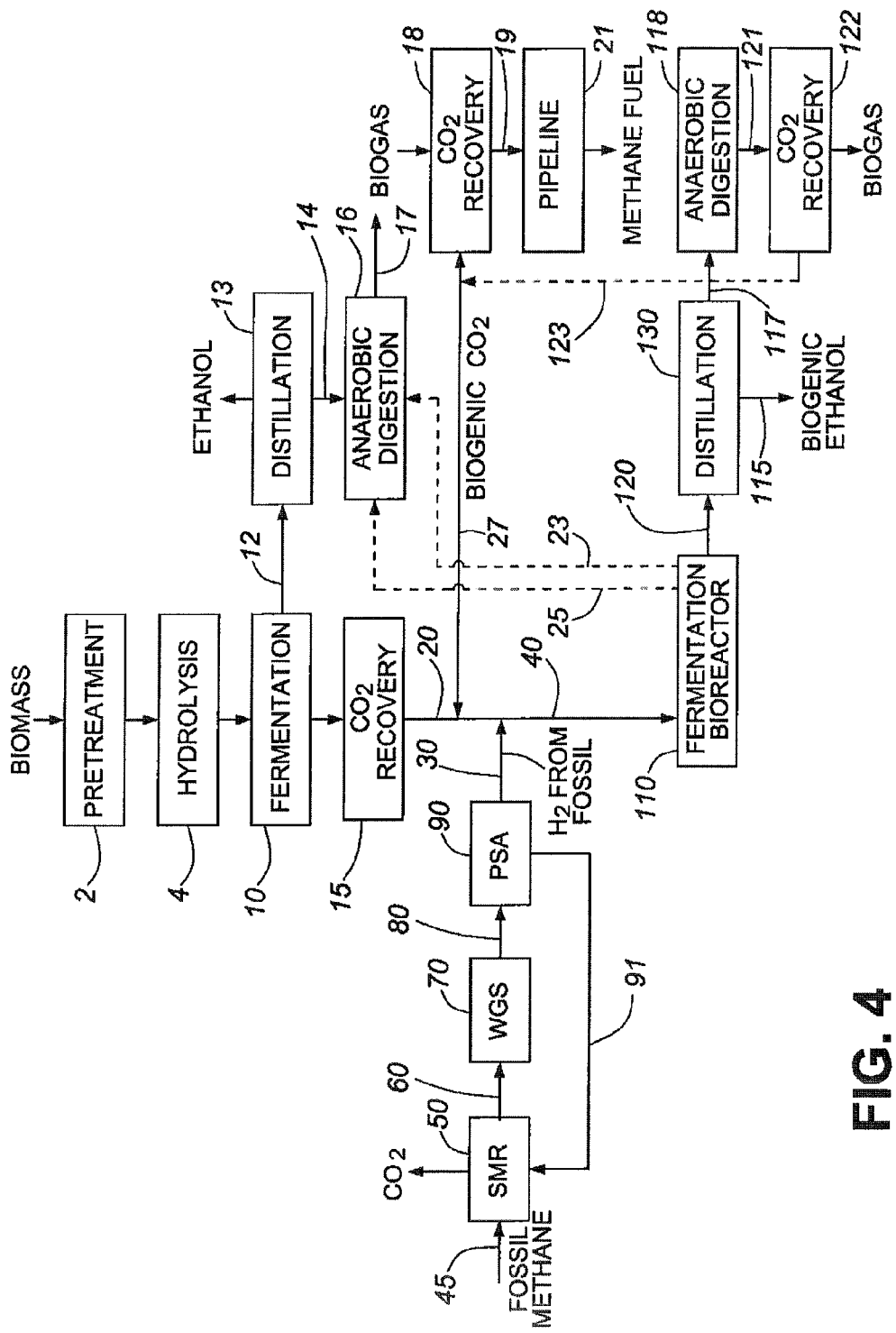
FIG. 4 is a process flow diagram showing the production of biogenic ethanol from the gaseous fermentation of fossil derived hydrogen and biogenic carbon dioxide in a process in which the biogenic carbon dioxide is recovered from the fermentation of sugar to ethanol and from anaerobic digestion of a still bottoms stream and in which the biogenic carbon dioxide recovered from both sources is fed to the gaseous fermentation.

A non-limiting example of such a process is shown in FIG. 4. In the process depicted, ethanol is produced from fermenting sugar originating from a biomass feedstock to produce a fermented solution comprising ethanol. Carbon dioxide produced during the fermentation is collected. A waste stream remaining after distillation of the fermented solution to concentrate ethanol is treated by anaerobic digestion, which produces biogas comprising carbon dioxide and at least a portion of the carbon dioxide is recovered from the biogas. Both the biogenic carbon dioxide from the sugar fermentation to produce ethanol and from the anaerobic digestion are combined with fossil derived hydrogen. The combined gaseous stream is subsequently fermented to produce a fermented solution comprising a fermentation product such as ethanol. If ethanol is the product, the fermented solution may be distilled to concentrate the ethanol. A waste stream remaining after distillation of the fermented solution to concentrate ethanol may also be treated by anaerobic digestion, which produces biogas comprising carbon dioxide. Carbon dioxide may also be recovered from biogas generated from the latter anaerobic digestion and combined with biogenic carbon dioxide generated from the other stages of the process, along with the fossil derived hydrogen.

Forming the Biogenic Carbon-based Fuel, Fuel Intermediate or Chemical Product

As discussed, by collecting biogenic carbon dioxide obtained or derived from a process that produces a fuel, a fuel intermediate, a chemical product or an energy product, and subsequently using the biogenic carbon dioxide to produce a second biogenic carbon-based fuel, a greater amount of the carbon of the initial organic material can be converted to a final product. This in turn can result in significant improvements in biogenic product yield from the starting material. For example, in certain embodiments of the invention, the total energy of the biogenic carbon-based fuel or products that can be produced from the non-fossil organic material can be increased by at least 10%, 25% or 30% relative to a conventional biofuel production process without collecting carbon dioxide.

The biogenic carbon dioxide can be reduced using fossil derived hydrogen to other $C_1$-$C_n$ molecules in one or more chemical and/or biologic conversions. Representative examples of such processes are described below.

In one embodiment, the fossil derived hydrogen is sourced from a process that produces fossil-containing molecules, such as carbon monoxide and/or carbon dioxide, and hydrogen from a fossil fuel hydrocarbon. In such process, the fossil-containing molecules are separated from the hydrogen. Preferably, all the carbon-containing molecules are removed, typically to achieve more than 90% or 95% by weight hydrogen. The hydrogen thus obtained is typically a low cost source compared to other sources, such as renewable sources. This hydrogen may then be used in the production of the second biogenic-based fuel or fuel intermediate. While hydrogen from fossil fuel is used in the biofuel production, since the hydrogen does not itself contain fossil carbon the carbon dioxide tailpipe emissions that result from combustion of the biofuel, such as in transportation vehicles, contain only biogenic carbon, and thus are considered to have a neutral effect on atmospheric carbon dioxide levels. Although the carbon dioxide emissions associated with the hydrogen production from fossil fuels are included in the GHG emission analysis, in one embodiment, the life cycle GHG emissions of the fuel or fuels produced are reduced relative to a gasoline baseline using various approaches (e.g., placing the fossil-based $CO_2$ back underground), while at the same time advantageously using a low cost hydrogen source.

In some embodiments, the amount of biogenic carbon in the second biogenic carbon-based fuel or fuel intermediate may be between 70 mole % and 100 mole % (mol:mol), between 75 mole % and 100 mole %, between 80 mole % and 100 mole %, between 85 mole % and 100 mole %, between 90 mole % and 100 mole % or between 95 mole % and 100 mole % (mol:mol of biogenic and non-biogenic carbon).

In one embodiment, radiocarbon analysis is used to determine the presence of a biogenic component in the biogenic carbon-based fuel or fuel intermediate using known methodology for carbon 14 dating. However, it should be understood that the carbon component of the biogenic fuel or fuel intermediate may be non-biogenic, but still be recognized as biogenic. To illustrate, if the fuel is derived from carbon dioxide withdrawn from a pipeline, and such carbon dioxide is non-biogenic, or a contains a mixture of biogenic and non-biogenic carbon dioxide and yet qualifies as renewable under prevailing regulations, the withdrawn carbon dioxide will still be considered biogenic.

In one embodiment, the hydrogen is sourced from a third party. Sourcing the hydrogen includes directly or indirectly obtaining hydrogen for use in the production of the fuel or fuel intermediate, including obtaining the hydrogen from a third party. If the hydrogen is sourced from a third party, it may be obtained directly or indirectly by way of written documentation, including a contract, or other agreement between two or more parties.

The stream sourced from the hydrogen production process is referred to as a "stream enriched in hydrogen", meaning a stream comprising greater than 80 mol % hydrogen (mol:mol).

In one embodiment, the fossil derived hydrogen is produced by a process in which methane is converted to a syngas stream comprising carbon monoxide and hydrogen. Subsequently, further hydrogen enrichment steps may be conducted on the syngas stream or a stream derived therefrom to produce a stream with increased hydrogen content relative to syngas. The hydrogen may be enriched by various techniques known to those of skill in the art including by membranes, adsorbents or by further chemical conversions conducted to produce additional hydrogen.

In certain non-limiting embodiments of the invention, the hydrogen is sourced from reforming, such as steam methane reforming (SMR) or autothermal reforming (ATR). Both steam methane reforming and autothermal reforming methods operate by exposing the methane to a catalyst at high temperature and pressure to produce syngas, which is a mixture comprising hydrogen and carbon monoxide. Steam methane reforming is often referred to as a non-oxidative process that converts the methane into hydrogen and carbon monoxide by the following reaction:

$$CH_4 + H_2O \rightarrow CO + 3H_2.$$

Autothermal reforming uses oxygen and carbon dioxide or oxygen and steam in a reaction with methane to form carbon monoxide and hydrogen. The autothermal reaction using oxygen and carbon dioxide can be described by the following reaction:

$$2CH_4 + O_2 + CO_2 \rightarrow 3H_2 + 3CO + H_2O.$$

The autothermal reaction using oxygen and steam proceeds by the following reaction:

$$4CH_4 + O_2 + 2H_2O \rightarrow 10H_2 + 4CO.$$

Examples of other reforming reactions include partial oxidation and dry reforming.

The reforming may be followed by a water gas shift reaction to produce the fossil carbon dioxide and hydrogen. For example, steam methane reforming followed by a water gas shift converts natural gas to carbon dioxide and hydrogen as follows:

$$CH_4 + H_2O \rightarrow CO + 3H_2$$

$$CO + H_2O \rightarrow CO_2 + H_2$$

Overall: $CH_4 + 2H_2O \rightarrow CO_2 + 4H_2.$

In one embodiment, the water gas shift includes at least a high temperature shift, which is a water gas shift typically conducted at a temperature of at least 275° C., typically higher than 300° C. An example of a temperature range for the high temperature shift is 300° C. to 450° C. Subsequent to a high temperature shift, a low temperature shift is optionally conducted. The low temperature shift occurs at a lower temperature than a high temperature shift, such as a temperature lower than 300° C., more typically less than 250° C. An example of a temperature range for the low temperature shift is 180° C. to 250° C. The high temperature shift generally results in the incomplete conversion of carbon monoxide to carbon dioxide. A low temperature shift may increase such conversion, thereby reducing the carbon monoxide concentration further. This may produce an outlet stream having a carbon monoxide mole % of less than 5 mol %, less than 3 mol %, more typically less than 2 mol %. Both high and low temperature shift reactions are generally carried out in the presence of a catalyst.

The stream resulting from the reforming and the water gas shift reaction typically contains a relatively high concentration of hydrogen and carbon dioxide, making this gaseous component more easily recoverable relative to waste streams generated from other processes that burn fossil fuel, such as flue gases from power plants. The fossil carbon dioxide recovered can then be introduced underground in a geologic formation, thereby further reducing GHG emissions associated with the biogenic fuel or fuel intermediate. Another advantage of using hydrogen from steam methane or autothermal reforming is that, in some regions, natural gas can be obtained at low cost relative to renewable options. As a result, the use of natural gas to make hydrogen, with the introduction of the low energy content carbon dioxide byproduct underground, provides not only an economical source of high energy hydrogen for the process, but also GHG benefits that can be attained at minimal cost.

The hydrogen produced by the water gas shift reaction can be recovered from non-hydrogen components, including carbon dioxide, from a gaseous or liquid stream using known techniques employing adsorbents or membranes. An example of a recovery technique using adsorbents is pressure swing adsorption (PSA), which is commonly used to recover hydrogen produced by steam methane reforming. As would be appreciated by those of skill in the art, PSA is used to separate gas species from a mixture of gases under pressure using adsorbent materials such as zeolites, molecular sieves or activated carbon. The adsorbent material absorbs the target gas species at high pressure and the separation relies on the different affinity of various gas species in the gas stream. When the pressure is lowered, the target gas desorbs. In the practice of certain embodiments of the present invention, PSA adsorbs hydrogen and the desorption results in a stream concentrated in hydrogen. A stream comprising non-adsorbed species, including carbon dioxide, is also generated by PSA. This latter stream comprising carbon dioxide is often referred to as a purge gas stream.

Figure 7:
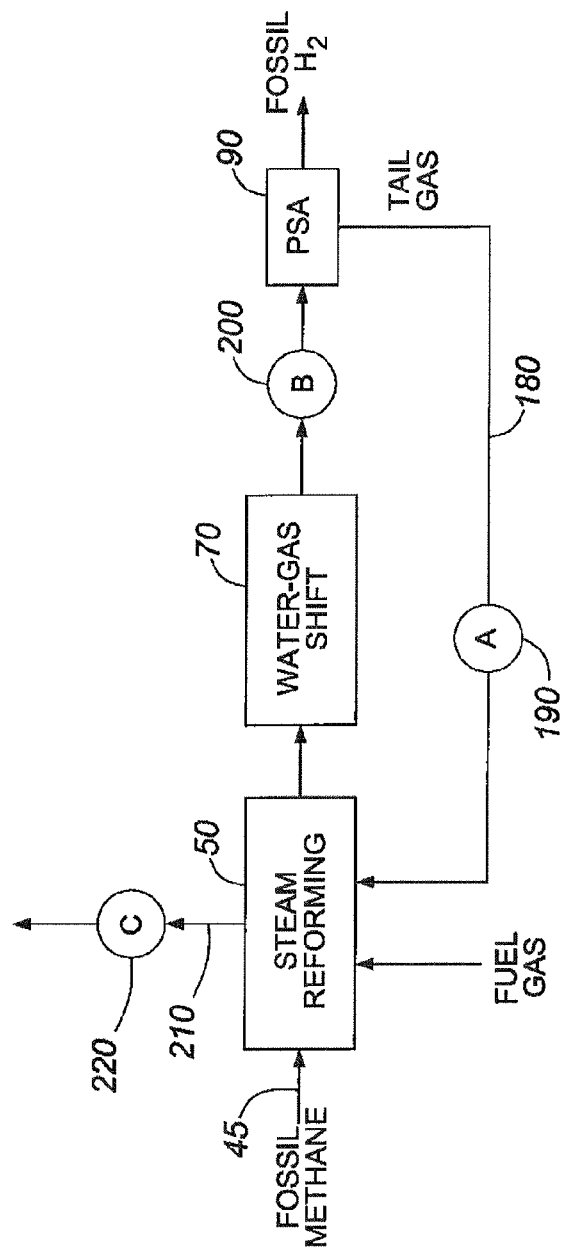
FIG. 7 is a process flow diagram showing streams from which carbon dioxide can be recovered during a hydrogen production process for introduction underground.

As noted, carbon dioxide for introduction underground can be recovered from one or more streams comprising carbon dioxide generated during the above-mentioned hydrogen production process. FIG. 7 is a process flow diagram depicting non-limiting examples of streams produced during the hydrogen production process from which carbon dioxide can be recovered. As shown, the hydrogen production process uses fossil methane as a feed 45, which is subjected to steam reforming unit 50, followed by a water gas shift reaction 70 and a PSA unit 90. The PSA unit 90 produces a stream enriched in fossil hydrogen, in this case at levels greater than 99 mol % hydrogen and a tail gas stream 180 comprising carbon dioxide, carbon monoxide and hydrogen. The fossil carbon dioxide can be recovered from this tail gas stream 180 in $CO_2$ recovery unit 190. A further example of a stream from which carbon dioxide can be recovered is a stream exiting a water gas shift unit and upstream of the pressure swing adsorption unit 90 in recovery unit 200. Moreover, carbon dioxide can also be recovered from any process unit upstream of a water gas shift reaction. An example of such a stream is a flue gas stream 210 exiting a steam methane reforming unit 50 in which the steam methane reforming reaction is conducted. The carbon dioxide can be recovered from this stream 210 in carbon dioxide recovery 220. This latter stream is produced upon combustion of fuel gas, such as methane, hydrogen and/or carbon monoxide used for supplying heat to steam methane reforming unit 50. The combustion of these components to supply heat results in the production of fossil carbon dioxide that is often otherwise vented. Recovery of fossil carbon dioxide from any of these streams can be carried out using known techniques, including processes using adsorbents, membranes, solvents or other suitable techniques known to those of skill in the art.

As mentioned, the biogenic carbon dioxide and fossil derived hydrogen are used to form the biogenic carbon-based fuel or fuel intermediate by a variety of different single and/or multi-step chemical or biologic production processes. Some examples of production processes are set forth below.

(a) Production Processes Using Hydrogen and Carbon Dioxide to Produce Carbon Monoxide The biogenic carbon dioxide and hydrogen sourced from fossil fuel may be used to produce carbon monoxide as a feedstock for biofuel production by the following reverse water gas shift reaction:

$$CO_2 + H_2 \rightarrow CO + H_2O.$$

The carbon monoxide produced by the above reaction can be further converted in one or more chemical and/or biological steps to a fuel or fuel intermediate. For example, combining carbon monoxide from the above reaction with hydrogen results in syngas that can be used itself as a fuel or to produce a fuel or fuel intermediate. As described previously, examples of products made directly or indirectly from syngas include liquid hydrocarbons, methane, hydrogen, methanol, ethanol or ammonia.

The above reverse water gas shift reaction to produce carbon monoxide can be conducted as part of a reforming operation. According to such embodiment, the biogenic carbon dioxide and fossil derived hydrogen may be fed to a reformer. The steam reforming may be operated such that the foregoing reverse water gas shift occurs during the steam reforming, thereby producing carbon monoxide and water. The output from the steam reforming will then include syngas comprising carbon monoxide, hydrogen and carbon dioxide. The resultant syngas can subsequently be converted to products via one or more biologic and/or chemical conversions. In one embodiment, the syngas is converted to a hydrocarbon through a chemical conversion, such as the Fischer-Tropsch reaction described earlier or alternatively a process in which the syngas is converted to methanol and then to the hydrocarbon, such as gasoline, described in more detail hereinafter. In either case, the product from the syngas will contain biogenic carbon.

In one embodiment, the steam reformer is fed with a stream comprising biogenic carbon dioxide and methane derived from anaerobic digestion, along with fossil derived hydrogen. The presence of methane can aid in reducing the fossil hydrogen requirement because hydrogen is produced in situ from methane in the reformer.

Figure 6:
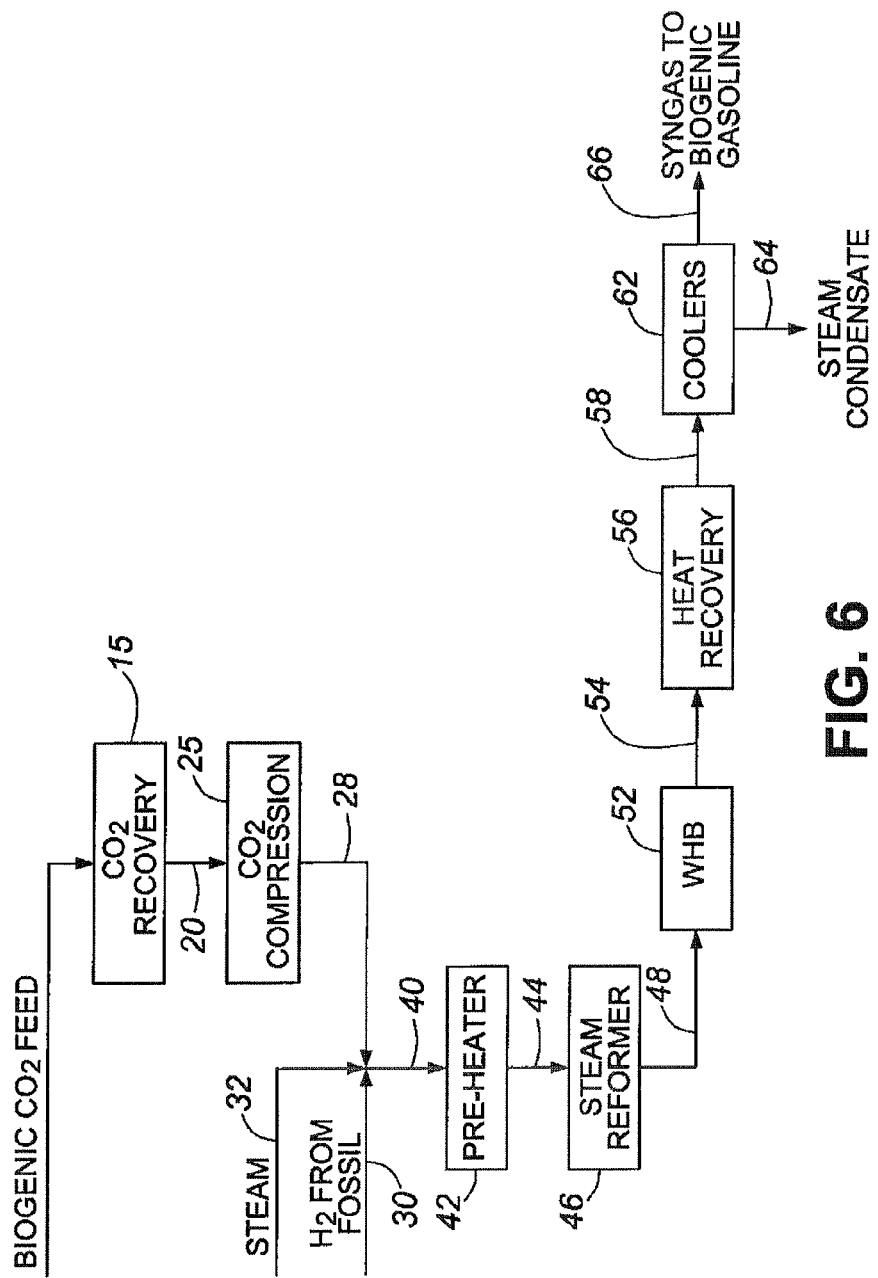
FIG. 6 is a process flow diagram showing the production of biogenic gasoline using fossil derived hydrogen and biogenic carbon dioxide.

A non-limiting example of a process in which biogenic carbon dioxide and fossil derived hydrogen are fed to a reformer to produce syngas, which in turn is converted to a hydrocarbon fuel or fuel intermediate that can substitute gasoline, diesel or other petroleum products is provided in FIG. 6, as described in more detail in Example 6.

The reforming to produce syngas from biogenic carbon dioxide and hydrogen and the steam methane reforming and/or a water gas shift to produce hydrogen from fossil methane often generates excess heat. The heat generated from any one or a combination of these reforming and water gas shift operations can be used to provide energy in other unit operations. For example, the heat can be used to supply energy in a process to produce an energy product or a chemical product, a fuel or a fuel intermediate from the non-fossil organic material. The process can include the fermentation of non-fossil organic material to produce ethanol. For example, such heat can be utilized in a dryer, thermal oxidizer, distillation and/or evaporation in an ethanol production process using corn as a feedstock. Alternatively, the heat can be used in a production process to make ethanol from biomass or biomass derived material. This includes supplying heat to similar operations as a corn ethanol process or for pretreatment processes. In a further embodiment of the invention, heat from the reforming can be used to supply energy for a production process in which syngas is converted to a hydrocarbon through a chemical conversion such as that described above. In another embodiment of the invention, heat from the reforming can be used to produce electricity either for internal use or for export to the grid. By implementing such energy savings, the life cycle GHG emissions can be reduced by at least 20% relative to a gasoline baseline. Advantageously, such GHG savings can enable the generation of a biofuel credit in relation to the fuel produced or sold.

Syngas produced by the reverse water gas shift can also be converted to a fuel, fuel intermediate and/or chemical product by a biologic conversion utilizing microorganisms or other biocatalysts. For example, acetogenic microorganisms can be used to produce a biogenic carbon-based product from carbon monoxide through fermentation. For example, anaerobic microorganisms from the genus *Clostridium* can produce ethanol or other products from the carbon monoxide.

The production of ethanol by the acetogenic microorganisms proceeds through a series of biochemical reactions. Without being bound by any particular theory, the reactions carried out by the microorganism are as follows:

$$6CO + 3H_2O \rightarrow CH_3CH_2OH + 4CO_2$$

$$6H_2 + 2CO_2 \rightarrow CH_3CH_2OH + 3H_2O.$$

Examples of strains that can produce ethanol from syngas are those from the genus *Clostridium*. In addition to ethanol, *Clostridium* bacteria might produce significant amounts of acetic acid (or acetate, depending on the pH) in addition to ethanol, although to improve ethanol yield it is possible to adjust fermentation conditions by nutrient limitation or by providing excess fossil derived hydrogen or carbon monoxide to achieve a desired ethanol productivity. Such conditions can be readily selected by those of skill in the art and it should be appreciated that the invention is not constrained by any particular set of parameters selected for fermentation to improve productivity.

The carbon monoxide from the above reverse water gas shift reaction can also be reacted with fossil derived hydrogen to produce methanol. The reactions are as follows:

$$CO_2 + H_2 \rightarrow CO + H_2O \text{ (reverse water gas shift)}$$

$$CO + 2H_2 \rightarrow CH_3OH.$$

Another route for producing methanol is the direct hydrogenation of $CO_2$ to produce methanol (not shown).

In one embodiment, the methanol is used as a fuel intermediate to make another fuel. Ethanol is one such fuel and its production from methanol can proceed by a variety of different reaction routes. The production of ethanol from methanol through organic acid intermediates, such as acetic acid, is known in the art. For example, methanol can be reacted with carbon monoxide to make acetic acid, acetate or a combination thereof, and the acetate is subsequently reacted with hydrogen to make ethanol and water. The reaction is as follows:

$$CH_3OH + CO \rightarrow CH_3COOH$$

$$CH_3COOH + 2H_2 \rightarrow CH_3CH_2OH + H_2O.$$

The hydrogenation of acetic acid may favour the production of ethyl acetate over ethanol. Special hydrogenating catalysts (platinum/copper or palladium/cobalt) may be used to produce ethyl acetate from acetic acid. The ethyl acetate can then be hydrogenated to ethanol. Ethanol production can also proceed via a methyl acetate intermediate. According to such embodiment, methanol is carbonylated to methyl acetate and optionally acetic acid. The methyl acetate is then hydrogenated to ethanol.

The methanol can also be converted to gasoline by forming dimethyl ether by a dehydration reaction. Subsequently, an equilibrium mixture of methanol, dimethylether and water is converted to short-chain olefins. In a further reaction step, the short-chain olefins are reacted to form higher olefins, including n/iso-paraffins, aromatics and napththenes, which are further treated to make gasoline.

(b) Other Processes Employing Conversion of Biogenic $CO_2$ and Fossil Derived $H_2$ to Products The biogenic $CO_2$ and fossil derived $H_2$ can also be more directly converted to the biogenic carbon-based fuel or fuel intermediate rather than proceeding through a reverse water gas shift reaction to produce CO and $H_2O$. Representative examples of such processes are described below.

According to one embodiment, the biogenic carbon dioxide and fossil derived hydrogen is converted to an alcohol, such as ethanol, by fermentation with a bacterium. In such embodiment, ethanol is produced from $CO_2$ and $H_2$ by the following reaction scheme:

$$6H_2 + 2CO_2 \rightarrow CH_3CH_2OH + 3H_2O.$$

The ethanol produced is referred to as "biogenic ethanol", meaning that carbon in the ethanol is from biogenic carbon or considered renewable or biogenic by those of skill in the art.

By adding fossil derived hydrogen, the above reaction can provide for significant yield increases relative to conventional ethanol production processes. In certain embodiments, the yield of ethanol achieved by the invention can be greater than 10%, 20% or 30% relative to the yield from conventional processes for producing biogenic ethanol from corn without collecting biogenic carbon dioxide and using it to make a product. Moreover, a byproduct generally considered a low energy waste product from processing of biomass or biomass-derived material can be converted into a valuable biofuel, in particular a biofuel that is eligible for fuel credit generation by virtue of its biogenic carbon. Further, using fossil derived hydrogen is uniquely low cost compared to other potential sources of hydrogen. Thus, in certain advantageous embodiments, a higher yield of biofuel may be achieved by a low cost method.

The production of ethanol from fossil derived hydrogen and biogenic carbon dioxide may be carried out with hydrogen oxidizing chemoautotrophs. In one embodiment, the microorganisms used includes any bacteria from a genus selected from *Acetogenium, Acetobacterium, Acetoanaerobium, Butyribacterium* and *Clostridium* that are capable of the above bioconversion. In one embodiment, the microorganism used to produce ethanol is from the genus *Clostridium*. Without being limiting, a particularly suitable microorganism for producing ethanol from the biogenic carbon dioxide and fossil derived hydrogen is *Clostridium ljungdahlii*. This bacterium can effectively convert biogenic carbon dioxide and hydrogen to ethanol.

A representative example of a process in which biogenic carbon dioxide and hydrogen from fossil fuel are fermented to produce ethanol is provided in FIG. 1, and described in more detail in Example 1 below.

The fossil derived hydrogen is typically provided in excess of biogenic carbon dioxide to satisfy the above stoichiometric molar ratio of $H_2:CO_2$ of 3:1 to produce ethanol according to the foregoing reaction scheme. An example of a range of molar ratios of $H_2:CO_2$ that can be utilized is from 2:1 to 4:1 or from 2.5:1 to 3.5:1. The gases, hydrogen and carbon dioxide, are introduced to the bioreactor either together in a combined stream comprising both components or as separate respective streams. This includes the introduction of the gases together or separately along with broth. The bioreactor contains a liquid nutrient broth containing the bacteria and components required for their growth, such as vitamins and salts. In one embodiment, the bioreactor is one of a plurality of bioreactors in a system in which the reactors are arranged in series, parallel or a combination of such arrangements. A growth reactor may also be utilized which feeds a separate bioreactor in which most of the product ethanol is produced or a growth phase can be carried out in a fermentation bioreactor itself.

The bioreactor for conducting the conversion can be a stirred or an unmixed tank reactor. An example of a bioreactor that can be used to ferment the fossil derived hydrogen and biogenic carbon dioxide is a deep tank bioreactor, which is a reactor generally having a depth of greater than 10 meters. The deep tank reactor may be stirred to facilitate contact between the gases and the liquid nutrient broth. The gases may also be introduced at the bottom region of the bioreactor and bubble through the liquid broth. Optionally, the gases are introduced along with the liquid broth, such as together with a broth re-circulation stream. Mechanical pumping may also be utilized to facilitate liquid flow and mass transfer. Another type of reactor that can be utilized in the practice of the invention is a gas lift reactor, wherein the broth is agitated through the use of gas nozzles.

The bioreactor may employ cell recycle in order to replenish the concentration of cells in the reactor. According to such embodiment, a liquid stream comprising cells is withdrawn from the reactor and sent to a solids-liquid separation to separate cells from the stream. The separated cells are returned to the reactor and a cell-free stream resulting from the separation is sent to product recovery to recover ethanol, typically by distillation.

Gases may accumulate in the headspace of the reactor. Such gases may be recycled back to the bioreactor or can be fed back to an SMR either as feedstock or as fuel. The gases withdrawn from the reactor may be combined with a stream comprising carbon dioxide and hydrogen introduced to the reactor.

The recovery of ethanol can be carried out using conventional techniques, such as distillation followed by further concentration by molecular sieves. After recovery of ethanol, a stream remains referred to as still bottoms. The still bottoms stream can be sent to a solids-liquid separation and the liquid stream resulting from the separation can be fed back to the reactor. Still bottoms from distillation or a fraction thereof may also be sent to an evaporator unit. In such unit, the still bottoms are concentrated and the evaporated liquid is condensed by cooling. The evaporator condensate may then be recycled as a liquid stream back to the reactor to reduce water usage.

Alternatively or in addition to water recycle, at least a portion of the liquid stream obtained from the still bottoms can be fed to an anaerobic digestion. The anaerobic digestion produces a stream comprising methane and carbon dioxide. The carbon dioxide can be separated from other components of the biogas and introduced to the bioreactor in which carbon dioxide and hydrogen are converted to ethanol. A non-limiting example of such a process is shown in FIG. 4.

While the production of ethanol from carbon dioxide and hydrogen has been described, hydrogen oxidizing chemoautotrophs can also produce acetic acid from these gaseous substrates. For example, *Clostridium* species are known to produce acetic acid by the following reaction mechanism:

$$4H_2 + 2CO_2 \rightarrow CH_3COOH + 2H_2O.$$

As would be appreciated by those of skill in the art, acetic acid, acetate or both of these species will be present as dictated by the pH of the solution.

Acetic acid can be sold as a product in either the acetate or acid form or converted to a fuel such as ethanol.

Acetic acid and/or acetate can also be introduced back to an anaerobic digester and converted to methane by anaerobic digestion. The acetic acid and/or acetate introduced to an anaerobic digester can be a primary product of fermentation or a byproduct. Often fermentation of hydrogen and carbon dioxide to ethanol produces acetic acid and/or acetate as a byproduct. By recovering and introducing the acetic acid and/or acetate to anaerobic digestion, a byproduct from ethanol fermentation can be converted to biogas, thereby resulting in further potential improvements in the yield of fuel from the process.

Another stream from a gaseous fermentation that can be introduced to anaerobic digestion to potentially increase the yield of biogas is an exhaust gas stream from a fermentor. Such an exhaust gas stream may be any gaseous stream that is obtained from a fermentor to produce a fermentation product. For example, during the fermentation of fossil derived hydrogen and biogenic carbon dioxide, gases may be collected in the headspace of a reactor and be withdrawn as an exhaust gas stream. The gases from an exhaust gas stream are often recycled back to the bioreactor, but can also be introduced to an anaerobic digester. By introducing the exhaust gas stream to an anaerobic digester, such byproduct from the fermentation can be converted to biogas, thereby resulting in further potential improvements in the yield of fuel from the process. In one embodiment, the biogas is used directly or indirectly to provide a biogenic carbon-based fuel, fuel intermediate or chemical product. In one embodiment, the biogas is used to make acetic acid, which in turn is converted to ethanol.

Products that are gaseous at standard temperatures and pressures can also be produced from biogenic carbon dioxide and fossil derived hydrogen. According to one embodiment, the biogenic carbon dioxide and fossil derived hydrogen is used to produce methane via the following reaction:

$$CO_2 + 4H_2 \rightarrow CH_4 + 2H_2O.$$

The foregoing mechanism for producing methane is referred to herein as a "methanation" or "Sabatier reaction". The methane thus produced can be used itself as fuel or can be used as a fuel intermediate to produce another fuel or fuel intermediate, as set out previously. The above reaction can be carried out as either a biologic or chemical conversion.

In certain embodiments of the invention, the formation of methane using biogenic carbon dioxide and fossil derived hydrogen can be carried out as part of a process to improve methane yield from a process that produces methane from non-fossil organic material, such as anaerobic digestion. As described above, anaerobic digestion produces methane and other components including biogenic carbon dioxide. The biogenic carbon dioxide and methane can be separated from crude biogas and combined with the hydrogen sourced from fossil fuel hydrocarbon or methane and carbon dioxide can be processed together with hydrogen to make methane or syngas. The biogenic carbon dioxide is converted to methane by reaction with hydrogen according to the above reaction.

The methanation reaction with fossil derived hydrogen thus produces additional methane from the biogenic carbon dioxide generated during anaerobic digestion. The foregoing process results in a higher yield of biogenic carbon-based fuel or fuel intermediate from the original non-fossil organic material. The product is considered a biofuel.

Although the methanation reaction is described above in connection with improving methane yield, it should be understood that the biogenic carbon dioxide may be obtained from any fermentation of non-fossil organic material or alternatively from a thermal process.

The methanation reaction may take place in a reactor in the presence of a catalyst, typically a metal. The methanation reaction can also be carried out as a biologic conversion. For example methanogenic, hydrogen-utilizing microbes including *Methanobacteriales*, *Methanococcales*, and *Methanomicrobiales* or *Methanopyrales* can produce methane from carbon dioxide and hydrogen. Such microorganisms are known as hydrogenotrophic methanogens.

According to another embodiment, the biogenic carbon dioxide is reacted with a hydrocarbon, such as methane. According to this embodiment, the hydrocarbon comprises at least one hydrogen atom that originates from the fossil derived hydrogen. For example, methane can be reacted with biogenic carbon dioxide to produce syngas in a dry reforming process. The syngas can subsequently be reacted to make methanol. The reactions are as follows:

$$CH_4 + CO_2 \rightarrow 2H_2 + 2CO$$

$$CO + 2H_2 \rightarrow CH_3OH.$$

According to certain embodiments of the invention, the hydrogen production process to produce fossil derived hydrogen is conducted in close vicinity to a fermentation plant. An advantage of producing hydrogen close to a fermentation plant is that energy generated during reforming can be used in various stages of a process to produce and recover a fermentation product. Since many stages of the fermentative process are energy-intensive, this can significantly reduce the costs of operating a fermentation plant. Energy savings from heat integration may also contribute to reducing the life cycle GHG emissions of a fuel relative to a gasoline baseline and thus can potentially enable the generation of a valuable biofuel credit in relation to the fuel produced or sold.

For instance, the heat from reforming carried out during the hydrogen production can be used to supply energy for processes comprising a fermentation from which the biogenic $CO_2$ feed is collected and used to produce the biogenic carbon-based fuel, fuel intermediate or chemical product. For example, such heat can be utilized in a dryer, thermal oxidizer, distillation and/or evaporation conducted as part of a process comprising fermentation. Such steps are often part of a production process comprising fermentation using corn as a feedstock, although the heat from reforming can be used in any production process comprising fermentation to make a fermentation product, including processes using biomass or biomass derived material. In those processes using corn as a feedstock, driers used to dry still bottoms remaining after distillation of ethanol to produce products such as dried distiller's grains are especially energy-intensive to operate and so using a portion of the heat from reforming at this stage of a production process can potentially make the process significantly more efficient. A non-limiting example of a process in which hydrogen production is integrated with a corn ethanol plant to reduce the energy with such a drying step is described in Example 5 with reference to FIG. 5.

Alternatively or in addition, the heat generated from reforming can be used to provide energy in other unit operations besides production processes comprising fermentation. For instance, heat from the reforming can also be used to supply energy for processes in which syngas is converted to a fuel or fuel intermediate. An example of such a process utilizing integration is set forth in Example 6.

According to another embodiment, the biogenic $CO_2$ is reacted with a microorganism that has been engineered to provide fixation of $CO_2$ to products, such as alkane-based fuels and/or fuel intermediates.

Reducing GHG Emissions

In some embodiments the process includes carrying out or arranging for one or more parties to carry out at least one step that contributes to a reduction in the life cycle GHG emissions of one or more biogenic carbon-based fuels produced directly or indirectly by the process. In certain embodiments, the life cycle GHG emissions can be at least 20%, 30%, 40%, 50%, 60%, 70% or 80% less than a gasoline baseline. Such reductions in life cycle GHG emissions can allow for advantaged fuel credit generation, as discussed below.

As used herein "arranging" or "causing" means to bring about, either directly or indirectly, or to play a required role in a series of activities through commercial arrangements such as a written agreement, verbal agreement or contract.

In one embodiment, GHG emissions are reduced by introducing fossil carbon dioxide, which is generated during the production of hydrogen from fossil fuel hydrocarbon, underground. For example, the fossil carbon dioxide may be introduced into an underground geological formation, thereby reducing life cycle GHG emissions by preventing carbon from fossil sources from being emitted to the atmosphere. Without being limiting, the fossil carbon dioxide may be introduced underground for extracting oil or gas in an enhanced oil or gas recovery. A description of enhanced oil and gas recovery is set forth in U.S. Patent Publication No. 2013/0089905 (published Apr. 11, 2013), which is incorporated herein by reference and particularly for the purpose of describing enhanced oil and gas recovery. The enhanced oil or gas recovery is any process that enables the recovery of underground oil or gas with the aid of fluid, including liquid or gas injection or two-phase fluid, such as foam. Carbon dioxide can also be injected into saline aquifers or other geologic formations in which the carbon dioxide can be contained, although as would be appreciated by those of skill in the art, some amount of carbon dioxide leakage may occur from the formation over a relatively long period of time. In another embodiment, the at least one step for reducing GHG emissions may comprise incorporating the fossil carbon dioxide into manufactured chemical products such as sodium bicarbonate and/or calcium carbonate that are stable and thus greatly slow or substantially prevents the fossil carbon dioxide from being emitted into the atmosphere.

In order to transport the fossil carbon dioxide to the proximity of an underground geologic formation, it may be introduced to an apparatus for transporting carbon dioxide, such as a pipeline, railroad car or truck. An amount of carbon dioxide is withdrawn from the transport apparatus for introduction underground, typically by a different party than the party that generates the carbon dioxide. In this case, the party that produces the fossil derived hydrogen and the fossil carbon dioxide may arrange for, or cause, a third party to withdraw an amount generally corresponding to that introduced to the transport apparatus (e.g., pipeline).

According to one embodiment of the invention, the first chemical or energy product produced or derived from the non-fossil organic material displaces a chemical or energy product made from fossil fuel. By displace, it is meant that the first energy product or chemical product, reduces or is recognized by those skilled in the art as reducing, the production or use of a corresponding fossil derived energy or chemical product, thereby reducing the life cycle GHG emissions associated with the biofuel. The GHG emission reductions are typically reflected in a life cycle GHG emission calculation. The GHG emissions for production or use of the chemical or energy product are thereby reduced because the GHG emissions associated with the displaced chemical or energy product from fossil fuel are avoided, and replaced with a chemical or energy product produced or derived from non-fossil organic material. The chemical or energy product produced from fossil fuel energy sources is referred to as a fossil derived chemical or energy product.

Fossil derived hydrogen can also be transferred by a transport apparatus, such as a pipeline, railroad car or truck. In some embodiments, collection of carbon dioxide from the hydrogen production process reduces the GHG emissions attributable to hydrogen and such beneficial environmental attributes may be transferred by feeding such hydrogen into a transport apparatus and withdrawing an equivalent amount from the transport apparatus, thus transferring the environmental attributes to the withdrawn hydrogen.

By way of example, the electricity produced by combusting biomass or biomass derived material, such as lignin, may displace the production or use of fossil derived electricity from a coal burning power plant. Displacement of an energy product generally involves exporting the energy product from the process. However, it will be appreciated that displacement encompasses the use of an energy product as an energy source for a stage within the process itself. For example, electricity and/or heat produced by combusting lignin can be used to provide energy for the production process that produces the first product derived from the non-fossil organic material. According to one embodiment, lignin that results after a production process in which a lignocellulosic feedstock is converted to sugar, and fermented to produce a fermentation product, is burned to generate electricity and/or heat, which is subsequently used in one or more stages within the production process to supply energy in the form of heat and/or electricity. As would be appreciated by those of skill in the art, such embodiment can displace the use of fossil fuel since there is a reduction of the production or use of fossil derived energy.

In one embodiment, an energy product is both exported and also used within the process itself as an energy source.

In a further example, a chemical product such as acetic acid, which may be produced from methanol, derived from non-fossil organic material can displace acetic acid made from fossil sources. Similarly, a chemical product produced by the process could be used within the process itself to reduce chemical usage, thereby reducing the use or production of a corresponding product made from fossil sources.

Determining Life Cycle GHG Emissions

According to certain embodiments of the invention, one or more biogenic carbon-based fuel that is produced in the process, which includes by downstream parties, has life cycle GHG emissions associated therewith that are at least 20%, 30% or 40% lower than a gasoline baseline. However, in certain embodiments, these savings can be at least as much as 50% lower than a gasoline baseline, or even at least as much as 60%, 70%, 80% or 90% lower than a gasoline baseline.

To determine life cycle GHG emissions associated with a biogenic carbon-based fuel, analyses are conducted to calculate the GHG emissions related to the production and use of the fuel throughout its life cycle. Life cycle GHG emissions include the aggregate quantity of GHG emissions related to the full life cycle of the transportation or heating fuel, including all stages of fuel and feedstock production and distribution, from feedstock generation or extraction through the distribution and delivery and use of the finished fuel to the ultimate consumer. GHG emissions account for total net GHG emissions, both direct and indirect, associated with feedstock production and distribution, the fuel production and distribution and use.

Examples of Methodologies for Calculating Life Cycle GHG Emissions

Because many of the laws adopted differentiate the requirements for fuels based upon their net GHG emissions impacts, those skilled in the art are familiar with methods to analyze and characterize the expected net GHG emissions of fuel pathways that regulators have developed and/or adopted. Thus, life cycle GHG emissions are determined in accordance with such methods known to those skilled in the art, in accordance with prevailing rules and regulations.

Life cycle GHG emissions evaluations generally consider GHG emissions associated with each of:
(a) feedstock production and recovery, including the source of carbon in the feedstock, direct impacts such as chemical inputs, energy inputs, and emissions from the collection and recovery operations, and indirect impacts such as the impact of land use changes from incremental feedstock production;
(b) feedstock transport, including feedstock production and recovery and GHG emissions from feedstock transport including energy inputs and emissions from transport;
(e) fuel production, including chemical and energy inputs, emissions and byproducts from fuel production (including direct and indirect impacts); and
(d) transport and storage of the fuel prior to use as a transportation or heating fuel, including chemical and energy inputs and emissions from transport and storage.

Known models to measure life cycle GHG emissions associated with the one or more fuels of the invention, include, but are not limited to:
(i) GREET Model—GHGs, Regulated Emissions, and Energy Use in Transportation, the spread-sheet analysis tool developed by Argonne National Laboratories;
(ii) FASOM Model—a partial equilibrium economic model of the U.S. forest and agricultural sectors developed by Texas A&M University;
(iii) FAPRI International Model—a worldwide agricultural sector economic model that was run by the Center for Agricultural and Rural Development ("CARD") at Iowa State University;
(iv) GTAP Model—the Global Trade Analysis Project model, a multi-region, multi-sector computable general equilibrium model that estimates changes in world agricultural production as well as multiple additional models; and
(v) ISO (International Organization for Standardization) standards for GHG emissions accounting and verification—provides guidance for quantification, monitoring and reporting of activities intended to cause greenhouse gas (GHG) emission reductions or removal enhancements.

The life cycle GHG emissions or carbon intensity of the biogenic carbon-based fuel is generally measured in carbon dioxide equivalents ($CO_2$eq). As would be understood by those of skill in the art, carbon dioxide equivalents are used to compare the emissions from various GHGs based upon their global warming potential (GWP), which is a conversion factor that varies depending on the gas. The carbon dioxide equivalent for a gas is derived by multiplying the amount of the gas by the associated GWP.

$$\text{grams of } CO_2 eq = ((\text{grams of a gas})*(\text{GWP of the gas}))$$

The GWP conversion value used to determine grams of $CO_2$eq will depend on applicable regulations for calculating life cycle GHG emissions reductions. The GWP under EISA is 1, 21 and 310, respectively, for carbon dioxide, methane and nitrous oxide as set forth in Renewable Fuel Standard Program (RFS2) Regulatory Impact Analysis, February 2010, United States Environmental Protection Agency, EPA-420-R-10-006, pg. 13, of which the entire contents are incorporated herein by reference. Under California's LCFS, the GWP is 1, 25 and 298, respectively, for carbon dioxide, methane and nitrous oxide, as measured by the GREET model. It should be appreciated that GWP values can be readily calculated by those of skill in the art in accordance with regulations.

The unit of measure for carbon intensity or life cycle GHG emissions that may be used to quantify GHG emissions of the biogenic carbon-based fuel is grams $CO_2$eq per MJ of energy in the fuel or grams $CO_2$eq per million British thermal units of energy in the fuel (MMBTU). The units used to measure life cycle GHG emissions will generally depend on applicable regulations. For example, under the EPA regulations, GHG emissions are measured in units of grams $CO_2$eq per million BTUs (MMBTU) of energy in the fuel. Under LCFS, GHG emissions are measured in units of grams $CO_2$eq per MJ of energy in the fuel and are referred to as carbon intensity or CI.

In general, the life cycle GHG emissions of the biogenic carbon-based fuel are compared to the life cycle GHG emissions for gasoline, referred to as a gasoline baseline. GHG life cycle emissions are compared by reference to the use of gasoline per unit of fuel energy.

The EPA value for the gasoline baseline used in life cycle GHG emission calculations is 98,204 g $CO_2$eq/MMBTU or 93.10 g $CO_2$eq/MJ. Under California's LCFS, the gasoline baseline is 95.86 g $CO_2$eq/MJ. Those of ordinary skill in the art can readily convert values herein from g $CO_2$eq/MJ to g $CO_2$eq/MMBTU or g $CO_2$eq/MMBTU to g $CO_2$eq/MJ by using an appropriate conversion factor.

The life cycle GHG emission reduction relative to a gasoline baseline is calculated using "EPA methodology", which means determining life cycle GHG emissions reductions by known methods as disclosed in EPA-420-R-10-006, "Renewable Fuel Standard Program (RFS2) Regulatory Impact Analysis", February 2010, which is incorporated herein by reference. In addition, for situations in which fossil carbon dioxide is introduced underground, such determination of life cycle GHG emission reduction includes a GHG saving that corresponds to the amount of carbon dioxide introduced underground. For example, one tonne of fossil carbon dioxide introduced underground would be counted as one tonne GHG savings in a life cycle GHG emission calculation. As would be appreciated by those of skill in the art, this method has been used by the EPA to quantify GHG savings due to the introduction of CO2 underground that is captured from power plants. (See EPA-HQ-OAR-2013-0495, Jan. 8, 2014).

According to a further embodiment of the invention, the life cycle GHG emission reduction relative to a gasoline baseline can be measured using "LCFS methodology", which means measuring life cycle GHG emissions reductions by California's LCFS methodology using the GREET model, as set forth in Detailed California-Modified GREET Pathway for Corn Ethanol, California Environmental Protection Agency, Air Resources Board, Jan. 20, 2009, Version 2.0.

According to one embodiment of the invention, the life cycle carbon dioxide emissions, rather than the life cycle GHG emissions, are determined for the biogenic carbon-based fuel and compared to a gasoline baseline. For example, as would be appreciated by those of skill in the art, when a reduction in carbon dioxide emissions relative to a production process baseline is quantified, a life cycle carbon dioxide emission reduction can be quantified instead of a life cycle GHG emission reduction.

Meeting Renewable and Low Carbon Fuel Targets

Advantageously, many processes described herein provide a methodology for meeting renewable fuel targets or mandates established by governments, including legislation and regulations for transportation or heating fuel sold or introduced into commerce in the United States. Examples of such legislation include the Energy Independence and Security Act ("EISA") and California AB 32—The Global Warming Solutions Act, which respectively established an RFS and a Low Carbon Fuel Standard (LCFS). For example, under EISA, the mandated annual targets of renewable content in fuel are implemented through an RFS that uses tradable credits (called Renewable Identification Numbers, referred to herein as "RINs") to track and manage the production, distribution and use of renewable fuels for transportation or other purposes. Targets under the LCFS can be met by trading of credits generated from the use of fuels with a lower GHG emission value than the gasoline baseline.

The term "credit", "renewable fuel credit" or "biofuel credit" means any rights, credits, revenues, greenhouse gas rights or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract or otherwise. According to one embodiment of the invention, the renewable fuel credit is a certificate, record, serial number or guarantee, in any form, including electronic, which evidences production of a quantity of fuel meeting certain life cycle GHG emission reductions relative to a baseline set by a government authority. The baseline is typically a gasoline baseline. Non-limiting examples of credits include RINs and LCFS credits in the United States.

The fuel credit may be generated in connection with the biogenic carbon-based fuel that is used as a transportation or heating fuel. According to an embodiment of the invention, a fuel credit is generated or caused to be generated with respect to the use of methane or ethanol as a transportation or heating fuel.

The fuel credit can be generated or caused to be generated with respect to a biogenic carbon-based fuel that is the product produced from the biogenic carbon dioxide and fossil derived hydrogen, or a fuel derived therefrom. The second product can be a gaseous or liquid fuel at 20° C. and includes hydrocarbon fuels such as methane or gasoline or alcohols such as methanol or ethanol.

The fuel credit can also be generated or caused to be generated with respect to a biogenic carbon-based fuel produced from the production process in which biogenic carbon dioxide is collected and used to produce the biogenic carbon-based fuel, fuel intermediate or chemical product. For example, a fuel credit can be generated with respect to methane sourced from biogas, which in turn is produced from anaerobic digestion of a stream from the production process in which the biogenic carbon dioxide is collected and used to make the second product.

In one embodiment, the biogenic carbon-based fuel of the invention could qualify for an advanced biofuel RIN under EISA having a D code of 3, 4, 5 or 7. In a further embodiment, the product of the invention is eligible for a RIN having a D code of 3 or 5. Under the LCFS, products for use as fuels with greater reductions in life cycle GHG emissions qualify for a greater number of credits having higher market value than fuels with lower reductions.

Energy policy, including EISA and LCFS, and the generation of renewable fuel credits under each of these legislative frameworks, is discussed in turn below.

(a) Meeting Renewable Fuel Targets Under EISA

U.S. policymakers have introduced a combination of policies to support the production and consumption of biofuels, one of which includes the RFS. The RFS originated with the Energy Policy Act of 2005 (known as RFS1) and was expanded and extended by the EISA of 2007. The RFS expanded and extended under EISA is sometimes referred to as RFS2 or RFS as used herein.

Under the EISA, the RFS sets annual mandates for renewable fuels sold or introduced into commerce in the United States through 2022 for different categories of biofuels (see Table 2 below). There is an annually increasing schedule for minimum aggregate use of total renewable biofuel (comprised of conventional biofuels and advanced biofuels), total advanced biofuel (comprised of cellulosic biofuels, biomass-based diesel, and other advanced biofuels), cellulosic biofuel and bio-based diesel. The RFS mandates are prorated down to "obligated parties", including individual gasoline and diesel producers and/or importers, based on their annual production and/or imports.

Each year, obligated parties are required to meet their prorated share of the RFS mandates by accumulating credits known as RINs, either through blending designated quantities of different categories of biofuels, or by purchasing from others the RINs of the required biofuel categories.

The RIN system was created by the EPA to facilitate compliance with the RFS. Credits called RINs are used as a currency for credit trading and compliance. RINs are generated by producers and importers of renewable biofuels and assigned to the volumes of renewable fuels transferred into the fuel pool. RINs are transferred with a fuel through the distribution system until they are separated from the fuel by parties who are entitled to make such separation (generally refiners, importers, or parties that blend renewable fuels into finished fuels). After separation, RINs may be used for RFS compliance, held for future compliance, or traded. There is a centralized trading system administered by the U.S. EPA to manage the recording and transfer of all RINs.

According to certain embodiments of the invention, a RIN may be characterized as numerical information. The RIN numbering system was in the format KYYYYCCCCFFFFF-BBBBBRRDSSSSSSSSEEEEEEEE where numbers are used to designate a code representing whether the RIN is separated from or attached to a specific volume (K), the calendar year of production or import (YYYY), Company ID (CCCC), Facility ID (FFFFF), Batch Number (BBBBB), a code for fuel equivalence value of the fuel (RR), a code for the renewable fuel category (D), the start of the RIN block (SSSSSSSS) and the end of the RIN block (EEEEEEEE). Under current regulations, a RIN contains much of the foregoing information and other information in the form of data elements that are introduced into a web-based system administered by the EPA known as the EPA Moderated Transaction System, or "EMTS". It should be appreciated, however, that the information required for RIN generation and/or the format of the information may change depending on prevailing regulations.

The D code of a RIN specifies the fuel type, feedstock and production process requirements and thus in certain embodiments of the invention the D code may be used to characterize the type of RIN, as described hereinafter. The D code of a RIN is assigned a value between 3 and 7 under current regulations. The value assigned depends on the fuel type, feedstock and production process requirements as described in Table 1 to 40 C.F.R. § 80.1426. Examples of fuels assigned a D code of 3-7 under current regulations are provided below. These examples are for illustration purposes only and are not to be considered limiting to the invention.

TABLE 1

RIN D code examples

| D code | Fuel Type | Example |
|---|---|---|
| 3 | Cellulosic biofuel | Ethanol from cellulosic biomass from agricultural residues |
| 4 | Biomass-based diesel | Biodiesel and renewable diesel from soy bean oil |
| 5 | Advanced biofuel | Ethanol from sugarcane |
| 6 | Renewable fuel (conventional biofuel) | Ethanol from corn starch |
| 7 | Cellulosic diesel | Diesel from cellulosic biomass from agricultural residues |

As described previously, the RFS2 mandate volumes are set by four separate but nested category groups, namely renewable biofuel, advanced biofuel, cellulosic biofuel and biomass-based diesel. The requirements for each of the nested category groups are provided in Table 2.

The nested category groups are differentiated by the D code of a RIN. To qualify as a total advanced biofuel, the D code assigned to the fuel is 3, 4, 5 or 7, while to qualify as cellulosic biofuel the D code assigned to the fuel is 3 or 7 (Table 2).

According to current regulations, each of the four nested category groups requires a performance threshold in terms of GHG reduction for the fuel type. In order to qualify as a renewable biofuel, a fuel is required to meet a 20% life cycle GHG emission reduction (or be exempt from this requirement), while advanced biofuel and biomass-based diesel are required to meet a 50% life cycle GHG emission reduction and cellulosic biofuels are required meet a 60% life cycle GHG emission reduction, relative to a gasoline baseline. As well, each nested category group is subject to meeting certain feedstock criteria.

TABLE 2

Nested category groups under RFS2

| Nested category group | Fuel type | Life cycle GHG threshold reduction relative to gasoline baseline |
|---|---|---|
| Renewable biofuel | Conventional biofuels (D code 6) and advanced biofuels (D code 3, 4, 5 or 7) | 20% |
| Advanced biofuel | Cellulosic biofuels (D code 3 or 7), biomass-based diesel (D code 4 or 7), and other advanced biofuels (D code 5) | 50% |
| Cellulosic biofuels | Biofuel derived from cellulosic material (D code 3) and bio-diesel derived cellulosic material (D code 7). | 60% |
| Biomass-based diesel | Conventional biodiesel (D code 4) or cellulosic diesel (D code 7) | 50% |

Thus, according to certain embodiments of the invention, a RIN credit containing information or a value corresponding to a reduction in life cycle GHG emissions relative to a baseline is generated with the production of a volume of biogenic carbon-based fuel produced by the process. The information may correspond to a reduction in life cycle GHG emissions of at least 40%, 45%, 50%, 55%, 60%, 65%, 70%, 75%, 80% or 85% relative to a gasoline baseline. In one embodiment, the processes described herein may contribute wholly or in part to achieving reductions in the life cycle GHG emissions of a biogenic carbon-based fuel relative to a gasoline baseline.

The RIN associated with biogenic carbon-based fuel may be assigned a D code of 3, 4, 5 or 7, also referred to herein as a D3, D4, D5 and D7 RIN, respectively. According to certain embodiments, the RIN associated with the biogenic carbon-based fuel may be assigned a D code of 3 or 5. Under current regulations, this corresponds to cellulosic biofuel and advanced biofuel fuel types, which meet GHG emissions reductions of 60% and 50%, respectively, relative to a gasoline baseline.

According to some embodiments, the fuel credit is characterized as containing numerical information associated with the one or more products produced by the process of the invention for use as a transportation or heating fuel. Thus, a party may generate a fuel credit comprising numerical information relating to one or more products of the process representing at least one parameter selected from (i) the type of transportation or heating fuel; (ii) the year in which the product was produced; (iii) a registration number associated with the producer or importer; and (iv) serial number associated with a batch. In a further embodiment, at least two parameters or at least three parameters are selected from the foregoing list. The numerical information may also include one or more of the following parameters selected from: (i') a number identifying that the numerical information is assigned to a volume of the product, or separated; (ii') a registration number associated with the facility at which the product was produced or imported; (iii') a number representing a value related to an equivalence value of the product; (iv') a number representing a first-volume numerical information associated with a batch of the product; and (v') a number representing a last-volume numerical information associated with a batch of the product.

The RIN or numerical information described herein or a portion thereof is provided to a government regulatory agency, including the EPA, in connection with generating a RIN. In some embodiments of the invention, the numerical information is also provided to a purchaser of the biogenic carbon-based fuel produced by the invention. The numerical information described herein or portions thereof may be stored electronically in computer readable format.

The purchaser of the biogenic carbon-based fuel may separate the RIN. As described above, separation of a RIN from a volume of the biogenic carbon-based fuel for use as a transportation or heating fuel, means termination of the assignment of the RIN to a volume of fuel. RIN separation is typically carried out by a fuel blender, importer or other obligated party. According to pre-2010 regulations, when a RIN is separated, the K code of the RIN is changed to 2.

Separation of RINs may be conducted in accordance with prevailing rules and regulations, as currently provided in 40 C.F.R. § 80.1129 and 40 C.F.R. § 80.1429. RINs generated in accordance with the processes described herein may be separated and subsequently traded.

It should be understood that the regulations under EISA, including RIN requirements and the criteria for categorization of a fuel under a particular fuel category, such as life cycle GHG emission thresholds, are described herein in accordance with current regulations and can be readily ascertained by those of skill in the art.

(b) Low Carbon Fuel Standard (LCFS)

The beneficial GHG emissions reductions achieved by the present invention can provide a means for meeting low carbon fuel standards established by jurisdictions within the United States or other government authorities. The credit, which includes a certificate, may be associated with the biogenic carbon-based fuel, and represents or is proportional to the amount of life cycle GHG emissions reduced measured relative to a gasoline baseline. As set forth previously, the life cycle GHG emissions under low carbon fuel standards are often referred to as carbon intensity or CI.

California's LCFS currently requires that all mixes of fuel that oil refineries and distributors sell in the Californian market meet in aggregate the established targets for GHG emissions reductions. California's LCFS requires increasing annual reductions in the average life cycle emissions of most transportation fuels, up to a reduction of at least 10% in the carbon intensity, which is a measure of the life cycle GHG emissions, by 2020. Targets can be met by trading of credits generated from the use of fuels with a lower GHG emission value than gasoline baseline. Similar legislation has been implemented by the province of British Columbia, Canada, the United Kingdom and by the European Union.

According to some embodiments, LCFS fuel credit generation comprises generating information associated with the one or more products produced by the process of the invention for use as a transportation or heating fuel. A party may generate information relating to at least one parameter selected from (i) a reporting period; (ii) a fuel pathway code; (iii) transaction information, including type or date of a transaction; (iv) fuel production facility information; (v) fuel delivery methods; (vi) an amount of fuel used as a fossil fuel replacement, such as gasoline or diesel; and (vii) credits or deficits generated. In a further embodiment, information regarding at least two parameters, at least three parameters or at least four parameters is generated from the foregoing list.

British Columbia, a province in Canada, approved a Renewable and Low Carbon Fuel Requirements Act, which requires parties who manufacture or import the fuel into the province ensure that the renewable content and the average carbon intensity of the fuel they supply meets levels set by regulations. Fuel suppliers are required to submit annual reports regarding the renewable fuel content and carbon intensity of the transportation fuels they supply. The province allows transfers of GHG credits between fuel suppliers to provide flexibility in meeting the requirements of the regulation.

In the European Union, GHG emissions are regulated by a Fuel Quality Directive, 98/70/EC. In April 2009, Directive 2009/30/EC was adopted which revises the Fuel Quality Directive 98/70/EC. The revisions include a new element of legislation under Article 7a that requires fuel suppliers to reduce the GHG intensity of energy supplied for road transport (Low Carbon Fuel Standard). In particular, Article 7a specifies that this reduction should amount to at least 6% by 31 Dec. 2020, compared to the EU-average level of life cycle GHG emissions per unit of energy from fossil fuels in 2010. According to the Fuel Quality Directive, fuel/energy suppliers designated by member states of the European Union are required to report to designated authorities on: (a) the total volume of each type of fuel/energy supplied, indicating where the fuel/energy was purchased and its origin; and (b) the life cycle GHG emissions per unit of energy. The European Union has also promoted the use of biofuels through a Biofuel Directive (2003/30/EC), which mandates countries across the EU to displace certain percentages of transportation fuel with biofuels by target dates.

The United Kingdom has a Renewable Transport Fuel Obligation (RTFO) in which biofuel suppliers are required to report on the level of carbon savings and sustainability of the biofuels they supplied in order to receive Renewable Transport Fuel Certificates (RTFCs). Suppliers report on both the net GHG savings and the sustainability of the biofuels they supply according to the appropriate sustainability standards of the feedstocks from which they are produced and any potential indirect impacts of biofuel production, such as indirect land-use change or changes to food and other commodity prices that are beyond the control of individual suppliers. Suppliers that do not submit a report will not be eligible for RTFCs.

Certificates can be claimed when renewable fuels are supplied and fuel duty is paid on them. At the end of the obligation period, these certificates may be redeemed to the RTFO Administrator to demonstrate compliance. Certificates can be traded and if obligated suppliers do not have a sufficient amount of certificates at the end of an obligation period they may "buy-out" the balance of their obligation by paying a buy-out price.

The present invention has been described with regard to one or more embodiments. However, it will be apparent to those of skill in the art that a number of variations and modifications can be made without departing from the scope of the invention as defined in the claims.

EXAMPLES

Example 1

Producing Biogenic Ethanol Using Fossil Derived Hydrogen and Biogenic Carbon Dioxide In this example, biogenic carbon dioxide and fossil derived hydrogen are fed to a bioreactor and fermented to ethanol by *Clostridium ljungdahlii* bacteria that carry out the following bioconversion:

$$6H_2 + 2CO_2 \rightarrow CH_3CH_2OH + 3H_2O.$$

The hydrogen for the foregoing reaction is produced by a hydrogen production process using fossil methane as the feedstock. Fossil carbon dioxide produced from the hydrogen production that is otherwise vented is introduced underground to reduce life cycle GHG emissions of the final fuel/fuel intermediate. The process flow sheet is described below in relation to FIG. 1.

As shown in FIG. 1, corn is the feed to a dry milling process employing fermentation 10 to produce biogenic ethanol. The corn is first treated by grinding and enzyme treatment in a slurry. The resultant slurry is then fed to fermentation unit 10 and fermented with *Saccharomyces cerevisiae* yeast to produce ethanol and a biogenic $CO_2$ stream 20, which is purified. In this example, the $CO_2$ stream 20 is assumed to contain 100 mole % $CO_2$ (Table 3). The biogenic $CO_2$ stream 20 is combined with fossil derived hydrogen stream 30 to produce a combined stream 40 comprising biogenic $CO_2$ and fossil derived hydrogen.

A first step involved in producing the fossil derived hydrogen stream 30 involves feeding fossil methane stream 45 to a steam methane reformer (SMR) unit 50. The amount of methane in the fossil methane feed stream 45 to the SMR unit 50 is 92.9 mol % (Table 3). In the steam methane reformer unit 50, the methane is converted to carbon monoxide and hydrogen by the following reaction with water to produce an SMR outlet stream 60 comprising carbon monoxide and hydrogen:

$$CH_4 + H_2O \rightarrow CO + 3H_2.$$

The SMR outlet stream 60 from the steam methane reformer unit 50 thus contains not only hydrogen from a fossil source, but also fossil carbon in the form of carbon monoxide. The fossil carbon monoxide in SMR outlet stream 60 is subsequently reacted with water to produce fossil carbon dioxide and additional hydrogen in a water gas shift (WGS) unit 70 as per the following reaction.

$$CO + H_2O \rightarrow CO_2 + H_2.$$

The water gas shift unit 70 increases the yield of hydrogen from fossil methane, while converting the fossil CO to fossil carbon dioxide. In this example, the water gas shift reaction in the water gas shift unit 70 comprises both a high and a low temperature shift (not shown). The overall conversion of fossil methane to carbon dioxide and hydrogen is as follows:

$$\text{Overall: } CH_4 + 2H_2O \rightarrow CO_2 + 4H_2.$$

An outlet stream 80 from the water gas shift unit 70 is then treated to remove carbon dioxide in carbon dioxide recovery unit 85 to produce a carbon dioxide-depleted stream 86 and a fossil carbon dioxide stream 87 that is eventually introduced underground for enhanced oil recovery (EOR) 100 as described below. The carbon dioxide-depleted stream 86 is fed to a pressure swing adsorption (PSA) unit 90. The pressure swing adsorption unit 90 separates the hydrogen that originates from fossil fuel from any remaining fossil carbon dioxide and other non-hydrogen components such as methane and carbon monoxide. This produces the stream 30 that is enriched in fossil derived hydrogen and a purge stream 91 containing fossil carbon dioxide. In this example, the stream 30 comprises 99.9 mol % hydrogen (Table 3). Although carbon dioxide recovery from stream 80 is shown, carbon dioxide can be recovered from other stages of the hydrogen production process. (See FIG. 7, for example locations A, B or C). In this example, a purge stream 91 remaining after carbon dioxide removal is introduced to the furnace of the steam methane reformer unit 50 to provide heat energy to the unit.

The recovered fossil carbon dioxide is introduced to a pipeline (not shown) for transporting carbon dioxide. Carbon dioxide is withdrawn from the pipeline (not shown), typically by another party through a contractual arrangement, and then introduced underground to recover oil as part of an enhanced oil recovery operation (EOR) 100. By introducing the fossil carbon dioxide underground, the life cycle GHG emissions associated with the biogenic ethanol produced by the process can be significantly reduced.

The fossil derived hydrogen stream 30 comprising 99.9% mol % hydrogen is combined with the biogenic $CO_2$ stream 20 as described previously to form a stream 40 and fed to a fermentation bioreactor 110. In another embodiment (not illustrated), the fossil derived hydrogen stream 30 and the biogenic $CO_2$ stream 20 are fed separately to the fermentation bioreactor 110. In the fermentation bioreactor 110 the biogenic carbon dioxide and fossil derived hydrogen are fermented to ethanol by *Clostridium ljungdahlii* bacteria. A fermented stream 120 is withdrawn from the fermentation bioreactor 110 and fed to a distillation unit 130 to produce concentrated biogenic ethanol 115, which is further concentrated beyond its azeotropic breaking point by molecular sieves (not shown).

Material balances for the fossil methane feed 45, the fossil derived hydrogen stream 30 and biogenic $CO_2$ stream 20 are provided in Table 3 below. These values were used to calculate the life cycle GHG emissions of the biogenic ethanol relative to a gasoline baseline, which is discussed below in Example 2.

Table 3 also shows the calculated increase in theoretical yield of biogenic ethanol from the process described in FIG. 1 relative to the methane feed, referred to hereinafter as the "biogenic ethanol efficiency" or "efficiency". The efficiency achieved by the above-described process relative to the fossil methane feed is 58% (mmBTU of ethanol/mmBTU of fossil methane feed). The calculations assume the yield in gas fermentation is 81%. The assumed recoverable $CO_2$ from the ethanol plant is 5.3 lbs of $CO_2$ for each gallon of ethanol produced. These assumptions were also made in calculating the life cycle GHG emission reductions for this example and in the subsequent examples.

TABLE 3

Material balance, mass ratio, biogenic ethanol efficiency and energy inputs and outputs for ethanol produced using a hydrogen enriched stream and fossil $CO_2$ introduction underground

|  |  | Fossil methane feed | PSA outlet $H_2$ stream | Biogenic $CO_2$ stream | Non-biogenic ethanol produced | Biogenic ethanol produced |
|---|---|---|---|---|---|---|
| Stream No. (FIG. 1) | | 45 | 30 | 20 | 115 | 115 |
| *Material balance* | | | | | | |
| $H_2$ | mol % | 2.9 | 99.9 | | | |
| CO | mol % | | | | | |
| $CO_2$ | mol % | 1.9 | | 100.0 | | |
| $CH_4$ | mol % | 92.2 | 0.1 | | | |
| $N_2$ | mol % | 2.4 | | | | |
| $H_2O$ | mol % | 0.5 | | | | |
| Ethanol | mol % | | | | 0 | 100.0 |
| TOTAL | mol % | 100.0 | 100.0 | 100.0 | 0.0 | 100.0 |
| *Mass ratios* | | | | | | |
| lb/mmBTU of fossil methane feed | | 46.5 | 16.2 | 117.6 | — | 49.8 |
| *Biogenic ethanol efficiency* | | | | | | |
| Gallons ethanol/mmBTU of fossil methane feed | | | | | | 7.6 |
| *Energy input/output* | | | | | | |
| mmBTU/ mmBTU of fossil methane feed | | 100% | 83% | | 0% | 58% |

Example 2

Comparison of GHG Emission Calculations for a Process with a Water Gas Shift and Introduction of Fossil $CO_2$ Underground Versus a Process without Such Steps The life cycle GHG emissions of the process described in Example 1 and FIG. 1 relative to a gasoline baseline were calculated and are summarized in Table 4 below. The calculations show that by using the hydrogen enriched stream 30 produced by the hydrogen production process outlined in Example 1 in the above-described ethanol fermentation, and by introducing fossil carbon dioxide stream 87 from the hydrogen production underground to extract oil, the life cycle GHG emissions for the total ethanol produced can be reduced by 24% relative to a gasoline baseline.

TABLE 4

Summary of life cycle GHG emissions for ethanol produced using a hydrogen enriched stream and fossil $CO_2$ introduction underground

| | Usage | Emission intensity | Emissions from fuel |
|---|---|---|---|
| Units | BTU/gal ethanol produced | g $CO_2$eq/mmBTU fuel used | g $CO_2$eq/mmBTU ethanol produced |
| Natural gas usage (SMR feed) | 132,325 | 68,575 | 117,847 |
| Electricity usage | 9,261 | 219,812 | 26,438 |
| $CO_2$ recovered from SMR production (credit) | | | (69,535) |
| Tailpipe emissions | | | 0 |
| TOTAL | | 141,586 | 74,749 |
| Life cycle GHG emission reduction relative to the gasoline baseline* | | | 24% |

*98,204 g $CO_2$eq/mmBTU ethanol produced obtained from 2010 Final Rule-Federal Register/Vol. 75, No. 58/Friday, Mar. 26, 2010/Rules and Regulations As noted above, the ethanol in this example contains only biogenic carbon, and therefore, when the fuel is burned in an internal combustion engine, no fossil carbon is emitted to the atmosphere. Consequently, as can be seen in Table 4 above, these emissions need not be accounted for in the life cycle emission calculations. Moreover, GHG emission reductions result by introducing fossil carbon dioxide from hydrogen production underground. The fossil carbon dioxide recovered from SMR production and introduced underground results in a credit of 69,535 g $CO_2$eq/mmBTU ethanol produced.

Adding up the emission debits and credits gave a total life cycle emission value of 74,749 g $CO_2$eq/mmBTU ethanol produced, which represents the above-noted 24% reduction relative to the gasoline baseline of 98,204 g $CO_2$eq/mmBTU ethanol produced.

For comparison, similar calculations were performed for a process otherwise identical to FIG. 1, but that omits the water gas shift 70, fossil carbon dioxide removal 85, the pressure swing adsorption unit 90 and the introduction of fossil carbon dioxide from the process underground to extract oil in an enhanced oil recovery (EOR) operation 100. In such comparative process, a syngas stream comprising fossil carbon and hydrogen instead of a stream enriched in hydrogen is fed to the fermentation bioreactor. There is no credit for $CO_2$ recovered from SMR production and introduced underground. The calculations described below show that the ethanol produced by this process does not have a favourable GHG emission balance and in fact results in an increase in the life cycle GHG emissions relative to a gasoline baseline.

Figure 2:
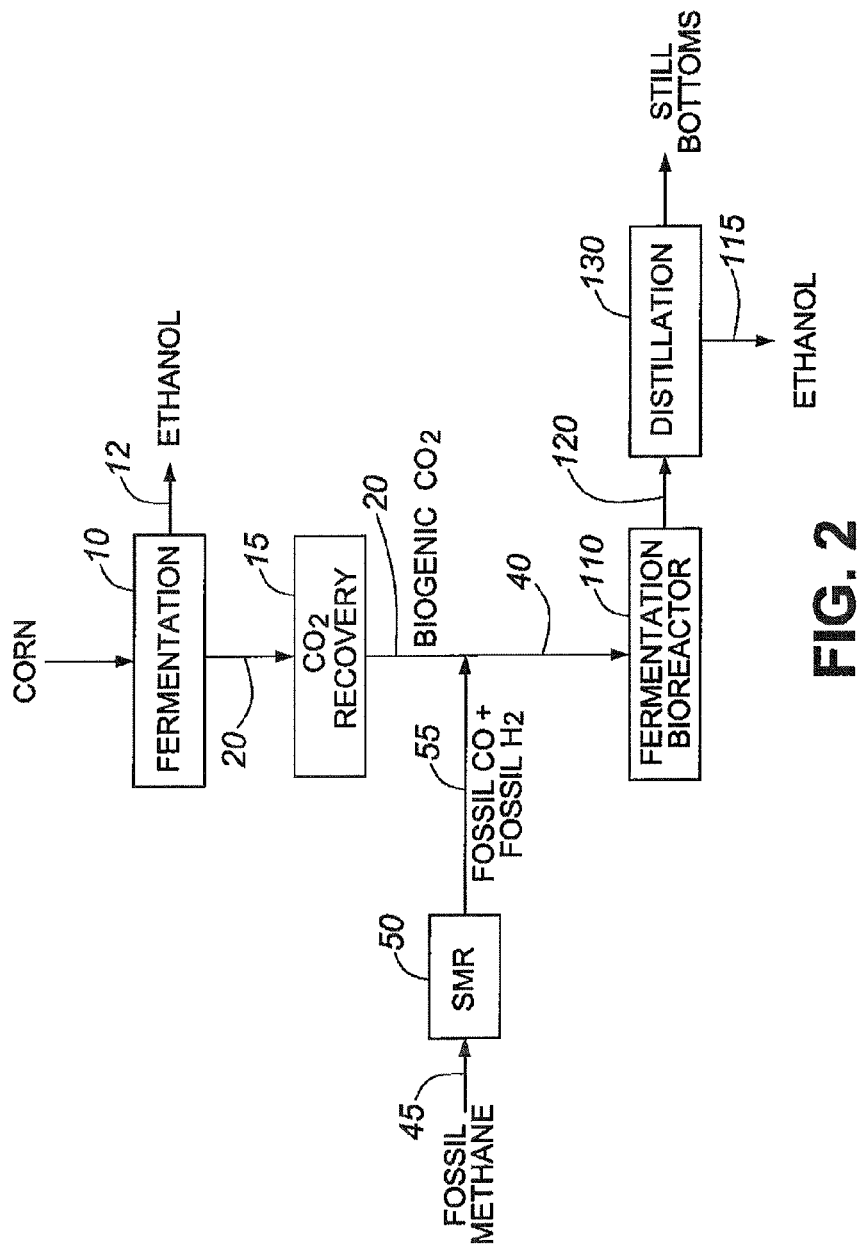
FIG. 2 is a process flow diagram showing the production of ethanol using syngas from fossil fuel and biogenic carbon dioxide.

The flowsheet for this latter comparative process is depicted in FIG. 2. Like reference numbers among FIGS. 1 and 2 represent identical or similar process steps or unit operations.

Similar to FIG. 1, in the comparative process depicted in FIG. 2, corn is the feed to a process employing fermentation to produce ethanol. The corn is treated by grinding and enzyme treatment in a slurry (not shown). The slurry is then fermented in fermentation 10 with *Saccharomyces cerevisiae* yeast to produce ethanol 12 and biogenic $CO_2$ stream 20 with $CO_2$ recovery 15.

However, unlike the process depicted in FIG. 1, the biogenic $CO_2$ stream 20 is combined with a fossil syngas stream 55. The syngas stream 55 results from the conversion of fossil methane 45 to fossil carbon monoxide and fossil hydrogen by a steam methane reforming unit 50 in which the following reaction is carried out:

$$CH_4 + H_2O \rightarrow CO + 3H_2.$$

Because no water gas shift reaction occurs and no $CO_2$ is introduced underground, the stream 55 blended with stream 20 contains not only hydrogen from a fossil source, but also fossil carbon in the form of carbon monoxide. The fossil syngas stream 55 composition is provided in Table 5 below and contains 49.1 mol % fossil hydrogen and 9.7 mol % carbon monoxide (wet basis).

The stream 55 comprising fossil syngas is subsequently combined with biogenic $CO_2$ stream 20 to produce a combined stream 40 comprising fossil carbon monoxide, hydrogen and carbon dioxide from fossil fuel and biogenic carbon dioxide.

In the fermentation bioreactor 110 illustrated in FIG. 2 the biogenic carbon dioxide from stream 20 and the syngas from stream 55 (comprising carbon monoxide, carbon dioxide and hydrogen from fossil fuel) are fermented to ethanol by *Clostridium ljungdahlii* bacteria. The following reactions occur to produce ethanol:

$$6CO + 3H_2O \rightarrow CH_3CH_2OH + 4CO_2$$

$$6H_2 + 2CO_2 \rightarrow CH_3CH_2OH + 3H_2O.$$

Since the carbon monoxide and carbon dioxide in the fossil syngas stream 55 are fossil derived, for the comparative process illustrated in FIG. 2, the first reaction will produce ethanol and carbon dioxide comprising fossil carbon. The fossil carbon dioxide that is produced by the first reaction will go on to produce ethanol which contains fossil carbon. As a result, a significant portion of the ethanol in stream 115 will contain fossil carbon and thus will need to be accounted for in the form of tailpipe emissions upon combusting the ethanol in vehicles.

Similar to FIG. 1, FIG. 2 illustrates a fermented solution stream 120 that is withdrawn from the fermentation bioreactor 110 and fed to distillation unit 130 to produce the concentrated ethanol in stream 115, which is further concentrated beyond its azeotropic breaking point by molecular sieves (not shown).

Material balance and other assumptions made for the life cycle GHG emission calculations, as well as ethanol efficiency calculations, for the process of FIG. 2 are described in Table 5 below.

TABLE 5

Material balance, mass ratio, biogenic ethanol efficiency and energy inputs and outputs for ethanol produced using fossil syngas from SMR and without fossil $CO_2$ introduction underground

|  |  | Fossil methane feed | Fossil syngas stream | Biogenic $CO_2$ stream | Non-biogenic ethanol produced | Biogenic ethanol produced |
|---|---|---|---|---|---|---|
| Stream No. (FIG. 2) |  | 45 | 55 | 20 | 115 | 115 |
| $H_2$ | mol % | 2.9 | 49.1 |  |  |  |
| CO | mol % |  | 9.7 |  |  |  |
| $CO_2$ | mol % | 1.9 | 5.4 | 100.0 |  |  |
| $CH_4$ | mol % | 92.2 | 4.1 |  |  |  |
| $N_2$ | mol % | 2.4 | 0.0 |  |  |  |
| $H_2O$ | mol % | 0.5 | 31.7 |  |  |  |
| Ethanol | mol % |  |  |  | 100.0 | 100.0 |
| TOTAL | mol % | 100.0 | 100.0 | 100.0 | 100.0 | 100.0 |

TABLE 5-continued

Material balance, mass ratio, biogenic ethanol efficiency and energy inputs and outputs for ethanol produced using fossil syngas from SMR and without fossil $CO_2$ introduction underground

|  | Fossil methane feed | Fossil syngas stream | Biogenic $CO_2$ stream | Non-biogenic ethanol produced | Biogenic ethanol produced |
|---|---|---|---|---|---|
| Mass ratios |  |  |  |  |  |
| lb/mmBTU of fossil methane feed | 46.5 | 187 | 29.9 | 42.4 | 12.7 |
| Biogenic ethanol efficiency |  |  |  |  |  |
| Gallons ethanol/mmBTU of fossil methane feed |  |  |  | 6.4 | 1.9 |
| Energy input/output |  |  |  |  |  |
| mmBTU/mmBTU of fossil methane feed | 100% | 117% |  | 50% | 15% |

The life cycle GHG emissions of the process described FIG. 2 relative to a gasoline baseline are summarized in Table 6 below.

TABLE 6

Summary of life cycle GHG emissions for ethanol produced using syngas from SMR and without fossil $CO_2$ introduction underground

|  | Usage | Emission intensity | Emissions from fuel |
|---|---|---|---|
|  | Units |  |  |
|  | BTU/gal ethanol produced | g $CO_2$eq/mmBTU fuel used | g $CO_2$eq/mmBTU ethanol produced |
| Fossil methane usage (SMR feed) | 119,639 | 68,575 | 106,549 |
| Electricity Usage | 9,261 | 219,812 | 26,438 |
| Tailpipe emissions from fossil carbon combustion |  |  | 71,247 |
| TOTAL | 128,900 |  | 204,234 |
| Life cycle GHG emission reduction relative to the gasoline baseline* |  |  | −108% |

*98,204 g $CO_2$eq/mmBTU ethanol produced obtained from 2010 Final Rule-Federal Register/Vol. 75, No. 58/Friday, Mar. 26, 2010/Rules and Regulations The above calculations show that by using a syngas stream from a steam methane reforming process in an ethanol fermentation, without a water gas shift, or carbon dioxide purification and without introducing any fossil carbon dioxide underground, the life cycle GHG emissions are actually increased by 108% relative to a gasoline baseline (depicted as —108% relative to a gasoline baseline in Table 6). Such increases in GHG emissions result in part from the need to account for tailpipe emissions from fossil carbon combustion, which are 71,247 g $CO_2$eq/mmBTU ethanol produced, and also the absence of a credit associated with recovering $CO_2$ from SMR production and introducing it underground.

Therefore, by implementing an embodiment of the invention with the steps of $CO_2$ disposition, and using a hydrogen enriched stream from fossil sources, significant GHG emission reductions relative to a gasoline baseline can be realized in comparison to a process without implementing such steps.

A further advantage that becomes evident from comparing the ethanol efficiency results in Table 3 with Table 5 is that by carrying out the embodiment of the invention depicted in FIG. 1, the efficiency of producing biogenic ethanol is greatly increased relative to the comparative process of FIG. 2. As noted, by using the hydrogen enriched stream to produce the biogenic ethanol and by introducing the fossil carbon dioxide underground, the amount of biogenic ethanol energy produced relative to the methane feed energy is 58%. In contrast, the comparative process depicted in FIG. 2 only resulted in an efficiency of 15% biogenic ethanol. This is because in this latter process, the majority of the ethanol produced is non-biogenic (23% biogenic and 77% fossil). Not only does this require accounting for tailpipe emissions, which increases GHG emissions, but also the majority of the fuel product may not be considered renewable in some jurisdictions, which in turn may reduce its environmental and commercial value.

Example 3

GHG Emission Calculations of an Embodiment Employing Displacement

In this example, life cycle GHG emissions were calculated for a process in which biogenic carbon dioxide is sourced from a fermentation conducted as part of a cellulosic ethanol conversion process. The biogenic carbon dioxide collected is combined with fossil derived hydrogen and fermented to produce biogenic ethanol as described previously in Example 1.

In the cellulosic ethanol conversion process, lignin is combusted to produce steam and electricity for the cellulosic ethanol plant and the excess energy is sold to the electricity grid. The electricity derived from non-fossil organic material displaces the production or use of fossil derived electricity from a coal burning power plant.

Figure 3:
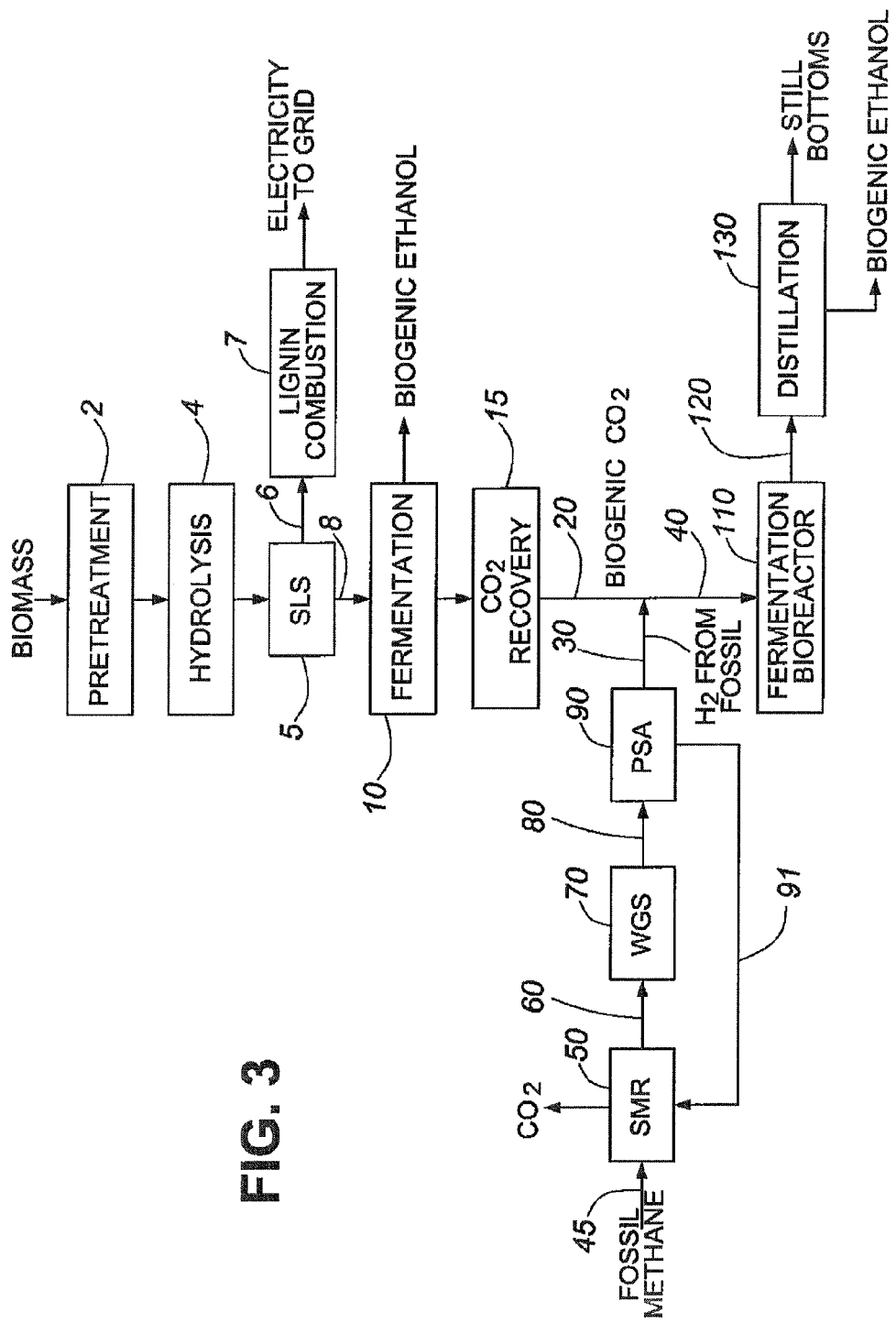
FIG. 3 is a process flow diagram showing the production of biogenic ethanol using fossil derived hydrogen and biogenic carbon dioxide in a process in which electricity derived from lignin displaces fossil derived electricity from a coal burning power plant.

The process flow diagram is shown in FIG. 3. Like reference numbers among FIGS. 1, 2 and 3 represent identical or similar process steps or unit operations.

As shown in FIG. 3, biomass is subjected to a pretreatment 2 to make the biomass more amenable to enzymatic hydrolysis. Pretreatment of the biomass typically involves the addition of pretreatment chemical and heat to hydrolyze at least a portion of the hemicellulose component of the biomass. The pretreated biomass is then hydrolyzed with cellulase enzymes in hydrolysis unit 4 to produce glucose. The hydrolyzed material, comprising glucose and other hexose and pentose sugars, as well as unhydrolyzed, insoluble material comprising lignin, is fed to a solids-liquid-separation unit 5. The solids-liquid-separation (SLS) unit 5 produces a stream 6 comprising lignin and an aqueous stream 8 comprising sugar. The stream 6 comprising lignin is combusted in lignin combustion unit 7 to produce steam and electricity for the plant and the excess electricity is sent to the grid for external use, thereby displacing fossil derived electricity. The aqueous stream 8 comprising sugar is fed to a fermentation unit 10 to produce biogenic ethanol and biogenic carbon dioxide is collected by $CO_2$ recovery 15 to produce a biogenic $CO_2$ stream 20.

The biogenic $CO_2$ stream 20 is combined with a fossil derived hydrogen stream 30. The fossil derived hydrogen stream 30 is produced from fossil methane according to the process described in Example 1, except fossil carbon dioxide is not introduced underground in enhanced oil recovery to extract oil. A combined stream 40 comprising fossil derived hydrogen from stream 30 and biogenic carbon dioxide from stream 20 is fermented to biogenic ethanol in fermentation bioreactor 110. A fermented solution stream 120 is sent to distillation unit 130 to concentrate the biogenic ethanol.

The life cycle GHG emissions relative to a gasoline baseline for the foregoing process with displacement of fossil electricity with electricity derived (referred to as "export") from lignin combustion 7 were calculated. For comparison, the same GHG analysis was also performed on a process without such displacement (referred to as "no export"), but that is otherwise similar to the process outlined in FIG. 3. The avoidance of power export can typically be achieved by investing less in energy recovery equipment. The mass balance assumptions for the composition of the fossil methane to the SMR 50, the composition of the hydrogen enriched stream 30 and the biogenic $CO_2$ stream 20, as well as other assumptions described in Table 3 above, are the same as in Example 1.

The calculations were performed for two processes in which either switch grass or corn stover respectively were used as the feedstock. The results of the analysis with and without displacement by export of electricity for switch grass are presented in Table 7 and similar calculations for corn stover are presented in Table 8 below.

TABLE 7

Summary of life cycle GHG emissions for ethanol produced using a hydrogen enriched stream and fossil derived electricity displacement from lignin combustion with switch grass

| | Usage | Emission intensity | Emissions from fuel - no export | Emissions from fuel - export |
|---|---|---|---|---|
| | | | Units | |
| | BTU/gal ethanol produced | g CO2eq/mmBTU fuel used | g CO2eq/aggregate mmBTU ethanol produced | g CO2eq/aggregate mmBTU ethanol produced |
| Agriculture/Land Use | | | 298 | 298 |
| | Fuel Production (cellulosic ethanol and gas fermentation) | | | |
| Natural Gas | 33,628 | 68,575 | 29,949 | 29,949 |
| Electricity | 2,356 | 219,812 | 6,726 | 6,726 |
| Other | | | 2,968 | 2,968 |

TABLE 7-continued

Summary of life cycle GHG emissions for ethanol produced using a hydrogen enriched stream and fossil derived electricity displacement from lignin combustion with switch grass

|  | Usage | Emission intensity | Emissions from fuel - no export Units | Emissions from fuel - export |
|---|---|---|---|---|
|  | BTU/gal ethanol produced | g CO2eq/mmBTU fuel used | g CO2eq/aggregate mmBTU ethanol produced | g CO2eq/aggregate mmBTU ethanol produced |
| Fuel and Feedstock Transport |  |  | 2,238 | 2,238 |
| Tailpipe Emissions |  |  | 746 | 746 |
| Electricity export credit | (3,863) | 219,812 | — | (11,138) |
| TOTAL |  |  | 56,797 | 45,659 |
| Life cycle GHG emission reduction relative to the gasoline baseline** |  |  | 42% | 54% |

* 98,204 g $CO_2$eq/mmBTU ethanol produced obtained from 2010 Final Rule-Federal Register/Vol. 75, No. 58/Friday, Mar. 26, 2010/Rules and Regulations

TABLE 8

Summary of life cycle GHG emissions for ethanol produced using a hydrogen enriched stream and without electricity displacement with corn stover

|  | Usage | Emission intensity | Emissions from fuel - no export Units | Emissions from fuel - export |
|---|---|---|---|---|
|  | BTU/gal ethanol produced | g $CO_2$eq/mmBTU fuel used | g $CO_2$eq/aggregate mmBTU ethanol produced | g $CO_2$eq/aggregate mmBTU ethanol produced |
| Agriculture/Land Use |  |  | 298 | 298 |
| Fuel Production (cellulosic ethanol and gas fermentation) | | | | |
| Natural Gas | 33,628 | 68,575 | 29,949 | 29,949 |
| Electricity | 2,356 | 219,812 | 6,726 | 6,726 |
| Other |  |  | 2,968 | 2,968 |
| Fuel and Feedstock Transport |  |  | 1,492 | 1,492 |
| Tailpipe Emissions |  |  | 746 | 746 |
| Electricity export credit | (3,863) | 219,812 | — | (11,138) |
| TOTAL |  |  | 42,178 | 31,040 |
| Life cycle GHG emission reduction relative to the gasoline baseline* |  |  | 57% | 68% |

*98,204 g $CO_2$eq/mmBTU ethanol produced obtained from 2010 Final Rule-Federal Register/Vol. 75, No. 58/Friday, Mar. 26, 2010/Rules and Regulations As shown in Table 7 above, the life cycle GHG emission reduction relative to a gasoline baseline for the fuel production process for switch grass which implements the electricity displacement described above is 54% relative to the gasoline baseline, but only 42% without such displacement. A contributor to the favorable GHG emission reduction with the displacement is the electricity export credit of 11,138 g $CO_2$eq/mmBTU ethanol produced. Likewise, as shown in Table 8 above, using corn stover as the feedstock, the life cycle GHG emission reductions are 68% relative to the baseline with displacement of fossil electricity, while only 57% without the displacement.

The above reductions in life cycle GHG emissions due to the displacement can lead to advantaged fuel credit generation. As noted previously, the GHG emission reduction threshold for generation of a Cellulosic Biofuel is 60%, while the threshold for generation of an Advanced Biofuel is 50%. (See Table 2 above). By implementing the displacement described in this example using corn stover as a feedstock, since the GHG emission reduction is 68% relative to the baseline, both thresholds are exceeded. By contrast, without such displacement, since only a 57% reduction relative to the baseline is reached, only the Advanced Biofuel threshold is exceeded (Table 7). Moreover, by practicing the process with displacement using switch grass as the feedstock, since the GHG emission reduction relative to the baseline is 54%, the Advanced Biofuel GHG threshold can be exceeded. However, for the same process without such displacement, the GHG emission reduction is only 42% and thus neither the Advanced Biofuel nor the Cellulosic Biofuel threshold is reached (Table 8).

In addition, embodiments of the invention also enable LCFS fuel credit generation. Under LCFS legislation appreciated by those skilled in the art, the above-noted increased reductions in life cycle GHG emissions with displacement can enable an increase in the number of fuel credits generated.

Example 4

Producing Additional Ethanol from Carbon Dioxide Generated from Anaerobic Digestion of Still Bottoms In this example, ethanol is produced in a cellulosic conversion process utilizing steps of pretreatment, hydrolysis and fermentation. Similar to Example 3, biogenic carbon dioxide is collected during the fermentation and added to fossil derived hydrogen resulting from steam methane reforming and fermented to ethanol. However, in the process described herein, still bottoms remaining after ethanol fermentation are fed to an anaerobic digestion, which produces biogas comprising methane and biogenic carbon dioxide. This additional source of biogenic carbon dioxide present in the biogas is collected and combined with the fossil derived hydrogen and biogenic carbon dioxide from ethanol fermentation. The combined stream is then fermented to produce biogenic ethanol as described previously in Example 3. The biogas comprising methane in turn is introduced to a pipeline and an amount of methane withdrawn from the pipeline is used as transportation fuel. Thus, in addition to using biogenic carbon dioxide from the ethanol fermentation, biogenic carbon dioxide from biogas, that would otherwise be vented, is also utilized to make fuel. Further, since the methane from the biogas is used as transportation fuel, implementing this embodiment results in a higher yield of transportation fuel from the original starting material.

The process flow diagram is shown in FIG. 4. Like reference numbers among FIG. 4 and the earlier described figures represent identical or similar process steps or unit operations.

As shown in FIG. 4, biomass is subjected to a pretreatment 2 to make the biomass more amenable to enzymatic hydrolysis. Pretreatment of the biomass typically involves the addition of pretreatment chemical and heat to hydrolyze at least a portion of the hemicellulose component of the biomass. The pretreated biomass is then hydrolyzed with cellulase enzymes in hydrolysis unit 4 to produce glucose. The hydrolyzed material, comprising glucose and other hexose and pentose sugars, as well as unhydrolyzed, insoluble material comprising lignin, is fed to a fermentation unit 10 to produce a fermented solution 12 comprising biogenic ethanol and biogenic carbon dioxide is collected from the fermentation to produce a biogenic $CO_2$ stream 20. The biogenic $CO_2$ stream 20 is combined with a fossil derived hydrogen stream 30. The fossil derived hydrogen stream 30 is produced from fossil methane using steam methane reforming according to the process described in Example 3 above.

The fermented solution 12 from the fermentation unit 10 is fed to distillation 13 in which ethanol is concentrated. Further concentration of the ethanol is carried out using molecular sieves. A stream remaining after distillation, referred to as a still bottoms stream 14, is fed to anaerobic digestion 16. The anaerobic digestion 16 produces a stream comprising crude biogas 17, which is then fed to $CO_2$ recovery unit 18 in which biogenic carbon dioxide is recovered. The purified biogas 19 is then introduced to a pipeline 21 for transporting methane. Methane is withdrawn from pipeline 21 and used as transportation fuel.

A biogenic carbon dioxide stream 27 from $CO_2$ recovery unit 18 is combined with biogenic carbon dioxide from biogenic $CO_2$ stream 20 and hydrogen from fossil derived hydrogen 30. The resultant combined stream 40 comprises fossil derived hydrogen 30 and biogenic carbon dioxide originating both from biogas and from ethanol fermentation. The combined stream 40 is fermented to biogenic ethanol in fermentation unit 110. A fermented solution stream 120 is sent to distillation unit 130 to concentrate the biogenic ethanol 115.

Byproducts from fermentation bioreactor 110 can be fed to anaerobic digestion 16 or 118 to increase biogas yield. As mentioned, *Clostridium* species, in addition to ethanol, produce acetic acid from gaseous substrates. For example, *Clostridium* species are known to produce acetic acid and/or acetate from hydrogen and carbon dioxide by the following chemical reaction:

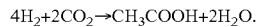

$$4H_2 + 2CO_2 \rightarrow CH_3COOH + 2H_2O.$$

Acetate and/or acetic acid from the fermentation bioreactor unit 110 may be recovered. For example, in one embodiment, the fermentation conditions are optimized to produce acidic acid, which is used in the production of a biofuel. In another embodiment, acetic acid and/or acetate are byproducts of the ethanol production and are fed to anaerobic digestion 16 or 118 in acetate/acetic acid stream 23. The acetic acid and/or acetate from stream 23 is subsequently converted to biogas in the anaerobic digester. Thus, an unwanted byproduct from ethanol fermentation is converted to a further fuel product, thereby resulting in even further improvements in the yield of fuel from the original starting material. Another option for increasing biogas yield involves withdrawing an exhaust gas stream 25 comprising hydrogen, carbon dioxide and carbon monoxide from the headspace of the fermentation bioreactor 110. Introduction of the exhaust gas stream 25 to anaerobic digestion 16 could potentially further increase biogas yield from the anaerobic digestion 16.

Although the production of biogas from still bottoms from stream 14 from sugar fermentation 10 and distillation 13 is described, along with carbon dioxide recovery, biogas can also be produced from still bottoms stream 117 resulting from distillation 130 of ethanol produced in fermentation bioreactor 110 from biogenic carbon dioxide and hydrogen followed by anaerobic digestion 118. Biogenic carbon dioxide present in the biogas stream 121 resulting from anaerobic digestion 118 can be recovered in $CO_2$ recovery 122. The recovered carbon dioxide in carbon dioxide stream 123 can be combined with biogenic carbon dioxide stream 27 withdrawn from $CO_2$ recovery unit 18 or 15. The purified biogas can be introduced to a pipeline 21 separately or together with biogas from stream 19. Advantageously, this process increases the available biogenic carbon for producing fuels from a cellulosic feedstock. For example, as discussed above, the fermentation of glucose at 10 produces two molecules of ethanol and two molecules of carbon dioxide by the following reaction:

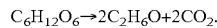

$$C_6H_{12}O_6 \rightarrow 2C_2H_6O + 2CO_2.$$

By recovering the bio-$CO_2$ from this fermentation step 10, and by recovering bio-$CO_2$ and/or biomethane from the anaerobic digestion step 16, the amount of available biocarbon for producing fuels may be increased above the theoretical yield of the fermentation step. Accordingly, in addition to the renewable fuel credit that may be obtained for the ethanol produced in step 13, a renewable fuel credit (e.g., a RIN credit) may be obtained for the ethanol produced in step 130, for the purified biogas produced in step 122, and/or any combination thereof.

Example 5

Heat Integration

An advantage of producing hydrogen at the same location as a fermentation plant is that energy generated during and/or for the steam methane reforming can be used in various stages of the process to produce and recover a fermentation product. Since many stages of the fermentative process are energy-intensive, this can significantly reduce the costs of operating.

Such heat can be utilized in a dryer, thermal oxidizer, distillation and/or evaporation in an ethanol production process using corn as a feedstock. Heat can also be supplied in production processes to make other fermentation products, such as organic acids.

Figure 5:
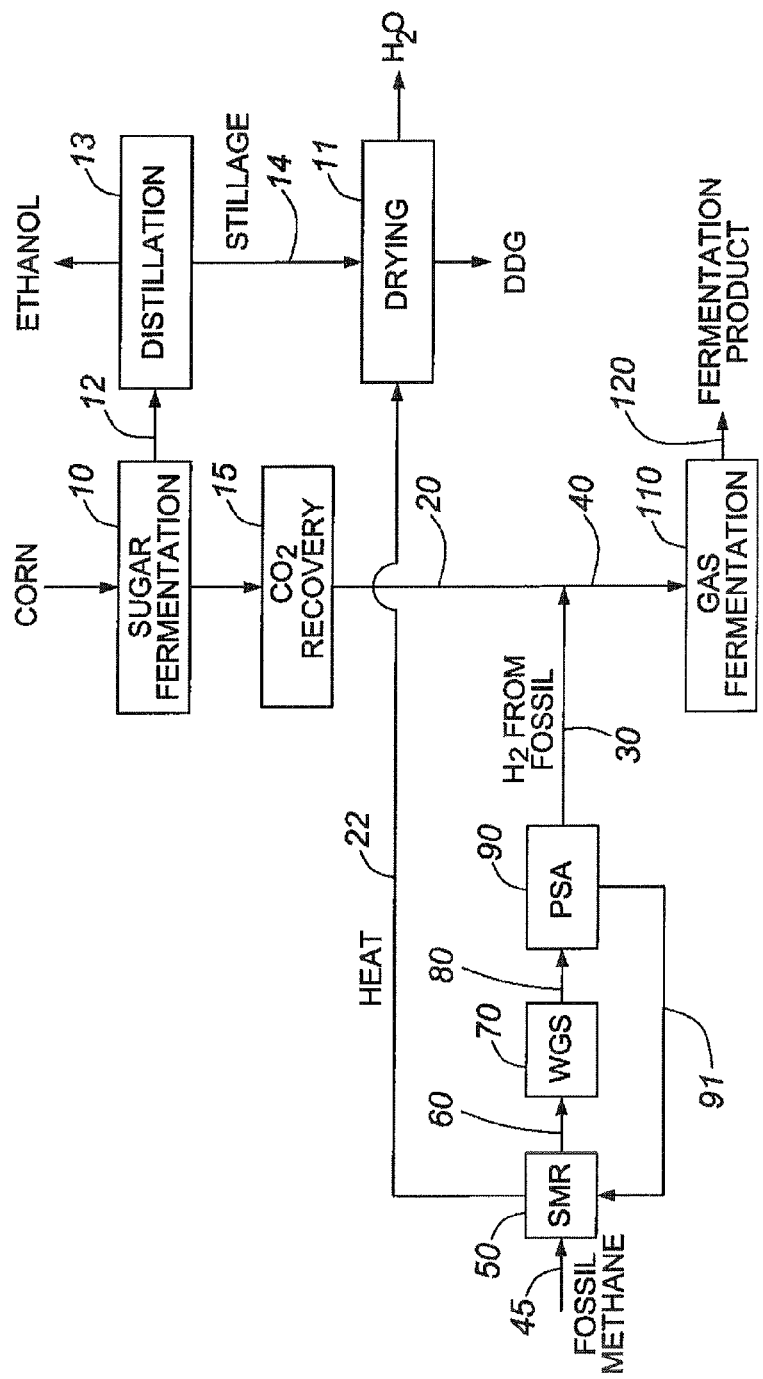
FIG. 5 is a process flow diagram showing the production of biogenic ethanol from gaseous fermentation of fossil derived hydrogen and biogenic carbon dioxide in a process in which the biogenic carbon dioxide is recovered from fermentation of sugar to ethanol and in which heat from a steam methane reforming unit used to make fossil derived hydrogen is provided as an energy source for drying a waste stream that originates from the fermentation of sugar to ethanol.

An example of such a process is described in FIG. 5. Like reference numbers among FIG. 5 and the earlier described figures represent identical or similar process steps or unit operations.

As shown in FIG. 5, corn is the feed to a dry milling process employing fermentation 10 to produce biogenic ethanol. The corn is first treated by grinding and enzyme treatment in a slurry. The resultant slurry is then fed to fermentation unit 10 and fermented with *Saccharomyces cerevisiae* yeast to produce ethanol and biogenic $CO_2$ which is purified at $CO_2$ recovery 15 to produce a biogenic $CO_2$ stream 20. The biogenic $CO_2$ stream 20 is combined with fossil derived hydrogen stream 30 to produce a combined stream 40 comprising biogenic $CO_2$ and fossil derived hydrogen. The fermented solution 12 from the fermentation unit 10 is fed to distillation 13 in which ethanol is concentrated. Further concentration of the ethanol is carried out using molecular sieves. A stream remaining after distillation, referred to as a still bottoms or "stillage" stream 14, is fed to a drying unit 11 where water is driven off. The product of the drying step is a dried distiller's grain (DDG) that can be used as a protein supplement in livestock feed. However, the drying step to produce this byproduct is energy intensive. As set forth below, heat from a reforming step can be used to dry the stillage stream 14.

The biogenic $CO_2$ stream 20 is combined with fossil derived hydrogen stream 30 to produce a combined stream 40 comprising biogenic $CO_2$ and fossil derived hydrogen. The combined stream 40 comprising biogenic carbon dioxide and fossil derived hydrogen is fermented in fermentation 110 to produce a fermentation product 120. The fermentation product may be ethanol, acetic acid, a salt of acetic acid, or a combination thereof. Other products from the gaseous fermentation 110 may include butyric acid. Ethanol or acetic acid can also be used as intermediates to produce other fuels.

The fossil derived hydrogen stream 30 is produced from fossil methane using steam methane reforming according to the process described in Example 3 above. During steam methane reforming, energy is supplied to the SMR unit 50 using a fuel gas such as methane. The fuel gas is burned in a furnace that supplies heat to the SMR unit 50. In this example, further gases to fuel the furnace of the SMR unit 50 are supplied by purge gas stream 91. As would be appreciated by those of skill in the art, the SMR unit 50 operates at high temperature, such as greater than 500° C.

The heat from the SMR unit 50 can be supplied by heat stream 22 to the drying unit 11 to produce DDG. Since the drying step to produce this byproduct is energy intensive, integrating hydrogen production and fermentation can significantly reduce energy costs. Stream 22 can also be used to produce electricity for process needs.

Thus, this example demonstrates that using heat energy from the SMR unit 50 can reduce energy requirements for processes including sugar fermentation to ethanol or other products, while at the same time enable production of an additional product from carbon dioxide recovered from the sugar fermentation.

Example 6

Producing Biogenic Gasoline Using Fossil Derived Hydrogen and Biogenic Carbon Dioxide In this example, biogenic gasoline is produced from fossil derived hydrogen and biogenic carbon dioxide. In the process detailed below, carbon dioxide and fossil derived hydrogen are fed to a steam methane reformer. In the reformer, the biogenic carbon dioxide and fossil derived hydrogen react to produce a syngas stream comprising carbon monoxide, hydrogen and carbon dioxide via a reverse water gas shift reaction. The resultant syngas, containing biogenic carbon and fossil derived hydrogen, is then converted to gasoline via methanol and dimethylether intermediates as described below. Advantageously, the gasoline qualifies as biogenic since the carbon atoms in the molecule originate from biogenic carbon dioxide and/or qualify as renewable.

A process study design was conducted for the foregoing process by generating modeling data. The process flow sheet and data are described in relation to FIG. 6.

The study design was based on the availability of 1,000 metric tons of biogenic carbon dioxide per day (t/d), indicated in FIG. 6 as biogenic $CO_2$ stream 20. The biogenic $CO_2$ stream 20 is collected from $CO_2$ recovery 15 after fermentation of non-fossil organic material to produce ethanol, from gasification of biomass or from anaerobic digestion of landfill waste (not shown). Biogenic $CO_2$ stream 20 is treated to remove impurities such as sulfur compounds as they are poisonous to the reforming catalyst (not shown). The biogenic $CO_2$ stream 20 is then compressed in $CO_2$ compression unit 25 to produce a compressed biogenic $CO_2$ stream 28. The temperature of the compressed biogenic $CO_2$ stream 28 is 200° F. (93° C.), the pressure is 430 psig and the total flow is 2098.8 lbmol/hr. The compressed biogenic $CO_2$ stream 28 is then combined with a fossil derived hydrogen stream 30 and a steam stream 32. The fossil derived hydrogen stream 30 has a temperature of 108° F. (42° C.), a pressure of 430 psig and a total flow of 7491 lbmol/hr. The steam stream 32 is at a temperature of 750° F. (399° C.), a pressure of 450 psig and a total flow of 2214.6 lbmol/hr.

The fossil derived hydrogen stream 30 is produced by steam methane reforming and a water gas shift reaction (not shown). The overall reaction for production of hydrogen is

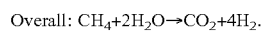

Overall: $CH_4 + 2H_2O \rightarrow CO_2 + 4H_2$.

The fossil carbon dioxide produced from the above reaction is introduced underground to extract oil in an enhanced oil recovery operation (not shown).

The combined stream 40 comprising the hydrogen, biogenic carbon dioxide and steam is fed to a pre-heater 42 at a temperature of 212° F. (100° C.). The temperature of the outlet stream 44 from the pre-heater is 1000° F. (538° C.). The heated outlet stream 44 that is fed to a reformer 46 comprises the following components on a mole % basis: $H_2O$ (0.1887), $N_2$ (0.0026), $CO_2$ (0.1771), $H_2$ (0.6299), CO (0.0000) and $CH_4$ (0.0018). The steam reformer 46 operating conditions were adjusted to match the requirements for syngas fed to the gasoline production process. The steam reforming conditions used for the example were:

TABLE 9

| Steam reforming conditions | |
| --- | --- |
| Catalyst tube outlet temperature | 1600° F. (871° C.) |
| Catalyst tube outlet pressure | 400 psig |
| Steam reformer feed pre-heat | 1000° F. (538° C.) |
| Radiant section Bridgewall Temperature (BWT) | 1800° F. (982° C.) |
| Steam:carbon molar ratio | 1.05 |

The steam reformer 46 produces an outlet stream 48 comprising the following components on a mole % basis $H_2O$ (0.3411), $N_2$ (0.0027), $CO_2$ (0.0616), $H_2$ (0.4698), CO (0.1017) and $CH_4$ (0.0232).

After the steam reformer 46, the outlet stream 48, which is at a temperature of 1600° F. (871° C.) is sent to a waste heat boiler (WHB) unit 52, which recovers energy from the outlet stream 48. An outlet stream 54 from the WHB unit 52, at a temperature of 1100° F. (593° C.) is fed to a heat recovery unit 56. An outlet stream 58 from the heat recovery unit 56 at a temperature of 338° F. (170° C.) is fed to coolers 62, which produce a steam condensate stream 64 and a cooled syngas stream 66. The conversion of feed carbon from the biogenic carbon dioxide to carbon monoxide in syngas was determined to be 54.6%.

The syngas stream 66 can be used in various ways (not illustrated in FIG. 6). For example, in order to produce biogenic gasoline, the syngas stream 66 produced by the above reforming process is converted to methanol and the methanol is then converted to dimethylether by a dehydration reaction. Subsequently, an equilibrium mixture of methanol, dimethylether and water is converted to short-chain olefins. In a further reaction step, the short-chain olefins are reacted to form higher olefins, including n/iso-paraffins, aromatics and napththenes, which are further treated to make the biogenic gasoline.

The foregoing process may employ heat integration. The steam reformer 46 to produce syngas from biogenic carbon dioxide and hydrogen and the steam methane reforming and/or a water gas shift to produce the hydrogen 30 from fossil methane often generate excess heat. The heat generated from any one or a combination of these reforming and water gas shift operations can be used to provide energy in other unit operations. For instance, the heat can be used to supply energy for converting non-fossil organic material to ethanol from which the biogenic $CO_2$ feed 20 is produced as a byproduct. For example, such heat can be utilized in a dryer, thermal oxidizer, distillation and/or evaporation in an ethanol production process using corn as a feedstock. Alternatively, the heat can be used in a production process to make ethanol from biomass or biomass derived material. This includes supplying heat to similar operations as a corn ethanol process or for pretreatment processes that are utilized to make the biomass or biomass derived material more accessible to cellulase enzymes for cellulose hydrolysis. Heat from the reforming can also be used to supply energy for the gasoline production process in which syngas is converted to biogenic gasoline via the methanol and dim-ethylether intermediates as described above. Further, the heat from the steam reformer 46 or the reformer or water-gas shift unit (not shown) to produce the fossil derived hydrogen 30 can be used to produce electricity for export to the grid. Such energy savings can contribute to reducing the life cycle GHG emissions of the biogenic gasoline relative to a gasoline baseline and can enable the generation of a valuable biofuel credit in relation to the biogenic gasoline produced or sold.

Example 7

Producing Additional Ethanol from Acetic Acid

Figure 8:
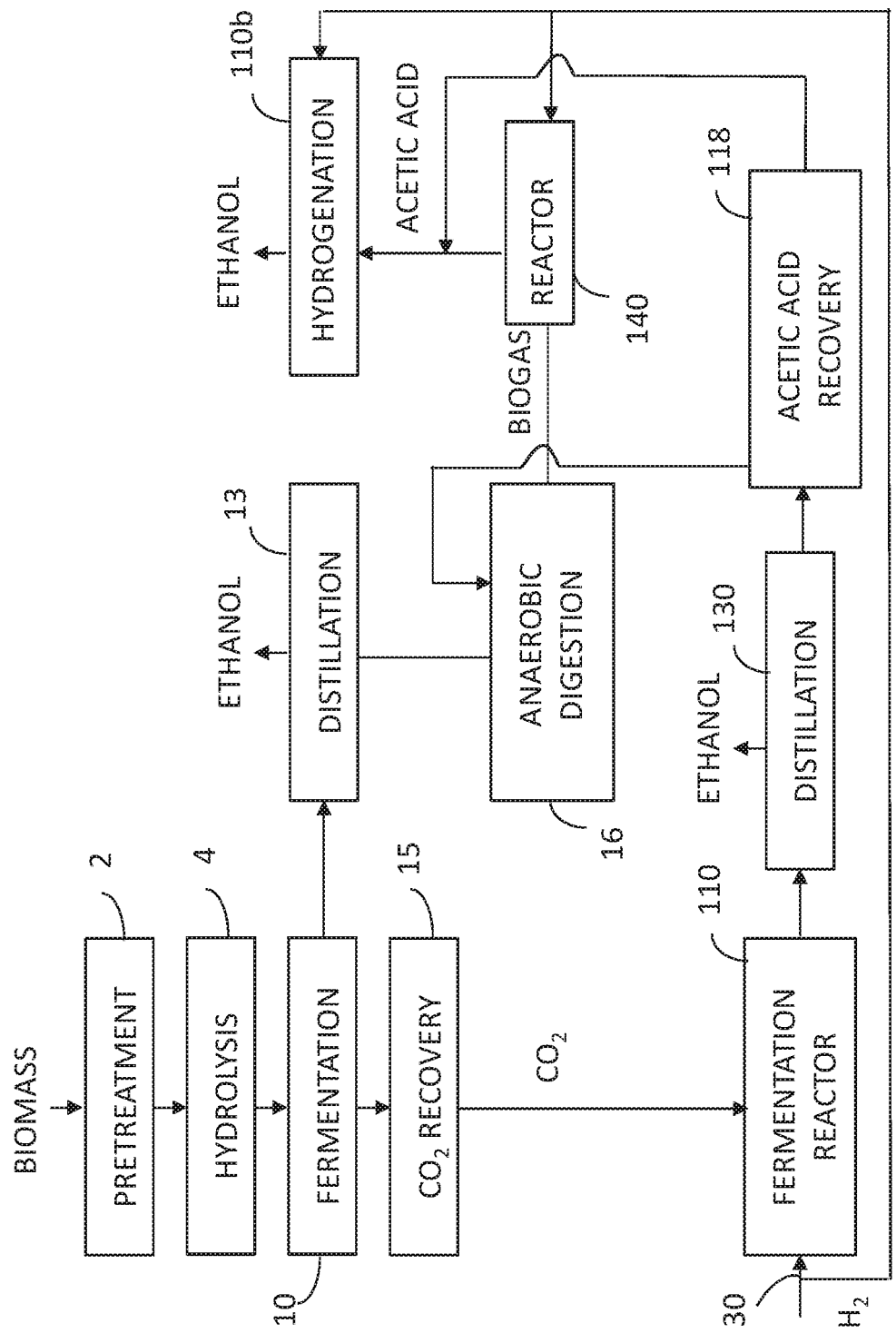
FIG. 8 is a process flow diagram showing the production of biogenic ethanol from gaseous fermentation of fossil derived hydrogen and biogenic carbon dioxide in accordance with one embodiment of the invention.

In this example, ethanol is produced in a cellulosic conversion process utilizing steps of pretreatment 2, hydrolysis 4, and fermentation 10. Similar to Example 4, FIG. 8 shows that biogenic carbon dioxide is collected from the fermentation 10, is fed to $CO_2$ recovery 15, and is mixed with a stream of fossil derived hydrogen 30 produced from steam methane reforming (SMR). Depending on the fermentation conditions and/or microorganisms in fermentation reactor 110 this fermentation may provide ethanol, acetic acid, and/or acetate. The acetic acid and/or acetate is then optionally combined with acetic acid and/or acetate produced elsewhere within the process, and converted to ethanol. For example, in one embodiment the additional acetic acid/acetate is optionally obtained as a product and/or by-product of fermentation 10, as a product and/or by-product of another stage in the process, and/or is generated from biogas and/or syngas generated within the process. For example, in one embodiment, acetic acid is produced from syngas, which is generated within the process (e.g., from gasification of lignin).

As discussed above, biogenic $CO_2$ in biogas may be collected and/or used to produce acetic acid. For example, in one embodiment, the $CO_2$ in the biogas collected from anaerobic digestion 16 is recovered (not shown) and converted to CO and $H_2O$ via the reverse water gas shift reaction in reactor 140. The CO is then further reacted with $H_2$ to make methanol, which is reacted with more CO to make acetic acid. In other embodiments, the biogas is converted to acetic acid and/or acetate via a different set of reactions in the reactor 140, which may consume additional hydrogen.

In one embodiment, the acetic acid is converted to ethanol via a hydrogenation reaction. For example, in one embodiment, the acetic acid/acetate collected from various points within the process is hydrogenated to produce ethanol by a hydrogenation process that uses hydrogen that is at least partially derived from fossil natural gas. Accordingly, the relatively high energy and low cost of natural gas is used to provide a biogenic fuel, such as ethanol, that meets GHG targets established by regulators. For example, the resulting ethanol can have at least 20% GHG emissions reduction versus a gasoline baseline. Accordingly, this process may increase the ability to obtain RINS by using natural gas energy as energy content to produce a renewable fuel without compromising the renewable biofuel status of the fuel.

In one embodiment, the acetic acid/acetate is converted to ethanol as part of the Celanese TCX™ process, or a portion thereof. For example, in one embodiment, the collected acetic acid/acetate is hydrogenated in the presence of a TCX™ catalyst. In another embodiment, biogas containing methane and/or other hydrocarbons are collected from the process and converted to acetic acid, which is then hydrogenated in a hydrogenation reactor 110b (e.g., from hydrogen obtained by methane reforming).

Advantageously, this example may involve providing different feeds to the hydrogenation of acetic acid to ethanol, thus significantly increasing the yield of renewable fuel relative to using only one feed. More specifically, by splitting fractions of the biomass, and using different approaches to produce fuel therefrom, the yield significantly increases. For example, although the sugar fractions of biomass are readily converted to ethanol via fermentation, the remaining fractions are not easily converted. In one embodiment, these non-fermented materials are converted to ethanol (i.e., increasing the total ethanol yield for the same quantity of cellulosic feedstock) by converting the non-fermented materials to biogas (e.g., via one or more anaerobic digestions and/or thermal processes), converting the biogas to acetic acid, and converting the acetic acid to ethanol.

Further advantageously, the additional ethanol yield is provided from materials that traditionally are considered waste streams generated during the production of cellulosic ethanol and/or that traditionally are used to produce heat and/or energy for use within the process. Producing ethanol from these waste streams maximizes the amount of ethanol generated from the total biogenic carbon in the feedstock, thus increasing the total ethanol yield for a given amount of feedstock.

In addition to increasing the total ethanol yield, splitting the biomass into different fractions for different fermentations to produce ethanol has various synergistic advantages. Different streams are each more suited to different processes and individual streams can be more efficiently processed by optimally combining conversion technologies. Thus, in producing a high yield of biogenic ethanol, there can be reduced overall capital and operating costs.

It should be understood that the foregoing examples describing the production of biogenic ethanol and gasoline are for illustrative purposes only and should not be construed to limit the current invention in any manner.

The invention claimed is:

1. A process for producing a fuel or fuel intermediate containing carbon derived from non-fossil organic material comprising:
   (i) providing biogenic carbon dioxide that is sourced from a production process comprising at least one of a step of fermentation and a thermal process, said production process producing a first product derived from the non-fossil organic material, said first product selected from: (a) an energy product; (b) a biogenic carbon-based product selected from a chemical product, a fuel and a fuel intermediate; and (c) a combination thereof, wherein the biogenic carbon dioxide is generated during the production process;
   (ii) providing a stream enriched in hydrogen that is sourced from a hydrogen production process, the hydrogen production process including a step of removing fossil carbon dioxide from a stream including hydrogen to provide the steam enriched in hydrogen;
   (iii) converting the biogenic carbon dioxide and hydrogen from the enriched hydrogen stream to a second product, said second product comprising at least one of a biogenic carbon-based fuel and a biogenic carbon-based fuel intermediate; and
   (iv) carrying out or arranging for one or more parties to carry out at least one step that contributes to a reduction in the life cycle greenhouse gas (GHG) emissions of the second product.

2. The process according to claim 1, wherein the biogenic carbon dioxide is sourced from a production process comprising a step of fermentation.

3. The process according to claim 2, wherein said at least one step that contributes to a reduction in the life cycle greenhouse gas (GHG) emissions of the second product is selected from:
   (a) introducing at least a portion of fossil carbon dioxide recovered from one or more streams comprising fossil carbon dioxide generated during said hydrogen production process into an apparatus for transporting carbon dioxide, withdrawing carbon dioxide from said apparatus and introducing the withdrawn carbon dioxide underground, and
   (b) using at least a portion of the first product to displace the use or production of a corresponding fossil-based product, wherein the first product is selected from the chemical product and the energy product.

4. The process according to claim 1, wherein the second product is methane or gasoline.

5. The process according to claim 1, wherein the second product is a liquid hydrocarbon produced by a Fischer Tropsch reaction.

6. The process according to claim 1, wherein each of the first and the second products comprises an alcohol.

7. The process of claim 6, wherein the alcohol is methanol or ethanol.

8. The process of claim 3, wherein the first product produced from the non-fossil organic material is an energy product.

9. The process of claim 8, wherein the energy product is at least one of steam, electricity, methane, and lignin.

10. The process of claim 8, wherein the energy product comprises at least one of steam and electricity generated by combusting lignin.

11. The process according to claim 1, wherein the first product comprises ethanol.

12. The process according to claim 1, wherein the second product comprises one of ethanol and acetic acid.

13. The process according to claim 1, wherein converting the biogenic carbon dioxide and the hydrogen to the second product comprises at least one of a chemical and biological conversion.

14. The process according to claim 1, comprising generating or causing the generation of a fuel credit.

15. The process according to claim 1, comprising generating or causing the generation of a biofuel credit for each of the first and the second products, wherein each of the first and second products is ethanol.

16. The process according to claim 2, wherein the step of fermentation provides a fermentation product, and wherein the production process comprises:
   distilling the fermentation product to provide an alcohol;
   subjecting still bottoms from the distilling to an anaerobic digestion to provide crude biogas;
   removing carbon dioxide from the crude biogas; and
   generating or causing the generation of a biofuel credit for at least one of the purified biogas, the first product, and the second product, wherein each of the first and second products are produced by a process using at least one of heat and energy produced by combusting the purified biogas.

17. The process according to claim 16, wherein the carbon dioxide removed from the crude biogas is introduced to step (iii).

18. The process according to claim 1, comprising providing data for authenticating at least one of a fuel and a fuel intermediate derived from the second product as eligible for a renewable fuel credit.

19. The process according to claim 1, wherein the hydrogen production process comprises:
(a) converting fossil methane to carbon monoxide and hydrogen by reforming;
(b) converting at least a portion of the carbon monoxide by a water-gas shift reaction to carbon dioxide, thereby producing a stream comprising fossil carbon dioxide and the stream comprising hydrogen, and
(c) separating at least a portion of the hydrogen from the stream of step (b) from non-hydrogen components to produce the stream enriched in hydrogen and a stream comprising fossil carbon dioxide.

20. The process according to claim 19, comprising using heat from the reforming as process energy (a) in the production process of step (i); (b) in one or more stages of a process comprising step (iii) to produce the biogenic carbon-based fuel, fuel intermediate or chemical product; or (c) a combination thereof.

21. The process according to claim 19, wherein a chemical product is produced in step (iii), and wherein the chemical product is acetic acid, acetate, or a combination thereof.

22. The process according to claim 16, wherein converting the biogenic carbon dioxide and hydrogen from the enriched hydrogen stream to a second product includes introducing said biogenic carbon dioxide and said enriched hydrogen stream into a fermentation bioreactor, and comprising feeding exhaust from the fermentation bioreactor to the anaerobic digestion to produce additional crude biogas.

23. The process according to claim 1, wherein the life cycle GHG emissions are at least 50% lower than a gasoline baseline as measured by EPA methodology.

24. The process according to claim 1, wherein the production process comprises:
pretreating a feedstock;
fermenting at least a portion of the pretreated feedstock to provide a fermentation product;
distilling the fermentation product to provide an alcohol;
subjecting still bottoms from the distilling to an anaerobic digestion to provide crude biogas;
converting the crude biogas to acetic acid; and
converting the acetic acid to ethanol.

25. The process according to claim 1, wherein the production process comprises:
pretreating a feedstock;
fermenting at least a portion of the pretreated feedstock to provide a fermentation product;
distilling the fermentation product to provide an alcohol;
converting a second portion of the feedstock to crude biogas;
converting the crude biogas to acetic acid; and
converting the acetic acid to ethanol.

26. The process according to claim 1, wherein the molar ratio of hydrogen to fossil carbon monoxide and fossil carbon dioxide in said enriched hydrogen stream is greater than 4:1.

27. The process according to claim 1, wherein the step of converting the biogenic carbon dioxide and hydrogen to a second product comprises a biological conversion of the biogenic carbon dioxide and the hydrogen to ethanol by a bacterium from the genus *Clostridium*.

28. The process according to claim 1, wherein the molar ratio of hydrogen to fossil carbon monoxide and carbon dioxide in said stream comprising hydrogen is greater than 6:1.

29. The process according to claim 1, comprising:
carrying out anaerobic digestion of a process stream comprising organic components to produce a crude biogas comprising biogenic carbon dioxide;
removing at least a portion of the biogenic carbon dioxide from the crude biogas to produce a stream comprising additional biogenic carbon dioxide; and
introducing said additional biogenic carbon dioxide removed from the crude biogas to step (iii), step (i) or both steps.

30. The process of claim 29, wherein the second product comprises ethanol, and comprising generating or causing the generation of a fuel credit for the ethanol.

31. The process according to claim 1, wherein the biogenic carbon dioxide provided in step (i) is processed to remove oxygen.

32. A process for producing a biogenic carbon-based fuel, fuel intermediate or chemical product comprising:
(i) providing biogenic carbon dioxide that is sourced from non-fossil organic material;
(ii) providing a stream comprising hydrogen by converting fossil methane to carbon monoxide and hydrogen by reforming;
(iii) fermenting the biogenic carbon dioxide from step (i) and hydrogen produced in step (ii) to a biogenic carbon-based fuel, fuel intermediate or chemical product;
(iv) carrying out anaerobic digestion on a stream produced from the process comprising organic components to produce biogas;
(v) obtaining a byproduct from step (iii) of fermenting; and
(vi) introducing the byproduct to the anaerobic digestion of step (iv).

33. The process of claim 32, wherein the byproduct is acetate, acetic acid, or a combination thereof.

34. The process of claim 32, wherein the byproduct is an exhaust gas stream obtained from a fermentor used in step (iii) of fermenting, which exhaust gas stream comprises at least one of hydrogen, carbon monoxide and carbon dioxide.

35. The process of claim 32, wherein at least a portion of the carbon monoxide is converted by a water-gas shift reaction to carbon dioxide, thereby producing a stream comprising carbon dioxide and hydrogen, and at least a portion of the hydrogen from the stream comprising carbon dioxide and hydrogen is separated from non-hydrogen components to produce the stream comprising hydrogen.

36. The process of claim 32, wherein the biogenic carbon dioxide provided in step (i) is processed to remove oxygen.

37. A process for producing a fuel or fuel intermediate containing carbon derived from non-fossil organic material comprising:
(i) providing biogenic carbon dioxide that is sourced from a production process comprising at least one of a step of fermentation and a thermal process, said production process producing a first product derived from the non-fossil organic material, said first product selected from: (a) an energy product; (b) a biogenic carbon-based product selected from a chemical product, a fuel and a fuel intermediate; and (c) a combination thereof, wherein the biogenic carbon dioxide is generated during the production process;

(ii) providing a stream enriched in hydrogen that is sourced from a hydrogen production process, the hydrogen production process including a step of removing fossil carbon dioxide from a stream including hydrogen to provide the steam enriched in hydrogen;

(iii) converting the biogenic carbon dioxide and hydrogen from the enriched hydrogen stream to a second product, said second product comprising acetic acid, acetate, or a combination thereof, (iv) providing an aqueous stream comprising biogenic carbon originating from the production process in step (i) and converting it to acetic acid, acetate, or a combination thereof; and (v) converting acetic acid, acetate, or combination thereof produced in at least one of steps (iii) and (iv) to ethanol.

38. The process according to claim 37, wherein the process produces a first product derived from non-fossil organic material, said first product selected from: (a) an energy product; (b) a biogenic carbon-based product selected from a chemical product, a fuel and a fuel intermediate; and (c) a combination thereof, wherein biogenic carbon dioxide is generated during the step of fermenting, the process comprising:

providing the biogenic carbon dioxide generated during the step of fermenting, providing a stream enriched in hydrogen that is sourced from a hydrogen production process, the hydrogen production process including a step of removing fossil carbon dioxide from a stream including hydrogen to provide the steam enriched in hydrogen; and converting the biogenic carbon dioxide and hydrogen from the enriched hydrogen stream to a second product, said second product comprising at least one of a biogenic carbon-based fuel and a biogenic carbon-based fuel intermediate; and carrying out or arranging for one or more parties to carry out at least one step that contributes to a reduction in the life cycle greenhouse gas (GHG) emissions of the second product.

39. The process according to claim 38, wherein the ethanol converted from acetic acid, acetate, or a combination thereof has life cycle greenhouse gas (GHG) emissions that are at least 50% lower than a gasoline baseline as measured by Environmental Protection Agency (EPA) methodology.

40. The process according to claim 39, wherein step (iv) comprises feeding the aqueous stream comprising biogenic carbon to an anaerobic digester to provide biogas, and combining the biogas with a stream enriched in hydrogen that is sourced from the hydrogen production process.

* * * * *

UNITED STATES PATENT AND TRADEMARK OFFICE
CERTIFICATE OF CORRECTION

PATENT NO. : 10,640,793 B2
APPLICATION NO. : 15/327345
DATED : May 5, 2020
INVENTOR(S) : Patrick J. Foody It is certified that error appears in the above-identified patent and that said Letters Patent is hereby corrected as shown below:

On the Title Page

On page 2, in Column 2, item (56), Other Publications, Line 26, delete "Dualifying" and insert --Qualifying--.

On page 3, in Column 1, item (56), Other Publications, Line 11, delete "Fas" and insert --Gas--.

On page 3, in Column 2, item (56), Other Publications, Line 4, delete "Oili" and insert --oil--.

In the Specification

In Column 16, Line 37, delete "itaconoic" and insert --itaconic--.

In Column 16, Line 38, delete "sesquiturpenes" and insert --sesquiterpenes--.

In Column 22, Line 59, delete "2-pyrolidone," and insert --2-pyrrolidone--.

In Column 22, Line 67, delete "monethanolamine." and insert --monoethanolamine.--.

In Column 29, Line 33, delete "napththenes," and insert --naphthenes,--.

In Column 57, Line 44, delete "napththenes," and insert --naphthenes,--.

In Column 58, Lines 28-29, delete "by-product" and insert --byproduct--.

In Column 58, Line 29, delete "by-product" and insert --byproduct--.

In the Claims

In Column 59, Line 58, Claim 1, delete "steam" and insert --stream--.

Signed and Sealed this
Seventh Day of June, 2022

Katherine Kelly Vidal
*Director of the United States Patent and Trademark Office*